US008815274B2

(12) United States Patent
DesNoyer et al.

(10) Patent No.: US 8,815,274 B2
(45) Date of Patent: Aug. 26, 2014

(54) POLY(ESTER AMIDES) FOR THE CONTROL OF AGENT-RELEASE FROM POLYMERIC COMPOSITIONS

(75) Inventors: Jessica R. DesNoyer, San Jose, CA (US); Stephen D. Pacetti, San Jose, CA (US); Lothar W. Kleiner, Los Altos, CA (US); Syed F. A. Hossainy, Fremont, CA (US); Yung-Ming Chen, Cupertino, CA (US); Gordon Stewart, San Francisco, CA (US); Gina Zhang, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 862 days.

(21) Appl. No.: 12/478,693

(22) Filed: Jun. 4, 2009

(65) Prior Publication Data

US 2009/0297583 A1 Dec. 3, 2009

Related U.S. Application Data

(63) Continuation of application No. 11/187,467, filed on Jul. 22, 2005, now abandoned, which is a continuation-in-part of application No. 10/835,656, filed on Apr. 30, 2004, now Pat. No. 7,820,732, and a continuation-in-part of application No. 10/855,294, filed on May 26, 2004, now abandoned, and a continuation-in-part of application No. 11/115,631, filed on Apr. 26, 2005, now abandoned, and a continuation-in-part of application No. 11/119,020, filed on Apr. 29, 2005, now abandoned.

(51) Int. Cl.
A61F 13/00 (2006.01)

(52) U.S. Cl.
USPC ........... 424/422; 424/423; 424/424; 424/425; 424/426

(58) Field of Classification Search
None
See application file for complete search history.

(56) References Cited

U.S. PATENT DOCUMENTS

| | | | |
|---|---|---|---|
| 4,304,767 A | 12/1981 | Heller et al. | |
| 5,085,629 A | 2/1992 | Goldberg et al. | |
| 5,231,140 A | 7/1993 | Kilburg et al. | |
| 5,376,406 A | 12/1994 | Asanuma et al. | |
| 5,462,828 A | 10/1995 | Moffat et al. | |
| 5,581,387 A | 12/1996 | Cahill | |
| 5,861,387 A | 1/1999 | Labrie et al. | |
| 5,932,539 A | 8/1999 | Stupp et al. | |
| 6,600,010 B2 | 7/2003 | Mao et al. | |
| 6,703,040 B2 | 3/2004 | Katsarava et al. | |
| 7,141,061 B2 | 11/2006 | Williams et al. | |
| 7,820,732 B2 | 10/2010 | Tang et al. | |
| 8,192,752 B2 | 6/2012 | Tang et al. | |
| 2002/0091230 A1 | 7/2002 | Mao et al. | |
| 2003/0057601 A1 | 3/2003 | Reitz et al. | |
| 2003/0083646 A1 | 5/2003 | Sirhan et al. | |
| 2003/0203991 A1 | 10/2003 | Schottman et al. | |
| 2004/0034409 A1 | 2/2004 | Heublein et al. | |
| 2004/0098110 A1 | 5/2004 | Williams et al. | |
| 2004/0126405 A1 | 7/2004 | Sahatjian et al. | |
| 2004/0170685 A1* | 9/2004 | Carpenter et al. | ............ 424/468 |
| 2005/0048121 A1 | 3/2005 | East et al. | |
| 2005/0106204 A1 | 5/2005 | Hossainy et al. | |
| 2005/0265960 A1 | 12/2005 | Pacetti et al. | |
| 2006/0240065 A1 | 10/2006 | Chen | |
| 2006/0246109 A1 | 11/2006 | Hossainy et al. | |

FOREIGN PATENT DOCUMENTS

| | | |
|---|---|---|
| JP | 09-511666 | 11/1997 |
| JP | 11-319071 | 11/1999 |
| JP | 2001-519842 | 10/2001 |
| JP | 2003-517889 | 6/2003 |
| WO | WO 98/32777 | 7/1998 |
| WO | WO 00/56376 | 9/2000 |
| WO | WO 02/18477 | 3/2002 |
| WO | WO 03/064496 | 8/2003 |
| WO | WO 2004/014449 | 2/2004 |
| WO | WO 2004/022119 | 3/2004 |
| WO | WO 2004/028589 | 4/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/066241 | 7/2005 |
| WO | WO 2005/089824 | 9/2005 |

OTHER PUBLICATIONS http://en.wiktionary.org/wiki/alkylene.*
Notification of Refusal for appl. 2007-510949, mailed Jun. 21, 2011, 6 pgs.
Partial Translation of the Notification of Refusal for appl. 2007-510949, mailed Jun. 21, 2011, 2 pgs.
European Search Report for 05741085.4, mailed Jul 16, 2007, 13 pgs.
Odian Principles of Polymerization, $3^{rd}$. Ed., table 1-3, 1991.
Campbell, *Introduction to Synthetic Polymers*, Oxford University Press pp. 45-50 (1994).
Chandrasekar et al., *Coronary Artery Endothelial Protection After Local Delivery of 17β-Estradiol During Balloon Angioplasty in A Porcine Model: a Potential New Pharmacologic Approach to Improve Endothelial Function*, J. of Am. College of Cardiology, vol. 38, No. 5, (2001) pp. 1570-1576.
Chung et al., *Synthesis and Characterization of Wholly Aromatic Polyesters Derived from 1-Phenyl-2,6-naphthalene-dicarboxylic Acid and Aromatic Diols*, Journal of Polymer Science: Part A: Polymer Chemistry, vol. 34, pp. 1105-1112 (1996).
De Lezo et al., *Intracoronary Ultrasound Assessment of Directional Coronary Atherectomy: Immediate and Follow-Up Findings*, JACC vol. 21, No. 2, (1993) pp. 298-307.

(Continued)

Primary Examiner — James Rogers
(74) Attorney, Agent, or Firm — Squire Patton Boggs (US) LLP

(57) ABSTRACT

The present invention generally encompasses a medical article, such as a medical device or coating comprising an agent or combination of agents, wherein the agent is distributed throughout a polymeric matrix. The polymeric matrix comprises an agent and a poly(ester amide) having a design that was preselected to provide a predetermined release rate of the combination of agents from the medical article.

36 Claims, 10 Drawing Sheets

(56) References Cited

OTHER PUBLICATIONS

Hsu et al., *The Influence of Aromatic Dials on Thermotropic Poly(ester-amide)s Synthesized by Direct Polycondensation*, Journal of Polymer Research, vol. 3, No. 2, pp. 89-95, Apr. 1996.

Larrain et al., *Glass Transition Temperature-molecular Weight Relation for Poly(hexamethylene perchloroterephthalamide)*, Polymer Bulletin 4, pp. 487-490 (1981).

Moreno et al., *Macrophage Infiltration Predicts Restenosis After Coronary Intervention in Patients with Unstable Angina*, Circulation, vol. 94, No. 12, (1996) pp. 3098-3102.

Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.

Scully et al., *Effect of a heparan sulphate with high affinity for antithrombin III upon inactivation of thrombin and coagulaton Factor Xa*, Biochem J. 262, (1989) pp. 651-658.

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

* cited by examiner

POLY(ESTER AMIDES) FOR THE CONTROL OF AGENT-RELEASE FROM POLYMERIC COMPOSITIONS

CROSS REFERENCE TO RELATED APPLICATIONS

This is a continuation application of U.S. application Ser. No. 11/187,467, filed on Jul. 22, 2005, now abandoned which is:

a continuation-in-part of application Ser. No. 10/835,656, filed Apr. 30, 2004 now U.S. Pat. No. 7,820,732;

a continuation-in-part of application Ser. No. 10/855,294, filed May 26, 2004 now abandoned;

a continuation-in-part of application Ser. No. 11/115,631, filed Apr. 26, 2005 now abandoned; and a continuation-in-part of application Ser. No. 11/119,020, filed Apr. 29, 2005 now abandoned;

each application of which is hereby incorporated herein by reference.

BACKGROUND

1. Field of the Invention

This invention is directed to the polymeric matrices that include poly(ester amides) to control the release profiles of agents from within these matrices.

2. Description of the State of the Art

Biomaterial research scientists are striving to improve the compositions from which medical devices and coatings are produced. For example, the control of protein adsorption on an implant surface and the local administration of agents from an implant are areas of focus in biomaterials research. Uncontrolled protein adsorption on an implant surface, for example, leads to a mixed layer of partially denatured proteins on the implant surface. This mixed layer of partially denatured proteins can lead to disease by providing cell-binding sites from adsorbed plasma proteins such as fibrinogen and immunoglobulin G. Platelets and inflammatory cells such as, for example, monocytes, macrophages and neutrophils, adhere to the cell-binding sites. A wide variety of proinflammatory and proliferative factors may be secreted and result in a diseased state. Accordingly, a non-fouling surface, which is a surface that does not become fouled or becomes less fouled with this layer of partially denatured proteins, is desirable.

A stent is an example of an implant that can benefit from improvements such as, for example, a non-fouling surface and a coating that can be used as a vehicle for delivering pharmaceutically active agents in a predictable manner. Stents can act as a mechanical intervention to physically hold open and, if desired, expand a passageway within a subject. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens such as, for example, the lumen of a coronary artery.

Improvements to stents are also being developed to provide a controlled, local delivery of agents. Local delivery of agents is often preferred over systemic delivery of agents, particularly where high systemic doses are necessary to achieve an effect at a particular site within a subject—high systemic doses of agents can often create adverse effects within the subject. One proposed method of local delivery includes coating the surface of a medical article with a polymeric carrier and attaching an agent to, or blending it with, the polymeric carrier.

Agent-coated stents have demonstrated dramatic reductions in the rates of stent restenosis by inhibiting tissue growth associated with the restenosis. Restenosis is a complex biological process and agents have been applied in combination in an attempt to circumvent the process of restenosis. One method of applying multiple agents involves blending the agents together in one formulation and applying the blend to the surface of a stent in a polymer matrix. A disadvantage of this method is that the agents are released from the matrix through the blend and compete with one another for release.

The process of restenosis in coronary artery disease is derived from a complex interplay of several implant-centered biological parameters. These are thought to be the combination of elastic recoil, vascular remodeling, and neo-intimal hyperplasia. Since restenosis is a multifactorial phenomenon, the local agent delivery of agents from a stent would benefit from the design of a release rate profile that would deliver agents as needed from the stent in a controlled and predictable manner.

Stents are used in the treatment and ameliorization of symptoms of other disorders that include, but are not limited to, tumors in organs such as, for example, bile ducts, esophagus, trachea/bronchi, benign pancreatic disease, coronary artery disease, carotid artery disease, and peripheral arterial disease. Peripheral arterial diseases include, but are not limited to, atherosclerosis, restenosis and vulnerable plaque. Vulnerable plaque is a type of fatty build-up in an artery thought to be caused by inflammation and is covered by a thin fibrous cap that can rupture leading to blood clot formation. The treatment of these and other conditions can benefit from localized delivery of an agent.

Unfortunately, the art has not yet developed a reliable way to control the release of agents from a medical device or coating, yet such control can be important to obtaining the desired effects or reducing any adverse effects that may otherwise occur from administration of the agents. In addition to providing a way to improve, for example, the therapeutic and diagnostic results currently obtained from the administration of agents, control over the release of agents can assist in designing and maintaining the physical and mechanical properties of medical devices and coatings as well. Accordingly, control over the release of agents is an important design consideration and one of the next hallmarks in the development of stent technology.

SUMMARY

The embodiments of the present invention generally encompass a medical article, such as a medical device or coating comprising an agent or combination of agents, wherein the agent is distributed throughout a polymeric matrix. In some embodiments, the medical article comprises a stent or a coating for a stent. In some embodiments, the present invention can be a medical article that can comprise a combination of agents and a polymeric matrix. The polymeric matrix comprises an agent and a poly(ester amide) having a design that was preselected to provide a predetermined release rate of the combination of agents from the medical article. The design provides a predetermined diffusion coefficient, a predetermined rate of degradation of the polymeric matrix, or a combination thereof.

In some embodiments, the present invention can be a method of creating a medical article comprising selecting a combination of agents and a predetermined release rate for an agent. The method includes designing a polymeric matrix comprising a poly(ester amide) having a design that was preselected to provide a predetermined release rate of the combination of agents from the medical article. The design provides a predetermined diffusion coefficient, a predetermined rate of degradation of the polymeric matrix, or a combination thereof. The method includes forming the medical article.

In some embodiments, the present invention can include a method of delivering a combination of agents to a mammalian tissue such as vascular tissue. The invention can be used to treat vascular disease, such as restenosis, vulnerable plaque, or a combination thereof.

DETAILED DESCRIPTION

Figure 1:
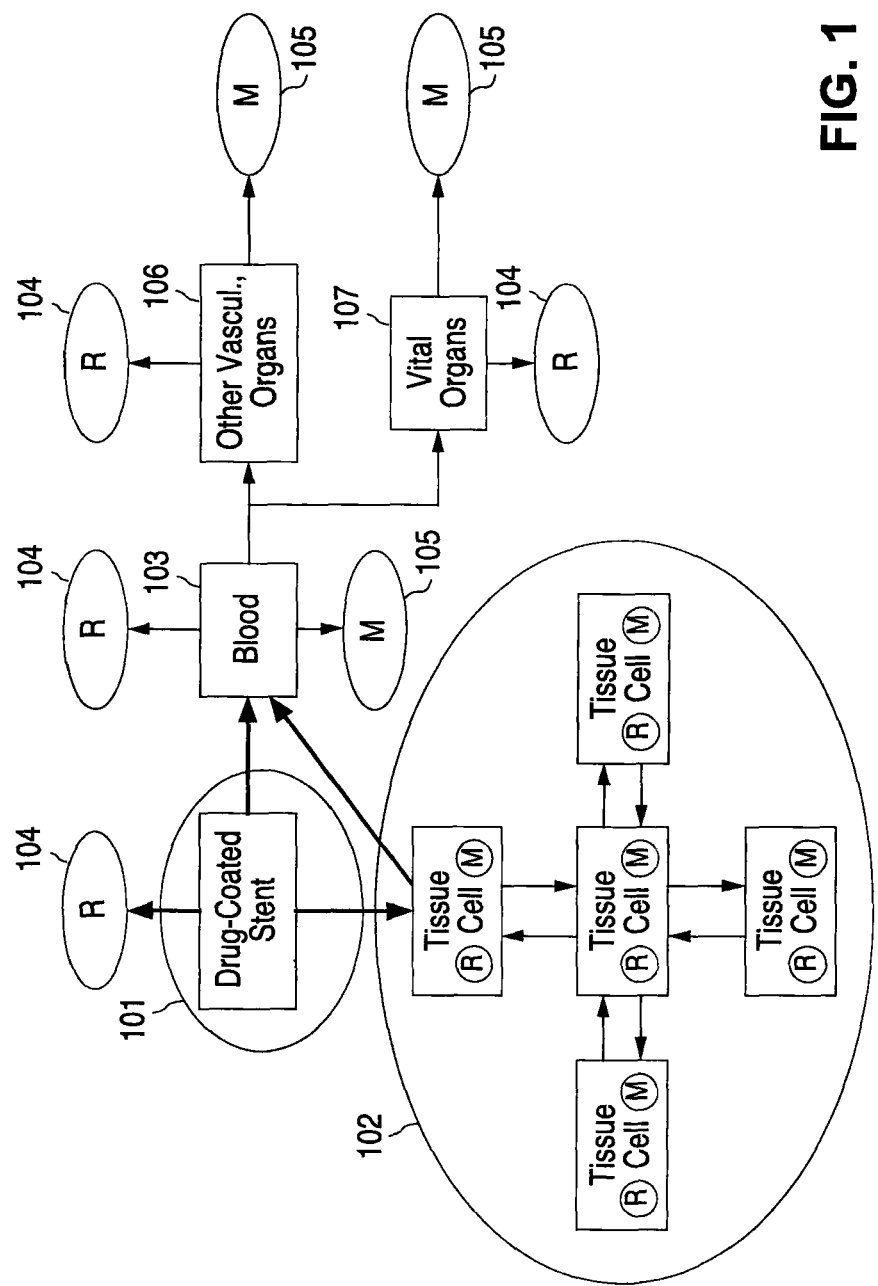
FIG. 1 is a diagram used to illustrate the local pharmacokinetics of agent release from a stent and its subsequent uptake in the coronary vasculature according to some embodiments of the present invention.

As discussed in more detail below, the embodiments of the present invention generally encompass the control of the release of agents from a polymeric matrix that can be used in the formation of a medical article. A "medical article" can include, but is not limited to, a medical device or a coating for a medical device such as, for example, a stent. This control over the release of agents provides for control over, inter alia, the therapeutic, prophylactic, diagnostic, and ameliorative effects that are realized by a patient in need of such treatment. In addition, the control of the release of agents also has an effect upon the mechanical integrity of the polymeric matrix, as well as a relationship to a subject's absorption rate of the absorbable polymers.

The compositions and methods of the present invention apply to the formation of medical devices and coatings. Next generation medical devices and coatings can be designed to target patients, for example, that may not respond as well to current medical devices and coatings. For example, current drug-eluting stents are single agent systems that may not perform as well in patients with diabetes or diffuse, multi-vessel disease. For these types of patients, a combination agent delivery may be more effective, since release rates may need to be different for each of the agents released. Current drug-eluting stents are comprised of polymers that are fairly inert to chemical modifications, such that control over agent release is limited to varying the agent:polymer ratio and optionally applying a polymer topcoat.

Poly(ester amide) (PEA) constructs can be used in the formation of medical devices and coatings. PEA-based polymers can be constructed in a variety of ways and, thus, offer additional degrees of freedom that can be used to control agent release rates. This is important as we are trying to develop medical devices and coatings with additional properties, such as a pro-healing property, which may necessitate the use of multiple drugs and/or the incorporation of peptides/proteins, etc.

In some embodiments, poly(ester amide)-based polymers can be constructed to control the release of a single agent or a combination of agents. In some examples, each agent within the combination of agents can be delivered from such a polymer at a rate that is the same, substantially the same, or substantially different from the rate of release of the other agents. An "agent" can be a moiety that may be bioactive, biobeneficial, diagnostic, plasticizing, or have a combination of these characteristics. For example, an agent can be a drug. A "moiety" can be a functional group composed of at least 1 atom, a bonded residue in a macromolecule, an individual unit in a copolymer or an entire polymeric block. It is to be appreciated that any medical devices that can be improved through the teachings described herein are within the scope of the present invention.

Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (AXIUS™, Guidant Corp.), vena cava filters, and endocardial leads (FINELINE® and ENDOTAK®, Guidant Corp.).

In some embodiments, the stents include, but are not limited to, tubular stents, self-expanding stents, coil stents, ring stents, multi-design stents, and the like. In other embodiments, the stents are metallic; low-ferromagnetic; non-ferromagnetic; biostable polymeric; biodegradable polymeric or biodegradable metallic. In some embodiments, the stents include, but are not limited to, vascular stents, renal stents, biliary stents, pulmonary stents and gastrointestinal stents.

The medical devices can be comprised of a metal or an alloy, including, but not limited to, ELASTINITE® (Guidant Corp.), NITINOL® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

Generally speaking, there are numerous considerations in the release of agents from a polymeric matrix including, but not limited to, the selection and characteristics of (1) polymers and polymer combinations that form the polymeric matrix; (2) the functional groups that are present on polymers in the matrix; (3) the selection of agents to combine with the polymers in a matrix; (4) the polymorphism of the agents; the morphology of the polymeric matrix; (5) the hydrophilicity/hydrophobicity of the polymeric matrix; and (6) the process considerations selected for each step in the process such as, for example, the temperature, pressure, humidity, solvent selection, etc.

The process conditions include, but are not limited to, those that exist in forming the compositions, forming the medical devices or coatings from the compositions, drying conditions, annealing conditions, and the like. The manner in which the agents are combined with the polymers can also have a profound effect such as, for example, whether the agents are bonded, blended, or a combination thereof, with the polymers. Interactions between the agents, polymers, and solvents can also affect the release profile of the agents.

A variety of factors can affect the release of agents from a polymeric matrix. These factors include, but are not limited to, the glass-transition temperature of the polymeric matrix or a component of the polymeric matrix; the manner in which the agents are combined with the polymeric matrix such as, for example, whether the agents are bonded, blended, or a combination thereof, with the polymeric matrix; the lability of the bond between an agent and the polymeric matrix or a bond within a linker between the agent and the polymeric matrix; the solubility of the agent within the polymeric matrix; and the rate at which the polymeric matrix degrades.

FIG. 1 is a diagram used to illustrate the local pharmacokinetics of agent release from a stent and its subsequent uptake in the coronary vasculature according to some embodiments of the present invention. In region 101, the agent that will be released from the stent is a drug. The agent can be released and passed through tissue cells within adjoining tissue 102, blood 103, or the agent can remain as residual agent ("R") 104 on the stent. The agent can also be metabolized ("M") 105 after its delivery to adjoining tissue 102, blood 103, other vascular organs 106, or vital organs 107.

Design of Release Rates

Figure 2:
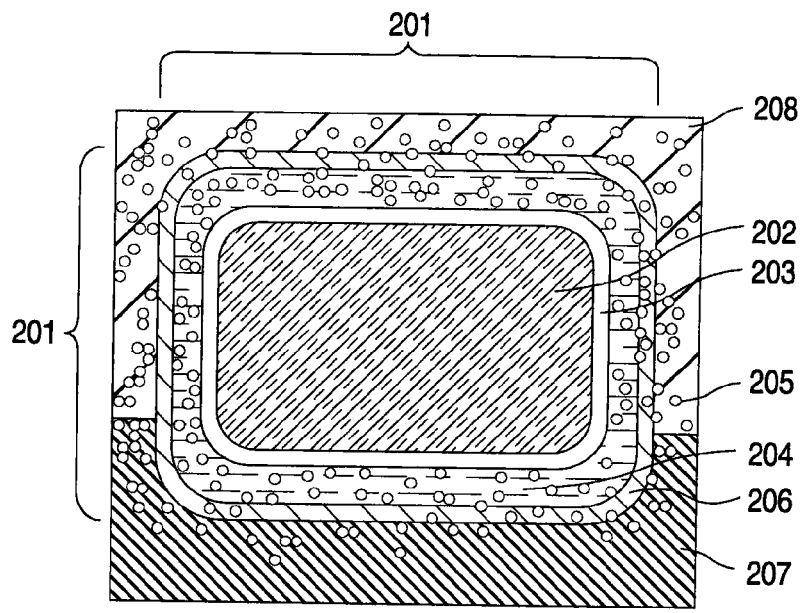
FIG. 2 illustrates a cross-section of a coating on a stent strut within a vascular organ according to some embodiments of the present invention.

FIG. 2 illustrates a cross-section of a coating on a stent strut within a vascular organ according to some embodiments of the present invention. The cross-section of the coated stent strut 201 includes a stent 202, an optional primer layer 203, a polymer reservoir 204 that includes at least one agent 205, and an optional top-coat layer 206 that can further control the diffusion of the agent 205 out of the polymer reservoir 204. The coated stent strut 201 is adjoining vascular tissue 207 and blood 208. The agent 205 is released from the polymer reservoir 204 into the blood 208 and the vascular tissue 207. This release of the agent 205 includes a diffusion parameter, so design of a polymeric matrix can include diffusion considerations in order to further obtain control over the release of the agent 205.

Diffusion Coefficients

In many embodiments, the release of an agent within a polymeric matrix can include diffusion of the agent across the polymeric matrix prior to release of the agent within a subject. The process of diffusion of an agent from a medical article such as, for example, a medical device or coating, can be affected by factors that include, but are not limited to, the following four factors: (1) coating parameters, (2) coating process, (3) polymer physicochemical properties, (4) agent physicochemical properties, and any combination thereof.

The coating parameters include, but are not limited to, the initial solid phase concentration distribution, which includes the drug to polymer (D/P) ratio, the thickness of an agent-free polymer top-coating, the total drug content, the dispersed phase microstructure, porosity, the type and amount of other components present, and the like. The coating process includes, but is not limited to, the selection of solvents, the thermal history of processing, the thermodynamics of phase separation, the solution thermodynamics, kinetics, and the like.

Polymer physicochemical properties include, but are not limited to, glass transition temperature (Tg), melting temperature (Tm), heat of fusion ($\Delta H_f$), percent crystallinity, water absorption, lipid-induced swelling, and the like. Agent physicochemical properties include, but are not limited to, the degree and type of dispersed phase parameters, the extent of solid solution, the polymorphism of the agent (e.g. different crystalline forms of a drug), and the like.

Diffusion will occur wherever there is a diffusion medium such as, for example, the water that is taken up by a coating layer on a stent while implanted in a vascular organ. A mathematical expression is provided below to describe diffusion of an agent across a coating layer, where the driving force is the concentration gradient of the agent across the diffusion medium. The flux of the agent across the diffusion medium can be represented by the following formula:

$$F = -D\frac{dC}{dx}, \text{ where} \quad (1)$$

$$D = \text{diffusion coefficient} \left(\frac{L^2}{t}\right);$$

$$F = \text{agent flux} \left(\frac{\text{moles}}{L^2 * t}\right);$$

$\frac{dC}{dx}$ = concentration gradient, i.e., change in concentration/change in distance across the layer $\left(\frac{\text{moles}}{L^4}\right)$;

$L$ = any unit of layer dimension used, e.g., to calculate area or thickness; and $t$ = time.

As the agent travels through the coating layer, the flux of the agent changes with the concentration gradient. Starting from the general mass balance, Input−Output+Generation=Accumulation, or $$M_i - M_o + M_g = -D\frac{dCi}{dx} - -D\frac{dCo}{dx} \quad (2)$$

Using the mathematical relationship that $$y_x - y_{x+dx} = \frac{dy}{dx}dx,$$

and assuming a constant diffusivity across the polymeric matrix of the coating layer, the relationship becomes $$\frac{dM}{dx}dx + M_g = -D\frac{d^2C}{dx^2}dx. \quad (3)$$

Since there is no generation of agent in the coating layer, $M_g$=0. Therefore, $$\frac{dM}{dx} = -D\frac{d^2C}{dx^2};$$

and since accumulation = $\frac{dC}{dt}$, the equation becomes Fick's Second Law:

$$\frac{dC}{dt} = -D\frac{d^2C}{dx^2}. \quad (4)$$

Fick's Second Law tells us that the change in the concentration of the agent over time is equal to the change in the local flux of the agent. This provides a means to assess the rate of release of agents within particular polymeric matrix systems, wherein each system can have a number of factors that affect this rate of release. These factors have been presented above, and the net result of the combined diffusion-related factors within a given system can be cumulatively expressed as a diffusion coefficient. The diffusion coefficient can also be described as "effective-diffusion coefficient" for describing a particular system.

Without intending to be bound by any theory or mechanism of action, the diffusive transport of an agent can be divided into at least two modes referred to as "biphasic modes:"

(1) in a first mode, the effective diffusivity corresponds to the transport of an agent dissolved in a polymeric matrix without phase separation; or, an agent that primarily transports out of a dispersed agent phase into a surrounding polymeric matrix and then diffuses out of the surrounding polymeric matrix; and, (2) in a second mode, the effective diffusivity corresponds to the transport of an agent through a dispersed agent phase, for example, a dispersed agent phase within a polymeric matrix that has interconnected to create a closely connected network (i.e. a "percolated" phase, which is discussed in more detail below) by virtue of being densely distributed throughout the polymeric matrix; accordingly, the effective diffusivity can include an intrinsic diffusivity of the agent through a water medium in the polymeric matrix in addition to the tortuosity and porosity of a percolated-phase passage that has formed throughout the polymeric matrix.

In some embodiments, the overall mass transport can be considered dependent on one or a combination of the biphasic modes. Since the diffusion coefficient can be directly proportional to the rate of release, it can be measured experimentally for each polymeric matrix system by one skilled in the art and used as a defining characteristic for agent release from within that system.

The derivation of Fick's Second Law provides some reasoning for an assumption that the diffusion-based flux of agents from a medical device or coating, i.e. diffusion-based release rate, may be controlled through the design of the polymeric matrix used in the formation of the medical device or coating. Using such an assumption, a method of designing polymeric matrices having particular poly(ester amide) designs has been investigated as a way to predictably deliver agents in vivo from compositions used to form medical devices or coatings.

Effect of Coating Morphology on Diffusion Coefficients

The behavior of the components in a polymeric composition during the formation of a polymeric matrix depends, at least in part, on the thermodynamic relationships between the components in the composition. These relationships include, for example, the thermodynamics between the agents, the polymers, the solvents, and any combination thereof. The thermodynamic relationships between the components affect the manner which local concentration of an agent, for example, modifies the coating morphology that results from the process used in the formation of the polymeric matrix. Accordingly, control over the coating morphology provides some control over the release rate of the agent.

In many embodiments, the polymeric matrix can include a combination of polymers. In some embodiments, an agent can be more thermodynamically stable when combined with a first polymer than a second polymer and, thus, preferentially dissolve in the first polymer. A first polymer/agent combination forms as a dispersed phase that can be substantially or completely immiscible with the second polymer. In these embodiments, the second polymer can be referred to as a "bulk phase," and the first polymer/agent combination can be referred to as an "agent-enriched phase."

In some embodiments, a solvent can be selected, such that the solubility of an agent in the solvent is thermodynamically more favorable than the solubility of a first polymer in the solvent. The solvent can be selected such that a combination of the solvent and a second polymer is thermodynamically more favorable than a combination of the solvent with the first polymer. In these embodiments, an agent that ordinarily would preferentially dissolve in a first polymer can become preferentially incorporated in a second-polymer phase by this component selection. The polymer/solvent/agent system can effectively transport the agent in the solvent during removal of the solvent from the composition to form the polymeric matrix in the medical device or coating. In this manner, the diffusion of the agent can be controlled in some embodiments by selectively placing the agent in a preferred polymeric phase.

In some embodiments, an interconnected agent-enriched dispersed phase provides a means for affecting the diffusion coefficient and controlling the release of agents from a polymeric matrix. In many embodiments, an agent-enriched phase will reach a percolation threshold at a concentration of about 30% by volume within the combined volume of the polymer matrix and agent.

The "percolation threshold" is the point at which the agent-enriched phase begins to connect with itself and form an interconnected three-dimensional network of the agent-enriched phase within the polymeric matrix. The percolation threshold is the point at which the agent-enriched phase forms its own channel for diffusion. In these embodiments, diffusion of an agent can be controlled by placing the agent in an interconnected, agent-rich dispersed phase that is created through selection of process parameters.

In some embodiments, placing an agent in an interconnected, agent-rich dispersed phase can result in a faster release of an agent. In other embodiments, diffusion of an agent through an interconnected, agent-rich dispersed phase can result in a slower release of an agent. In some embodiments, the agent can exist in both the interconnected, agent-enriched dispersed phase and the bulk phase, such that release of the agent occurs through diffusion across both phases.

Figure 3:
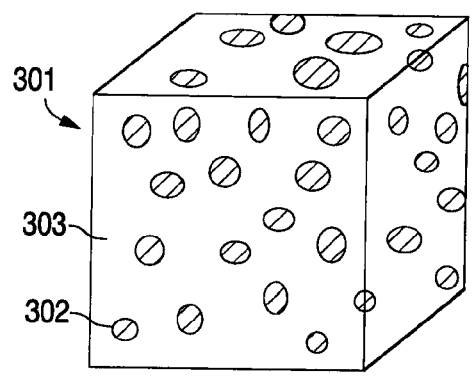
FIG. 3 illustrates a section of a polymeric matrix containing an agent-enriched phase at a concentration that is below about 30% by volume according to some embodiments of the present invention.

FIG. 3 illustrates a section of a polymeric matrix containing an agent-enriched phase at a concentration that is below about 30% by volume according to some embodiments of the present invention. The section 301 of the polymeric matrix is below the percolation threshold, since the agent-enriched phase 302 has not yet reached the concentration required to begin forming an interconnected network within the bulk phase 303 of the polymeric matrix.

Figure 4:
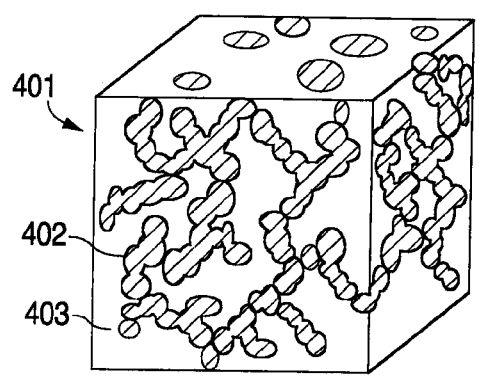
FIG. 4 illustrates a section of a polymeric matrix containing an agent-enriched phase at a concentration that is above about 30% by volume according to some embodiments of the present invention.

FIG. 4 illustrates a section of a polymeric matrix containing an agent-enriched phase at a concentration that is above about 30% by volume according to some embodiments of the present invention. The section 401 of the polymeric matrix is above the percolation threshold, since the agent-enriched phase 402 has reached the concentration required to begin forming an interconnected network within the bulk phase 403 of the polymeric matrix.

In many embodiments, the agents can be dissolved in the polymeric matrix, exist in a dispersed phase within the polymeric matrix, or a combination thereof. In some embodiments, the agent component of a polymeric matrix can dissolve in a polymer phase and form a dispersed phase upon removal of the solvent used to form the composition.

Figure 5A:
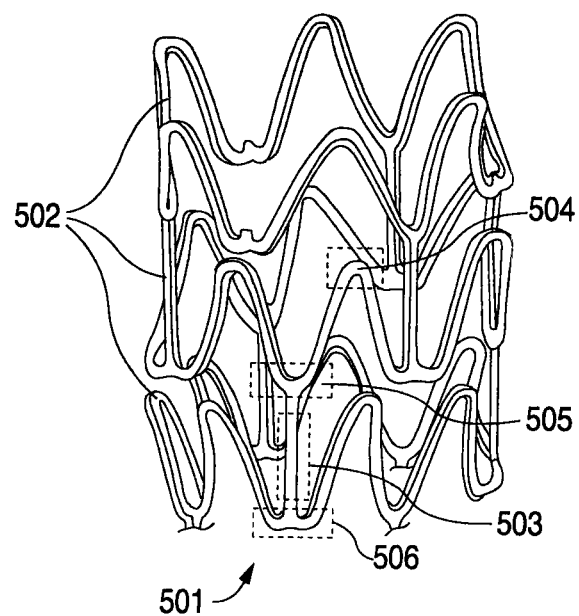
FIGS. 5a and 5b depict (1) an example of a three-dimensional view of a stent and (2) select areas of an abluminal portion of a stent that can be selectively coated with a combination of agents according to some embodiments of the present invention.
Figure 5B:
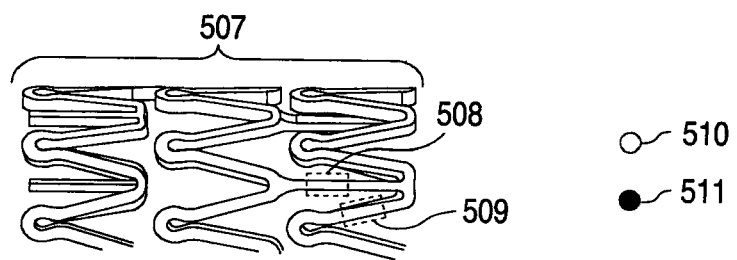

Embodiments of the devices described herein may be illustrated by a stent. FIGS. 5a and 5b depict (1) an example of a three-dimensional view of a stent and (2) select areas of an abluminal portion of a stent that can be selectively coated with a combination of agents according to some embodiments of the present invention. The stent 501 may be made up of a pattern of a number of interconnecting structural elements or struts 502. As described herein, the embodiments disclosed are not limited to stents or to the stent pattern illustrated in FIGS. 5a and 5b and are easily applicable to other patterns and other devices. The variations in the structure of patterns are virtually unlimited.

Designing a poly(ester amide) having a design feature that was preselected to provide a predetermined release rate within the polymeric matrices may also assist in obtaining and maintaining desirable physical and mechanical properties and, thus, aid in preventing failure within medical devices or coatings. Since many medical implants undergo a great deal of strain during their manufacture and use that can result in structural failure, the ability to apply particular polymeric matrices having particular agents to select regions can be invaluable to the success of a medical procedure.

Structural failure can occur, for example, as a result of manipulating an implant in preparation for placing the implant in a subject and while placing the implant in a desired location in a subject. A stent is an example of an implant that may be compressed, inserted into a small vessel through a catheter, and then expanded to a larger diameter in a subject. Controlled application of particular agents in low strain areas 503 and high strain areas 504, 505, and 506 of a stent, for example, can help to avoid problems, such as cracking and flaking, which can occur during implantation of the stent.

In some embodiments, the agent-containing compositions can be applied selectively to an abluminal surface of a medical device such as, for example, a stent. In many embodiments, the stent can be a balloon-expandable stent or a self-expandable stent. The "abluminal" surface can refer to the surface of the device that is directed away from the lumen of the organ in which the device has been deployed. In some embodiments, the lumen can be an arterial lumen. For example, the abluminal surface of a stent comprises the surface of the stent that is placed in contact with the inner wall of an artery.

FIG. 5b illustrates select areas of an abluminal portion of a stent that can be selectively coated with a combination of agents according to some embodiments of the present invention. In this embodiment, a coating composition comprising agent A 510 can be selectively applied to area 508, and a coating composition comprising agent B 511 can be selectively applied to area 509.

The selective application of agents can allow for a controlled release of each agent, in some embodiments, by allowing for the independent selection of the manner in which each agent is attached to a surface of the stent 507. For example, an agent may be combined with a polymer matrix as a blend, a chemical conjugation, or a combination thereof, which affects the rate of release. The agent may also be sandwiched between polymer layers, encapsulated within a polymer network, or any combination thereof, thereby providing a desired agent concentration such as, for example, a desired spike in agent concentration at the boundary of a polymeric matrix.

In some embodiments, a medical device can comprise a polymeric matrix having a predetermined release rate of one or more agents through the application of one or more coating compositions. In other embodiments, a medical device can be coated with a composition comprising a polymeric matrix having a predetermined release rate of one or more agents based on coating configurations comprising one or more select poly(ester amides). In other embodiments, the medical device and coating can each have their own preselected poly (ester amides), such that each poly(ester amide) can be designed to release an agent at a predetermined rate.

In some embodiments, the polymeric matrix can release agents without biodegradation of the matrix, such that the agent-release is at least partially independent of biodegradation. In other embodiments, the polymeric matrix releases agents during biodegradation of the matrix, such that the agent-release design is at least partially dependent on biodegradation. In other examples, the polymeric matrix releases agents according to a combination of poly(ester amide) designs, wherein the combination can provide release rates that are at least partially independent of, or at least partially dependent on, biodegradation of the polymeric matrix.

In some embodiments, the medical device includes a stent, wherein the thickness of the struts that form the structure of the stent can be referred to as a layer or, in some embodiments, a combination of layers. In other embodiments, a layer or combination of layers can be applied as a coating on a surface of a medical device such as, for example, a stent. In other embodiments, the layers can be applied as a coating on select surfaces such as, for example, the abluminal surface of a stent. In other embodiments, the layers can be applied in predetermined geometrical patterns on select surfaces of a medical device such as, for example, a stent.

In other embodiments, a combination of layers can be incrementally formed such as, for example, during the stacking of layers in a layered-manufacturing process, the methods of which are known to those skilled in the art. In a layered-manufacturing process, the object to be manufactured is programmed into the computer as a solid model and the model is "sliced" mathematically using slice algorithms. The information on each slice is then sent to a manufacturing unit which consists of a material delivery and curing system capable of tracing out each layer such as, for example, a vat containing an ultraviolet-curable polymeric material with a rasterizing ultraviolet laser used to trace the shape of each layer. Each layer has an associated thickness and the entire layer has the same cross-section. Once the current layer is ready, the computer sends the information about the next layer to the manufacturing system which builds the next layer of a series of layers, thus building the entire object layer-by-layer.

In other embodiments, each layer can be applied incrementally in controlled volumes such as, for example, through the use of an apparatus that ejects controlled volumes of a polymeric matrix. In some embodiments, the controlled volumes can be droplets, and each droplet may be independently formed and placed on a surface. Each droplet may independently include pure agent, a combination of agents, pure polymer, a combination of polymers, or a combination thereof. Likewise, the agents may be independently selected for each droplet.

Solvent Selection

The formation of the medical devices and coatings of the present invention may require the selection and use of solvents to assist in creating and using the compositions of the present invention. Since many applications of the present invention include "casting" of the compositions, such as the application of a coating on a substrate, the solvents will be referred to as "casting solvents."

The casting solvent used to form medical devices or coatings may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent; the presence of oxygen and other gases in the casting solvent; the viscosity and vapor pressure of the combined casting solvent and polymer; the ability of the casting solvent to diffuse through adjacent materials, such as an underlying material; and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Exemplary casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

Agent release can be affected by the selection of process parameters. The process parameters include, but are not limited to, the selection of the process or combination of processes used to form a medical device or coating, in which the processes can include all of the steps from selection of the components of the composition and forming the composition to applying, forming, drying, and optionally annealing the composition in making a medical device or coating. The following methods are examples of methods that can be used in producing the medical devices and coatings of the present invention. These methods are not intended to be limiting for purposes of the present invention.

Forming a Medical Article

An agent can be localized in an implant during a process of forming the implant, and the localization can be beneficial for a variety of reasons such as, for example, use of less agent in select regions; use of a preferred agent in select regions such as, for example, an agent with desired potency or faster leaching rate; modification of mechanical properties of select regions of an implant; leaching of less agent for elimination by a subject; and combinations thereof. In some embodiments, there may be no agent in the regions outside of the high-strain regions in an implant. In other embodiments, there may be less agent in the regions outside of the high-strain regions in an implant. In embodiments where less agent is desired in the regions outside of the high-strain regions, the amount of agent in the regions outside of the high-strain regions can have 2%, 5%, 10%, 15%, 20%, 30%, 40%, 50%, 60%, 70%, 80%, 90%, 95%, or any range therein, less agent than the high-strain regions.

Processes for forming a medical article include, but are not limited to, casting, molding, coating, and combinations thereof. In some embodiments, the agent-containing compositions can be applied within the process in the form of a controlled volume, such as a droplet. In some embodiments, the implant is formed in a casting process, and the mechanical properties of the high-strain regions of the implant are controlled by concentrating the agent in the high-strain regions, by using different agents in the high-strain regions, by using agents only in the high-strain regions, or a combination thereof. Casting an implant involves pouring a liquid polymeric composition into a mold. In one embodiment, the localization of an agent in an implant during such casting can be obtained by varying the amount and/or type of agent in the polymeric composition during pouring as desired such that the agent becomes localized in the formed implant.

In other embodiments, the implant is formed in a molding process, which includes, but is not limited to, compression molding, extrusion molding, injection molding, and foam molding. The mechanical properties of the high-strain regions of the implant are controlled by concentrating the agent in the high-strain regions, by using different agents in the high-strain regions, by using agents only in the high-strain regions, or a combination thereof.

In compression molding, solid polymeric materials are added to a mold and pressure and heat are applied until the polymeric material conforms to the mold. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of agents in an implant during such compression molding can be obtained by varying the amount and/or type of agent in the solid polymeric materials while adding the solid polymeric materials to the mold as desired such that the agent becomes localized in the formed implant.

In extrusion molding, solid polymeric materials are added to a continuous melt that is forced through a die and cooled to a solid form. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of agent in an implant during such extrusion molding can be obtained by varying the amount and/or type of agent in the solid polymeric materials while adding the solid polymeric materials to the extrusion mold as desired such that the agent becomes localized in the formed implant.

In injection molding, solid polymeric materials are added to a heated cylinder, softened and forced into a mold under pressure to create a solid form. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of agent in an implant during such injection molding can be obtained by varying the amount and/or type of agent in the solid polymeric materials while adding the solid polymeric materials to the injection mold as desired such that the agent becomes localized in the formed implant.

In foam molding, blowing agents are used to expand and mold solid polymeric materials into a desired form, and the solid polymeric materials can be expanded to a volume ranging from about two to about 50 times their original volume. The polymeric material can be pre-expanded using steam and air and then formed in a mold with additional steam; or mixed with a gas to form a polymer/gas mixture that is forced into a mold of lower pressure. The solid form may require additional processing to obtain the final product in a desired form. The solid polymeric materials can be in the form of particles that can vary in mean diameter from about 1 nm to about 1 cm, from about 1 nm to about 10 mm, from about 1 mm to about 1 mm, from about 1 nm to about 100 nm, or any range therein. In one embodiment, the localization of agent in an implant during such foam molding can be obtained by varying the amount and/or type of agent in the solid polymeric materials while adding the solid polymeric materials to the foam mold as desired such that the agent becomes localized in the formed implant.

In other embodiments, a stent is formed by injection molding or extrusion of a tube followed by cutting a pattern of a stent into the tube. In one example, the pattern can be cut with a laser. In these embodiments, for example, a mixture of polymer and agent can be added prior to injection molding or extrusion or, in the alternative, the agent can be absorbed by the stent after the stent has been formed.

Forming a Layer

In each of the embodiments, the term "layer" describes a thickness of a polymeric matrix within which an agent must pass through to be released into a subject. This term can refer, for example, to any individual polymeric matrix that may be used to form a medical device or a coating for a medical device. A layer can include, but is not limited to, polymeric material from a single-pass application or multiple-pass application, where a "pass" can be any single process step, or combination of steps, used to apply a material such as, for example, a pass of a spray coating device, a pass of an electrostatic coating device, a pass of a controlled-volume ejector, a dipping, an extrusion, a mold, a single dip in a layered manufacturing process, or a combination thereof. In general, a pass includes any single process step known to one of skill in the art that can be used to apply materials in the formation of a medical device or coating using a composition comprising a polymeric material. A layer can consist of a single pass or multiple passes. In some embodiments, the coating can be applied to an entire medical device or select regions of the medical device.

The term "thickness" can refer to the distance between opposite surfaces of a polymeric matrix that is used in the production of a medical device or coating. The thickness can refer to that of a single layer, a single layer within a combination of layers, or a combination layers.

In some embodiments, the thickness of a polymeric matrix can be the thickness of a component within the structure of a medical device, such as, for example, the thickness of a strut within a stent. In other embodiments, the thickness of a polymeric matrix can be the thickness of a layer of coating applied to a medical device. In other embodiments, the thickness of a polymeric matrix can be the thickness of a combination of layers applied as a coating for a medical device.

In many embodiments, the thickness of a polymeric matrix can range from about 0.1 nm to about 1.0 cm, from about 0.1 nm to about 1.0 mm, from about 0.1 nm to about 100 µm, from about 0.1 nm to about 1 µm, from about 0.1 nm to about 100 nm, from about 0.1 nm to about 10 nm, from about 10 nm to about 100 nm, from about 10 µm to about 50 µm, from about 50 µm to about 100 µm, or any range therein. In other embodiments, the thickness of a polymeric matrix can range from about 1 µm to about 10 µm, which can be found, for example, in some of the current drug-eluting stent (DES) systems. In other embodiments, the thickness of the polymeric matrices can be regionally distributed throughout a device to create a variation in thicknesses such as, for example, the variation in thicknesses that can be found in an abluminally-coated DES stent.

In some embodiments of the invention, the compositions are in the form of coatings for medical devices such as, for example, a balloon-expandable stent or a self-expanding stent. There are many coating configurations within the scope of the present invention, and each configuration can include any number and combination of layers. In some embodiments, the coatings of the present invention can comprise one or a combination of the following four types of layers:

(a) an agent layer, which may comprise a polymer and an agent or, alternatively, a polymer free agent;

(b) an optional primer layer, which may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

In many embodiments, each layer can be applied to an implantable substrate by any method including, but not limited to, dipping, spraying, pouring, brushing, spin-coating, roller coating, meniscus coating, powder coating, inkjet-type application, controlled-volume application such as drop-on-demand, or a combination thereof. In these embodiments, a dry coating containing a biodegradable polymer may be formed on the stent when the solvent evaporates. In some embodiments, at least one of the layers can be formed on a stent by dissolving one or more biodegradable polymers, optionally with a non-biodegradable polymer, in one or more solvents, and either (i) spraying the solution on the stent or (ii) dipping the stent in the solution.

In other embodiments, a coating can be applied to a medical device, such as a stent, using methods that may include sputtering and gas-phase polymerization. Sputtering is a method that includes placing a polymeric material target in an environment that is conducive to applying energy to the polymeric material and sputtering the polymeric material from the target to the device to form a coating of the polymeric material on the device. Similarly, a gas-phase polymerization method includes applying energy to a monomer in the gas phase within an environment that is conducive to formation of a polymer from the monomer in the gas phase, and wherein the polymer formed coats the device.

In some embodiments, a pure agent can be applied directly to at least a part of an implantable substrate as a layer to serve as a reservoir for at least one bioactive agent. In another embodiment, the agent can be combined with a polymer. In another embodiment, an optional primer layer can be applied between the implantable substrate and the agent layer to improve adhesion of the agent layer to the implantable substrate and can optionally comprise an agent.

In other embodiments, a pure agent layer can be sandwiched between layers comprising biodegradable polymer. In other embodiments, the optional topcoat layer can be applied over at least a portion of the agent layer to serve as a topcoat to assist in the control the rate of release of agents and can optionally comprise an agent. In another embodiment, a biocompatible finishing layer can be applied to increase the biocompatibility of the coating by, for example, increasing acute hemocompatibility, and this layer can also comprise an agent.

Forming Polymeric Matrix Configurations

The rate of release of an agent from a composition depends on the materials that are selected for use in the formation the compositions, as well as the processes that are selected for use in the formation of the polymeric matrices from the compositions. The polymeric matrices taught herein can be, for example, a ternary system having an agent, polymer, and solvent; and as described herein, the relationship between the elements in this ternary system can affect the coating configurations obtained within the polymeric matrices.

As described above, Fick's Second Law tells us that the change in the concentration of the agent over time is equal to the change in the local flux of the agent. Accordingly, although each polymeric matrix can have a number of factors that affect this rate of release, it can be assumed that the rate of release of agents within particular polymeric matrix system can be controlled by the design of an initial concentration gradient profile (IC profile) of an agent across the polymeric matrix. In some embodiments, virtually any IC profile or combination of IC profiles that represent a desired agent release can be produced by design across a polymeric matrix in a medical device or a coating for a medical device. The use of a mathematical function provides a way to characterize a desired IC profile in the illustration and design of a process for creating desired IC profiles according to some embodiments of the present invention. The variety of initial concentration profiles that may be desired or may be designed is virtually limitless.

FIGS. 6a-6d illustrates initial concentration gradient profiles in a polymeric matrix according to some embodiments of the present invention. In FIGS. 6a-6d, the IC profile 601 begins at a boundary 602 at the surface 603 of a medical device and ends at a boundary 604 between the polymeric matrix 605 and an optional topcoat 606. In each of FIGS. 6a-6d, the profiles represent a correlation between the agent concentration on the y-axis and the position of the agent as measured from the boundary 602 of the surface 603 of the medical device on the x-axis.

Figure 6A:
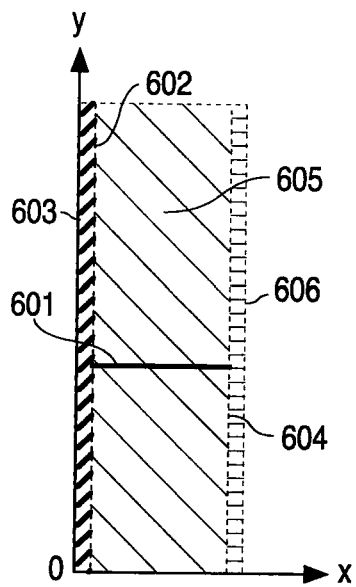
FIGS. 6a-6d illustrates initial concentration gradient profiles in a polymeric matrix according to some embodiments of the present invention.
Figure 6B:
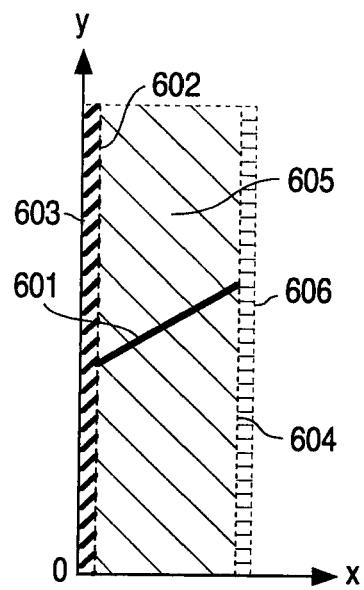
Figure 6C:
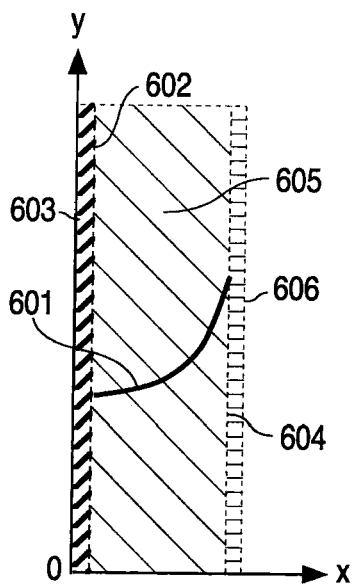
Figure 6D:
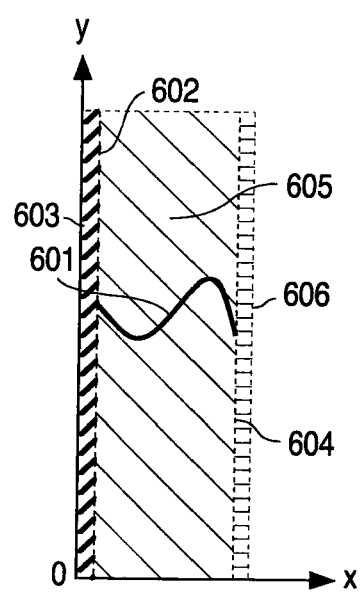

In FIG. 6a, the IC profile 601 is a linear profile, wherein the agent concentration is a zero order function of position in the polymeric matrix, and is a constant in this case. In FIG. 6b, the IC profile 601 is a linear profile, wherein the agent concentration is a first order function of position in the polymeric matrix. In FIG. 6c, the IC profile 601 is a non-linear profile, wherein the agent concentration is an exponential function of position in the polymeric matrix. In FIG. 6d, the IC profile 601 is a non-linear profile, wherein the agent concentration is a wave function of position in the polymeric matrix.

In some embodiments, a coating configuration can be affected by the relative hydrophobicity and hydrophilicity of the components in a given polymeric matrix. Another factor that should be considered in developing a coating configuration is the selection of boundary conditions that can be present during processing of a polymeric matrix used in a medical device or coating. The boundary conditions are a factor to consider in that a variety of boundary conditions can create a variety of morphologies within a polymeric matrix, and control of the morphologies can assist in the control of agent release.

Boundary conditions are another set of variables that can be varied at each step in the process of forming a medical device or coating and include, but are not limited to, pressure, temperature, and atmosphere, wherein the atmosphere can include, but is not limited to, relative humidity, solvent vapor, or a combination thereof. Because of these boundary considerations, process applications such as the application of an external pressure, temperature, or a combination thereof such as, for example, freeze-drying can alter the distribution of agent within a polymeric matrix and serve as a means to design a coating configuration, for example, a predetermined IC profile for a desired release rate of an agent.

The compositions of the present invention can be used for one or any combination of layers. In some embodiments, any of the polymers taught herein can be used as a layer within a coating or can be blended or crosslinked with any of the compositions taught herein. In some embodiments, a layer may comprise one or more coating configurations including, but not limited to, an IC profile, a morphology that was created by the selection of boundary conditions, a poly(ester amide) designed to control diffusion, a poly(ester amide) designed to control degradation, or a combination thereof. In some embodiments, the coating configurations may include, for example, selectively-placed agents within a desired IC profile at a predetermined region on a medical device or within a coating.

In some embodiments, the methods of the present invention can be used to coat a medical device with layers formed from polymeric matrices having more than one coating configuration. In some embodiments, the coating configurations can include a pure agent as a layer within a combination of layers, for example, such that the IC profile represents a maximum agent concentration.

Figure 7A:
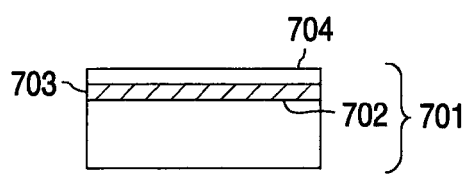
FIGS. 7a and 7b illustrate a sandwiched-coating design according to some embodiments of the present invention.
Figure 7B:
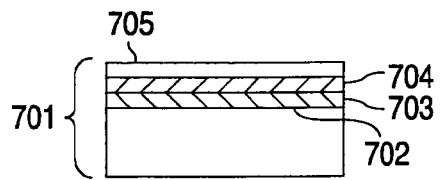

FIGS. 7a and 7b illustrate a sandwiched-coating design according to some embodiments of the present invention. FIG. 7a illustrates a cross-section of a stent strut 701 in which the abluminal surface 702 includes a first layer 703 containing agent B applied to the abluminal surface 702 and a second layer 704 containing agent A applied on the first layer 703 containing agent B. Each of the layers can be formed by any method known to one of skill in the art including, but not limited to, any one or any combination of the methods described above, and the layers can be applied to the entire stent or select regions of the stent.

In some embodiments, the first layer 703 can have a coating configuration that is different from a coating configuration in the second layer 704, such that agents A and B are delivered at different release rates, wherein the assumption can be that the difference between diffusion coefficients of the first layer 703 and second layer 704 is negligible. FIG. 7b illustrates a cross-section of the stent strut 701 in which the first layer 703 and the second layer 704 are coated by a third layer 705. The third layer 705 can contain any composition taught herein such as, for example, a topcoat to assist in controlling the rate of release of the agents, act as a biobeneficial layer, deliver one or more agents, or a combination thereof.

In some embodiments, each layer within the combination of layers can have a unique IC profile for each of the one or more agents, such that the combination of layers provides a controlled delivery of the one or more agents in a subject. In other embodiments, the combination of layers provides a step-by-step gradient of IC profiles, the sum of which provides an overall IC profile of one or more agents within a medical device, coating, or a combination thereof.

Figure 8:
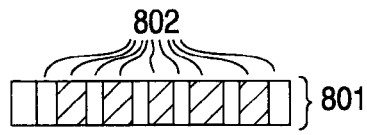
FIG. 8 illustrates a checkerboard-type coating design by showing a top view of an abluminal surface of a stent that was coated in sections according to some embodiments of the present invention.

FIG. 8 illustrates a checkerboard-type coating design by showing a top view of an abluminal surface of a stent that was coated in sections according to some embodiments of the present invention. The process of coating the abluminal surface 801 of the stent in sections 802 can occur simultaneously or as a series of coating steps. Each section 802 of the checkerboard-type coating design can have a unique configuration for controlled release of one or more agents.

In one example, each of the sections 802 can contain a single agent, more than one agent, or a combination thereof. In another example, each section 802 can contain a coating configuration that is similar or equal to the other sections 802. In another example, each section 802 contains a coating configuration that is tailored to deliver a particular agent from a select region of a medical device such as, for example, a stent. In another example, each section 802 contains a coating configuration that is similar to adjacent sections 802, but the release rate of agents can vary due to a variation in diffusion coefficients, for example, as a result of adding a biodegradable polymer in the polymeric matrix. In another example, each section 802 has a similar or equal thickness. In another example, each section 802 can vary in thickness due to any one or any combination of the above factors. The coating configurations can be developed using any method taught herein.

Figure 9A:
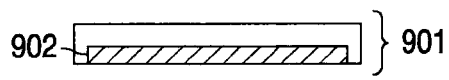
FIGS. 9a and 9b illustrate an engraved-type coating design by showing a top view of the abluminal surface of a stent with engravings according to some embodiments of the present invention.
Figure 9B:
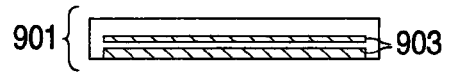

FIGS. 9a and 9b illustrate an engraved-type coating design by showing a top view of the abluminal surface of a stent with engravings according to some embodiments of the present invention. The engravings can be in any shape, size or form such as, for example, channels or pits. FIG. 9a shows a single channel 902 on the abluminal surface 901 of the stent, and FIG. 9b shows a parallel track-type coating design 903 on the abluminal surface 901 of the stent.

In some embodiments, a channel width can range from about 0.0005 inches to about 0.005 inches. In other embodiments, the channel width can range from about 0.001 inches to about 0.004 inches. In other embodiments, the channel width can range from about 0.001 inches to about 0.002 inches. In other embodiments, there can be a single pit. In other embodiments, the engravings can be continuous on the abluminal surface on each strut of the stent such as, for example, a continuous channel. In other embodiments, the engravings can be discontinuous and placed in select regions on the abluminal surface of the stent. In other embodiments, the stent can have a combination of any shape engravings such as, for example, a combination of channels and pits. The pits and channels can be formed using any method known to one of skill in the art such as, for example, laser cutting, extruding, or molding.

The compositions described above can all include controlled volumes of agents, agents blended and/or conjugated with a polymer, agents encapsulated with a polymer, or a combination thereof, according to some embodiments of the present invention. These controlled volumes can be formed using any method known to one of skill in the art including, for example, methods that dispense droplets with a nozzle and methods that do not require a nozzle to dispense droplets. The methods that dispense droplets with a nozzle can include any source of pressure known to one of skill in the art.

Figure 10A:
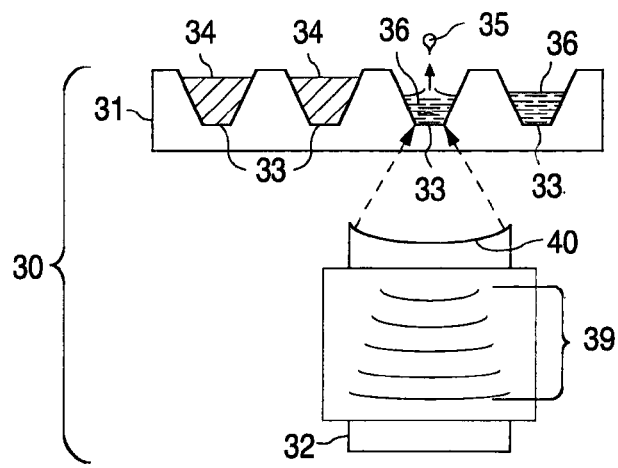
FIGS. 10a and 10b illustrate an ejector assembly that does not require a nozzle, according to some embodiments of the present invention.
Figure 10B:
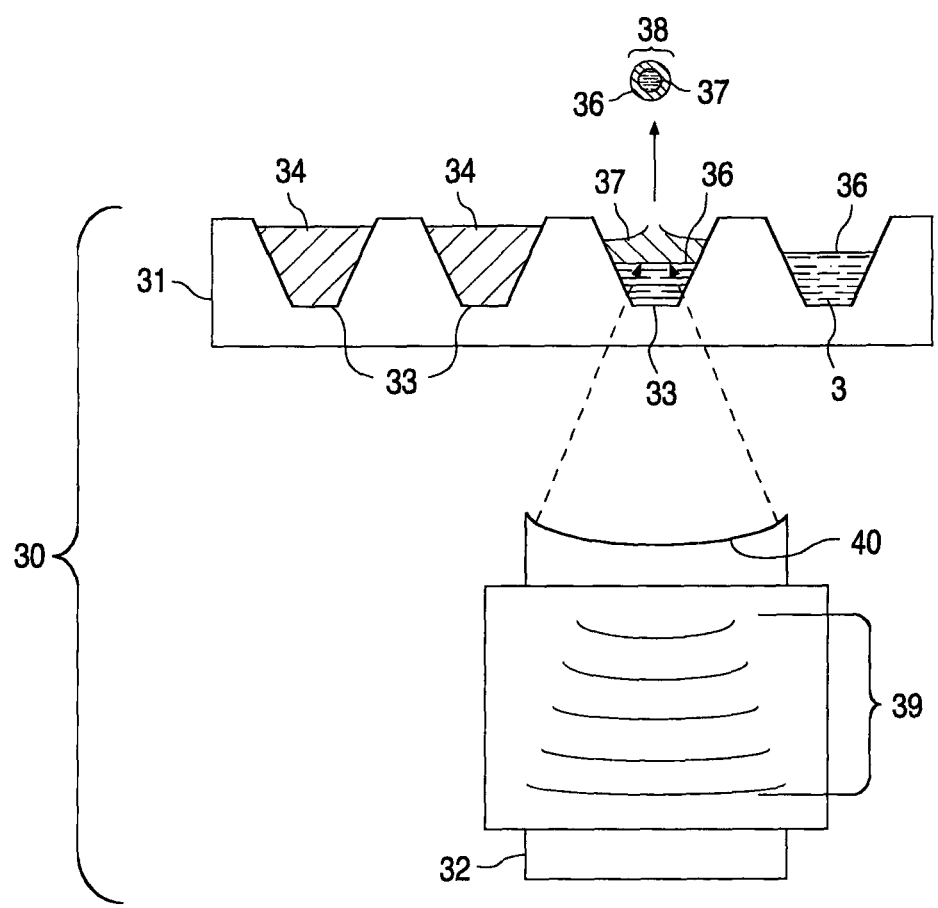

FIGS. 10a and 10b illustrate an ejector assembly that does not require a nozzle, according to some embodiments of the present invention. In some embodiments, the ejector assembly 30 can be used for controlled delivery of a coating composition that does not require a nozzle. FIG. 10a illustrates a cross section of the ejector assembly 30 comprising a reservoir housing 31 and a transducer 32. The transducer 32 outputs acoustic energy 39 at a reservoir 33 focused at the surface of the coating composition 34 therein. Each pulse ejects a known amount of the coating composition 34 in a droplet 35 from the reservoir 33 onto a medical device, thereby decreasing the coating composition 34 level in the reservoir 33. Accordingly, after each pulse of acoustic energy 39, the transducer 32 can be refocused to the new level in the reservoir 33 by a lens 40.

In an alternative embodiment, the reservoir 33 can be constantly refilled, thereby keeping the coating composition 34 level the same throughout the coating process. In some embodiments of the invention, the reservoirs 33 can each hold different coating substances. In one example, a first reservoir can hold a first coating composition 34 while a second reservoir can hold a second coating composition 36. The transducer 32 can then cause the ejection of different coating substances onto the medical device during a single coating process. Further, since there is no contact between the transducer 32 and reservoirs 33, the chance of cross contamination between reservoirs 33 is minimized or eliminated and there is no possibility of clogging any ejector assembly 30. It should be appreciated that nearly any number of compositions can be applied using this method.

In the embodiment shown in FIG. 10b, one or more of the reservoirs 33 may contain two different coating substances: a first substance 36 and a second substance 37, such that the transducer 33 can eject a combined drop 38 from the reservoir 33 by focusing a pulse of acoustic energy 39 at the interface between the two substances. The pulse of acoustic energy 39 is focused by the lens 40. Accordingly, in some embodiments, the medical device can be coated simultaneously with two different coating substance, such as a first substance 36 encapsulating a second substance 37. In some embodiments, the first substance 36 can be a biodegradable polymer selected to control the release of second substance 37, which can be a desired bioactive agent. In other embodiments, the first substance 36 can be a first agent, and the second substance 37 can be a second agent, wherein the agents can be any agent taught herein.

An advantage of the ejector assembly 30 illustrated in FIGS. 10a and 10b is the improved ability to eject controlled volumes, such as droplets, in a true "drop-on-demand," or "monodispersed" form. In some embodiments, the controlled-volumes can be delivered drop-by-drop in specific locations. In some embodiments, the controlled volumes can be delivered in a continuous string using, for example, high frequency acoustic energy.

In some embodiments, the droplets can be formed from a combination of a first agent and a first polymer that is applied within a combination of layers, wherein each layer may otherwise have its own concentration of a second agent, and the combination of layers forms IC profiles for two agents. In these embodiments, droplets can be formed from agents encapsulated by a second polymer, and the encapsulation can provide an additional control over the release of the agent from the second polymer, protect the agent to improve shelf-life, or a combination thereof.

In some embodiments, the encapsulated agent can be pure, blended with a polymer, connected to a polymer, or a combination thereof. In some embodiments, the first polymer can be hydrophilic and the second polymer can be hydrophobic; the first polymer can be hydrophobic and the second polymer can be hydrophilic; both the first and second polymers can be hydrophobic; both the first and second polymers can be hydrophilic; or at least one of the first or second polymers can be amphiphilic. In some embodiments, a polymer is considered hydrophilic due to the presence of any hydrophilic moiety that is combined with the polymer such as, for example, poly(ethylene glycol) or a glycosaminoglycan including, but not limited to, heparin and hyaluronic acid.

In some embodiments, droplets can be formed and applied as a suspension within a coating composition, and the coating composition can be applied using any coating method described above such as, for example, spraying, dipping, and controlled-volume formation, to name a few. In controlled volume formation, a droplet can be encapsulated within a larger droplet for a staged release of one or more agents. In these embodiments, the droplets can be formed in various sizes, wherein the sizes can vary due to the amount of agent, amount of encapsulating polymer, or a combination thereof.

In other embodiments, the droplets can be sandwiched between one or more layers that can be formed from droplets or from more traditional coating techniques such as, for example, spraying or dipping. It should be appreciated that these embodiments are not limited to coatings, since the droplets can be formed and dispersed in a polymeric composition that has been designed to form the structure of a medical device.

The controlled-volumes can be delivered in a variety of sizes. In some embodiments, the controlled-volumes can be dispersed in volumes that range from about 1 femtoliter to about 1 microliter, from about 1 femtoliter to about 100 nanoliters, from about 1 femtoliter to about 10 nanoliters, from about 10 femtoliters to about 0.1 nanoliters, from about 10 femtoliters to about 100 picoliters, from about 100 femtoliters to about 10 picoliters, and any range therein. In some embodiments, the controlled-volume is smaller than 10 picoliters to assist in even distribution of monodisperse droplets. An advantage of this broad range of controlled-volumes is that extremely potent agents can be delivered alone in the desired quantities to a desired area on a surface of a medical device. Another advantage of this broad range of controlled-volumes is that multiple agents can be delivered independently, or in combination, in a range of quantities to a range of desired areas and on multiple surfaces of a medical device.

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures. In some embodiments, the control of the application of energy includes manual control by the operator. In other embodiments, the control of the application of energy includes a programmable heating control system. In some embodiments, the application of energy can result in a coating composition temperature that ranges from about 35° C. to about 100° C., from about 35° C. to about 80° C., from about 35° C. to about 55° C., or any range therein. In some embodiments, any procedure for drying or curing known to one of skill in the art is within the scope of this invention.

In some embodiments, a medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30° C. to about 200° C., from about 35° C. to about 190° C., from about 40° C. to about 180° C., from about 45° C. to about 175° C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

Forming Compositions

The compositions taught herein can be used in some embodiments to form medical articles such as, for example, medical devices, coatings, or a combination thereof. The medical articles can include a combination of agents, wherein each of the agents (i) can be incorporated in the device or coating without cross-contamination from the other agents; (ii) can perform its function substantially free from interference from the other agents, (ii) can be incorporated in the device or coating such that the agent has a predetermined release rate and absorption rate; and (iv) can be combined with other agents that are bioactive, biobeneficial, diagnostic, and/or control a physical property or a mechanical property of a medical device.

The terms "combine," "combined," "combining," and "combination" all refer to a relationship between components of a composition and include blends, mixtures, linkages, and combinations thereof, of components that form the compositions. The linkages can be connections that are physical, chemical, or a combination thereof.

Examples of physical connections include, but are not limited to, an interlinking of components that can occur, for example, in interpenetrating networks and chain entanglement. Examples of chemical connections include, but are not limited to, covalent and non-covalent bonds. Covalent bonds include, but are not limited to, simple covalent bonds and coordinate bonds. Non-covalent bonds include, but are not limited to, ionic bonds, and inter-molecular attractions such as, for example, hydrogen bonds and attractions created by induced and permanent dipole-dipole interactions. All of these types of combinations can have a variable effect on the measured diffusion coefficient.

The material considerations include, but are not limited to, the selection of the polymer and/or polymer combinations, the selection of the agent and/or agent combinations, the selection of the polymer/agent combinations, and the selection of the solvent and/or solvent combinations used to combine the materials for application. The scope of the present invention includes, but is not limited to, the following methods of forming compositions:

The compositions of the present invention include any combination of polymers, copolymers and agents. The compositions can include not only polymers but also polymers combined with ceramics and/or metals, which can also affect the relationship between the elements in the system. Examples of ceramics include, but are not limited to, hydroxyapatite, BIOGLASS®, and absorbable glass. Examples of metals include, but are not limited to magnesium, copper, titanium, and tantalum.

Polymeric matrices that are formed in the present invention should meet particular requirements with regard to physical, mechanical, chemical, and biological properties. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing.

An example of a chemical property that can affect performance of a biodegradable composition in vivo is the rate of absorption of the composition by a subject. An example of a biological property that can affect performance of a composition in vivo is the bioactive and/or biobeneficial nature of the composition in a subject, both of which are described below. The terms "subject" and "patient" can be used interchangeably and refer to an animal such as a mammal including, but not limited to, non-primates such as, for example, a cow, pig, horse, cat, dog, rat, and mouse; and primates such as, for example, a monkey or a human.

While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo. In some embodiments, an increase in hydrolysis can also increase the release rate of an agent by creating channels within a medical article or coating that can serve as transport pathways for diffusion of the agents from the composition within a subject.

The relative hydrophilicity of the components within a polymeric matrix affects the release of agents from a polymeric matrix, so control over the relative hydrophilicity of the components provides for control over the release rate of agents. Hydrophobicity and hydrophilicity, as used herein, are relative terms used to compare chemical moieties. The relative hydrophobicity and hydrophilicity of polymers, for example, can be determined by comparing the Hildebrand solubility parameter of each polymer, which is a value that is readily obtainable to one of skill in the art. In most embodiments, the "hydrophilic polymer" simply has a higher solubility parameter value than the "hydrophobic polymer." In embodiments containing more than two polymers, the polymers can be ranked in order by comparing their solubility parameters.

In some embodiments, water uptake can be increased by combining a hydrophilic moiety such as, for example, a hydrophilic polymer, with the polymeric matrix. In some embodiments, the hydrophilic polymers may also be non-fouling and include, but are not limited to, both biodegradable and non-biodegradable polymers such as, for example, poly(ethylene glycol)(PEG); poly(ethylene oxide); poly(ethylene glycol-co-propylene oxide)(PEG-PPO); dextran; dextrin; poly(vinyl alcohol); poly((2-hydroxyethyl)methacrylate) (HEMA); poly(vinyl pyrrolidone); (PVP); poly(butylene terephthalate-co-ethylene glycol) (PBT-PEG or POLYACTIVE™); poly(alkylene oxalates); pluronic acid; sulfonated polystyrene; block copolymers with a bioabsorbable block and a perfluoro chain; PEG-caprolactone; PEG-D,L-lactide; biomolecules such as fibrin, fibrinogen, cellulose, starch, collagen, heparin and hyaluronic acid; poly(vinyl alcohols); and combinations thereof.

In some embodiments, the hydrophilic moieties include, but are not limited to, poly(ethylene glycol) and glycosaminoglycans such as, for example, heparin and hyaluronic acid. In some embodiments, the hydrophilic moiety can be added in the range of from about 0.01% to about 99.99%; from about 0.1% to about 99.9%; from about 1% to about 99%; from about 3% to about 97%; from about 5% to about 95%; from about 7% to about 93%; from about 10% to about 90%; from about 15% to about 85%; from about 20% to about 80%; from about 25% to about 75%; from about 30% to about 70%; from about 40% to about 60%; about 50%; or any range therein, wherein the percent is a weight percent based on total polymer in the composition. It is to be appreciated that in some embodiments, any one or any combination of the hydrophilic, non-fouling polymers taught herein could excluded from any embodiment taught herein for reasons known to one of skill in the art.

Without intending to be bound by any theory or mechanism of action, the tendency of hydrophilic polymers to leach out of the polymeric matrices of the present invention can be minimized by choosing a hydrophilic, non-fouling polymer having a molecular weight that is high enough to prevent or inhibit leaching. The choice of molecular weight can be based on the hydrophilicity of the polymer—the more hydrophilic the polymer, the higher the molecular weight necessary to prevent or inhibit leaching.

Another important characteristic of a composition relative to the release of an agent is the porosity of the polymeric matrix formed from the composition. In some embodiments, a polymeric matrix may be formed using a pore forming agent. The pore forming agent can be dispersed or mixed within the composition used to form the polymeric matrix.

In some embodiments, a pore forming agent in the form of particles and/or fibers, for example, may be added to a polymeric material used to form the polymeric matrix. Pore formation can occur when at least a portion of the pore forming agent is dissolved or eroded by a fluid. The fluid may be any solvent capable of dissolving or eroding the pore-forming agent such as for example, water or bodily fluids. In some embodiments, a tortuous porous network can form through one or more layers of polymeric matrices in a medical article to allow agent release to occur.

In some embodiments, the process of forming pores in a polymeric matrix can occur in vitro. Alternatively or additionally, the pore-forming agent may be removed through dissolution and/or erosion of the pore forming agent when the polymeric matrix, or a portion thereof, is exposed to bodily fluids after implantation of the device.

Various biologically compatible pore-forming agents may include, but are not limited to, salts, sugars, and water-soluble polymers. Examples of salts include, but are not limited to, sodium chloride, phosphate salts, carbonate salts, sodium bicarbonate, polymeric salts, and combinations thereof. Examples of water-soluble polymers include, but are not limited to, polymeric salts, polyvinyl alcohol, polyethylene glycol, polyethylene oxide, glucose, dextran, dextrose, lactose, gamma globulin, albumin, and combinations thereof. In some embodiments, the pore-forming agents may be removed in vivo, for example, by washing in water or a very dilute acid bath. Other pore forming agents include, but are not limited to, urea and amino acids.

In some embodiments, a pore formation rate can be controlled after implantation by selecting a second bioabsorbable polymer with a known average erosion rate or erosion "half-life." Similarly, some embodiments may include an erodible metal mixed or dispersed with the polymeric matrix as a pore-forming agent.

It should be appreciated that properties of the porous polymeric matrix may influence the degradation rate. Such properties include, but are not limited to, pore size distribution and porosity. Porosity may be defined as the ratio of the void volume to the total volume of the polymeric matrix. In some embodiments, the erosion profile may be controlled by controlling the pore size distribution and porosity of the polymeric matrix.

The pore size distribution and porosity can depend on variables that include, but are not limited to, the size and concentration of particles and/or fibers per unit volume of the polymeric matrix. Accordingly, in some embodiments, the pore size distribution porosity can be controlled by controlling the size and concentration of particles and/or fibers that are added to the compositions.

Another important characteristic of a composition relative to the release of an agent is the glass-transition temperature (Tg) of the polymeric matrix formed from the composition. The Tg of a polymer is not only a measure of the thermal behavior of the polymer, but is also a measure of the mechanical and surface properties that can be expected from a matrix comprising the polymer. Polymers with a low Tg tend to be softer and, thus, prone to mechanical failure during manipulation; and, the polymeric matrix tends to be more permeable to the diffusion of agents. Polymers with a high Tg tend to be brittle and, thus, prone to mechanical failure in high strain areas of the polymeric matrix.

The term "low Tg polymer" refers to a biocompatible polymer having a Tg that is less than or equal to a normal body temperature for a human. The term "high Tg polymer" refers to a biocompatible polymer having a Tg that is greater than the normal body temperature. The term "very low Tg polymer" refers to a biocompatible polymer having a Tg that is at least about 20° C. lower than the normal body temperature.

The Tg of a polymer can be modified by methods that include, but are not limited to, (1) altering the mobility of the polymer by changing the chemical structure of the polymer such as, for example, by altering the polymer backbone; adding, removing, or replacing pendant groups; altering molecular weight and/or molecular weight distribution; and combinations thereof;

(2) altering the relationship between polymers by, for example, blending the polymer with other polymers; adding fillers and/or fillers; and combinations thereof;

and any combinations of (1) and (2).

Functional groups that stiffen a polymer can include, but are not limited to, short chain diacids, diamides, amino acids, aromatic diols, aromatic diacids, and styrene, each of which having from about 1 to about 30 carbons; from about 1 to about 20 carbon atoms; from about 1 to about 10 carbon atoms; from about 1 to about 6 carbon atoms; and any range therein. Some representative stiffening groups include, but are not limited to the following chemical moieties:

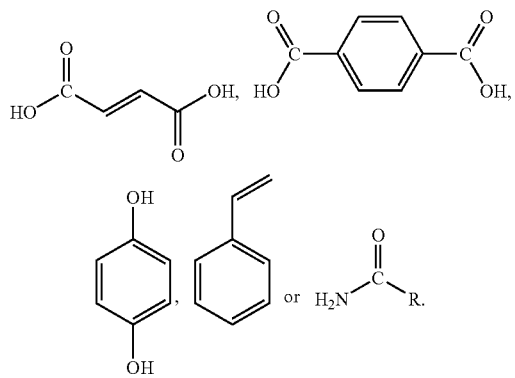

In one embodiment, a poly(ester amide) (PEA) having a low Tg and at least one reactive group in its backbone such as, for example, a carboxyl group can be modified with a stiffening group to increase the Tg as shown in Scheme 1.

Scheme 1

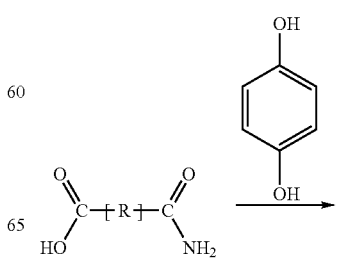

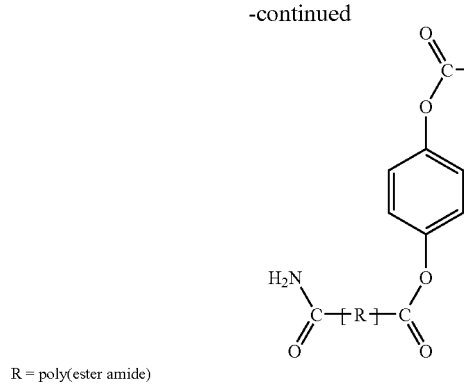

R = poly(ester amide)

In general, flexible backbone moieties decrease the Tg; pendant groups that inhibit rotation of the polymer increase the Tg; cross-linking between polymers increases the Tg; and, an increase in chemical interaction between polymers such as, for example, by incorporating ionic bonding, H-bonding, dative bonding, and dipole interaction, can also increase Tg. However, it should be appreciated that bulky pendant groups that inhibit rotation can also increase free volume, and the increase in free volume decreases Tg. The converse of these principles apply to decreasing the Tg of a polymer, and a decrease in interaction between polymer chains can be achieved, in some embodiments, by the addition of an agent.

In some embodiments, polymers having hydroxyl end groups can be modified by short chain diacids or aromatic diacids through an ester bond. In some embodiments, polymers having hydroxyl end groups can be converted to other groups such as amino or aldehyde groups for further modification. In one example, the polymer having hydroxyl groups comprises PEG, which can be modified as follows:

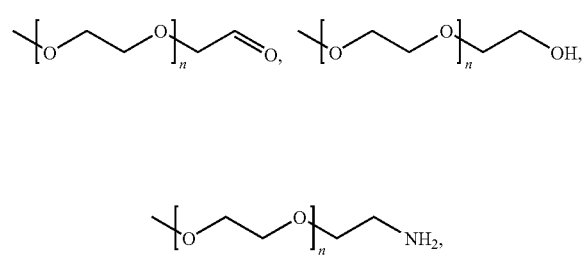

where n is an integer not equal to zero, and is selected to provide the desired molecular weight of the polymer. The PEGs in all embodiments of the present invention can have molecular weights ranging from about 100 Daltons to about 4000 Daltons, from about 200 Daltons to about 2000 Daltons, from about 300 Daltons to about 1000 Daltons, from about 400 Daltons to about 900 Daltons, from about 500 Daltons to about 800 Daltons, or any range therein.

The PEG bearing hydroxyl or amino end groups can be modified with a diacid to form ester or amide bonds. The PEG bearing aldehyde end groups can be modified with stiffening groups having diamines as shown in Scheme 2.

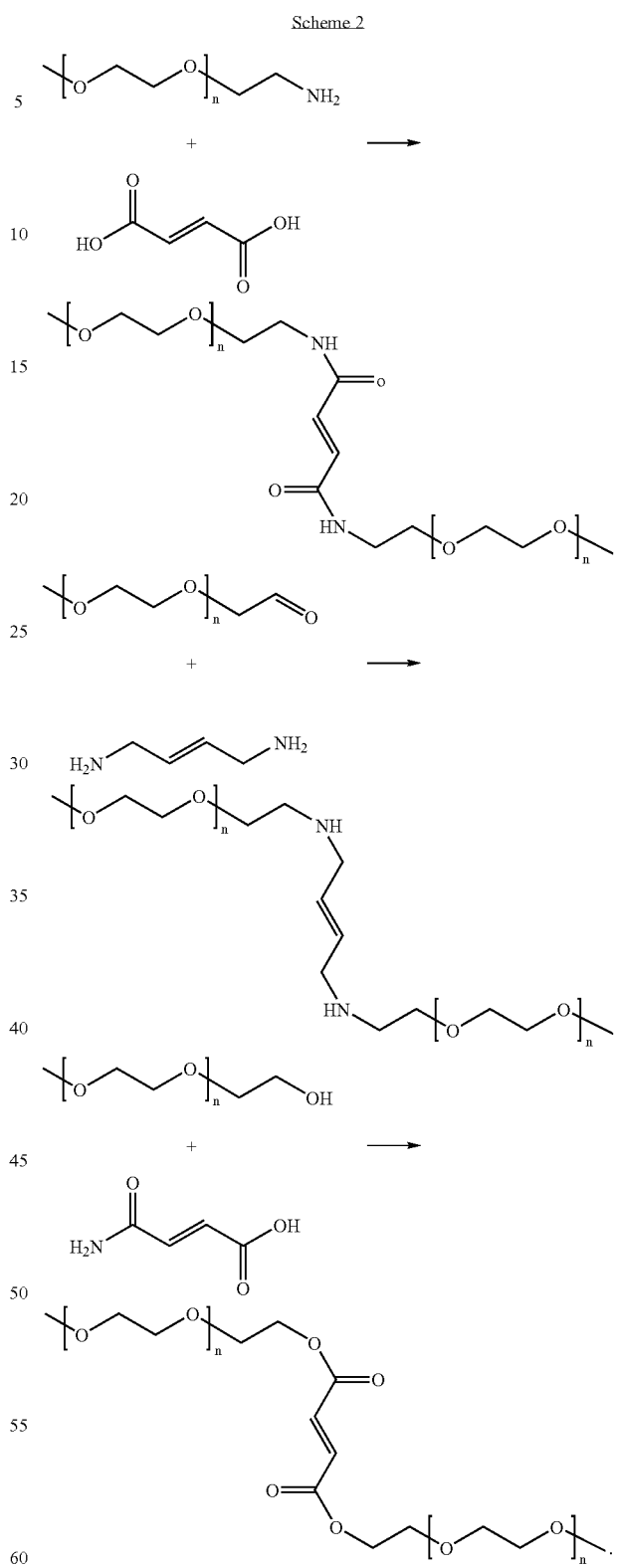

Scheme 2

The backbone of a low $T_g$ polymer can also be modified by replacing all or part of the pendant groups with different pendant groups such as, for example, less bulky pendant groups to decrease fractional free volume and increase Tg as shown in Scheme 3.

Scheme 3

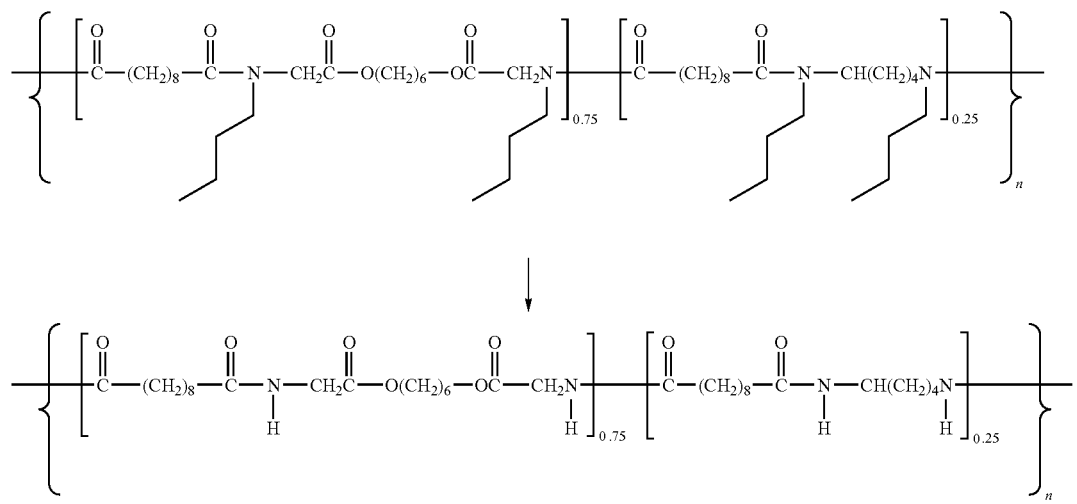

The $T_g$ of the modified polymer in Scheme 3 may be increased as the less linear bulky pendant groups would allow the polymer molecules to pack better.

In some embodiments, the Tg of a polymer can be increased or decreased by varying the molecular weight and/or molecular weight distribution of the polymer. The Tg can be increased by increasing the molecular weight beyond the threshold of chain entanglement for the polymer, because the physical chain entanglement decreases the mobility of the polymer. Conversely, a decrease in molecular weight can likewise decrease the Tg of a polymer.

In some embodiments, the Tg of a polymer can be increased by narrowing the molecular weight distribution of the polymer, because the a narrower distribution of molecular weight can facilitate better molecular packing between polymer chains. Likewise, a broader molecular weight distribution can be chose to decrease the Tg of a polymer.

In some embodiments, the Tg of a polymeric matrix can be controlled by blending a first polymer having a first Tg with a second polymer having a second Tg. In some embodiments, the first polymer can comprise the bulk of the composition and the second polymer can comprise a minor component of the composition. For example, composition can comprise about 50%-99.99% the first polymer and about 0.01%-50% the second polymer by weight. If the first polymer has a high Tg, and the second polymer has a low or very low Tg, the resultant polymer blend would provide a controlled, effective Tg.

Blending a low or very low Tg polymer and a high Tg polymer allows one to combine the mechanical strength of the high Tg polymer and the flexibility of the low or very low Tg polymer, thus providing a means for controlling the release of agents from the polymeric matrix due to diffusion, the physical and mechanical properties of a medical article formed using the matrix, and the release of agents from the polymeric matrix due to degradation. Moreover, such control in increasing the effective Tg of the polymeric coating composition can provide for a means to slow the degradation rate of the composition to reduce inflammatory responses to the degradation products.

The Tg of a polymeric matrix can be altered through the addition of biocompatible fillers and agents taught herein. The biocompatible fillers include materials such as, for example, chopped fiber and high surface/volume ratio particulates. As used herein, the term "high surface/volume ratio" refers to nanometer- and/or micrometer-sized particulates ranging from about 0.1 nanometer to about 1000 microns; from about 1 nanometer to about 100 microns; from about 1 nanometer to about 50 microns; from about 1 nanometer to about 1 micron; from about 1 nanometer to about 100 nanometers; from about 0.1 nanometer to about 10 nanometers; from about 10 nanometers to about 50 nanometers; from about 10 nanometers to about 100 nanometers; or any range therein.

Any biocompatible chopped fibers can be used. In some embodiments, the biocompatible chopped fibers include, but are not limited to, absorbable materials such as poly(glycolic acid), poly(dioxanone), absorbable glass fibers, carbon nanotube fibers and non-absorbable materials such as polyethylene, poly(ethylene vinyl alcohol), polypropylene, poly(ethyleneterephthalate), hydroxyapatite, and combinations thereof. In some embodiments, the high surface/volume ratio particulates include, but are not limited to, alumina particulates, carbon nanoparticles, carbon nanoshells, carbon nanotubes, hydroxyapatite, tricalcium phosphate, α-tricalcium phosphate, β-tricalcium phosphate, carbides, nitrides, $TiO_2$, $SiO_2$, calcium sulfate, carbonate-apatite (DAHLITE), titanium, niobium, tantalum, platinum, alloys of platinum and iridium, and combinations thereof. In some embodiments, the reinforcement materials, for example carbon nanotube, $Al_2O_3$, and polypropylene, can also contribute to passivation of the coating surface.

In some embodiments, the chopped fibers and/or high surface/volume particulates can be present in amounts ranging from about 0.01% to about 20%; from about 0.1% to about 15%; from about 1% to about 10%; from about 2% to about 7%; or any range therein by weight of the total composition.

The Polymers

A polymeric matrix can comprise polymers that are biodegradable, which can be due to the labile nature of chemical functionalities within the polymer network such as, for example, ester groups that can be present between chemical moieties. Accordingly, these compositions can be designed such that they can be broken down, absorbed, resorbed and eliminated by a mammal. The compositions of the present invention can be used, for example, to form medical articles such as, for example, medical devices and coatings.

The polymers used in the present invention may include, but are not limited to, condensation copolymers, and should be chosen according to a desired performance parameter of a product that will be formed from the composition. Such performance parameters may include, for example, the toughness of a medical device or coating, the capacity for the loading concentration of an agent, and the rate of biodegradation and elimination of the composition from a subject. If the other polymers in a composition are non-biodegradable, they should be sized to produce polymer fragments that can clear from the subject following biodegradation of the composition.

For the purposes of the present invention, a polymer or coating is "biodegradable" when it is capable of being completely or substantially degraded or eroded when exposed to an in vivo environment or a representative in vitro. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation.

In some embodiments, a polymer that is considered biodegradable can be one that has functional groups in its primary backbone that are susceptible to cleavage—usually, but not necessarily, hydrolytic cleavage—when placed in a physiological environment having a primarily aqueous composition. In these embodiments, the environment can have a pH of approximately 7-7.5, one or more hydrolytic enzymes, other endogenous biological compounds that catalyze or at least assist in the degradation process, or a combination thereof. The terms "bioabsorbable" and "biodegradable" can be used interchangeably in some embodiments of this application.

In some embodiments, the number average molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

In some embodiments, the polymers that can be used include natural or synthetic polymers; homopolymers and copolymers, such as, for example, copolymers that are random, alternating, block, graft, and/or crosslinked; or any combination and/or blend thereof. The copolymers include, but are not limited to, polymers with two or more different types of repeating units such as, for example, terpolymers.

In some embodiments, the polymers used in the compositions of the present invention can have a crystallinity at 40° C. that is less than 50 weight percent (wt %), less than less than 30 wt %, less than 20 wt %, or a combination thereof. While not intending to be bound by any theory or mechanism of action, the term "crystallinity" can refer to regions in which polymer chains align with one another, usually parallel, to form crystalline lattices in an effort to obtain the most favorable thermodynamics.

There are a variety of methods used to determine percent crystallinity of a polymer, and each of these methods, although well-known to those skilled in the art, is usually expected to produce a somewhat different crystallinity measurement than may be obtained using a different measurement method for a given polymeric material. While not intending to be bound by any theory or mechanism of action, percent crystallinity can be determined using calorimetry such as, for example thermogravimetric analysis/differential scanning calorimetry; spectroscopy such as, for example, infrared spectroscopy and nuclear magnetic resonance spectroscopy; x-ray diffraction techniques, such as wide-angle x-ray diffraction; gravimetric determinations, including density determinations, specific volume measurements, and the like.

In some embodiments, the polymers include, but are not limited to, poly(acrylates) such as poly(butyl methacrylate), poly(ethyl methacrylate), poly(hydroxyl ethyl methacrylate), poly(ethyl methacrylate-co-butyl methacrylate), and copolymers of ethylene-methyl methacrylate; poly(2-acrylamido-2-methylpropane sulfonic acid), and polymers and copolymers of aminopropyl methacrylamide; poly(cyanoacrylates); poly (carboxylic acids); poly(vinyl alcohols); poly(maleic anhydride) and copolymers of maleic anhydride; and any derivatives, analogs, homologues, congeners, salts, copolymers and combinations thereof.

In some embodiments, the polymers include, but are not limited to, fluorinated polymers or copolymers such as poly (vinylidene fluoride), poly(vinylidene fluoride-co-hexafluoropropene), poly(tetrafluoroethylene), and expanded poly (tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly (hydroxybutyrate-co-valerate); poly(dioxanones); poly (orthoesters); poly(anhydrides); poly(glycolic acid); poly(glycolide); poly(D,L-lactic acid); poly(D,L-lactide); poly (glycolic acid-co-trimethylene carbonate); poly (phosphoesters); poly(phosphoester urethane); poly (trimethylene carbonate); poly(iminocarbonate); poly (ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly (lactic acid); poly(anhydrides), poly(alkylene oxalates); poly (phosphazenes); poly(urethanes); silicones; poly(esters; poly (olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly (ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, at least one of polymers can be a poly(ester amide), a poly(lactide) or a poly(lactide-co-glycolide) copolymer; and any derivatives, analogs, homologues, congeners, salts, copolymers and combinations thereof. In a variety of embodiments, at least one of the polymers can be a poly(ester amide) and any derivatives, analogs, homologues, congeners, salts, copolymers and combinations thereof. In some embodiments, the polymers are selected such that they specifically exclude any one or any combination of the polymers that are taught herein.

In some embodiments, the polymers can be biodegradable. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of any of the polymers taught herein.

In some embodiments, the polymers can be chemically connected to the agents by covalent bonds. In other embodiments, the polymers can be chemically connected to the agents by non-covalent bonds such as, for example, by ionic bonds, inter-molecular attractions, or a combination thereof. In other embodiments, the polymers can be physically connected to the agents.

In other embodiments, the polymers can be chemically and physically connected with the agents. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed with the agents.

The Agents

Biobeneficial and Bioactive Agents

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly (acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD).

In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents taught herein may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one embodiment, the bioactive agent inhibits the activity of vascular smooth muscle cells. In another embodiment, the bioactive agent can be used to control migration or proliferation of smooth muscle cells to inhibit restenosis. In another embodiment, the bioactive agent can be used in the prevention and/or treatment of restenosis and/or vulnerable plaque. In some embodiments, the term "treatment" includes, but is not limited to, the mitigation, diagnosis, ameliorization of the symptoms, or a combination thereof, of a disease.

Bioactive agents include, but are not limited to, antiproliferatives, antineoplastics, antimitotics, anti-inflammatories, antiplatelets, anticoagulants, antifibrins, antithrombins, antibiotics, antiallergenics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, dactinomycin (COSMEGEN™, Merck & Co., Inc.), imatinib mesylate, and any prodrugs, metabolites, analogs, homologues, congeners, derivatives, salts and combinations thereof. Antineoplastics or antimitotics include, for example, paclitaxel (TAXOL®, Bristol-Myers Squibb Co.), docetaxel (TAXOTERE®, Aventis S.A.), midostaurin, methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), midostaurin, and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide; imatinib mesylate; and any prodrugs, metabolites, analogs, homologues, congeners, derivatives, salts and combinations thereof. Antiallergenic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; 42-Epi-(tetrazoylyl)rapamycin (ABT-578); 40-O-(2-hydroxy)ethyl-rapamycin (everolimus); tacrolimus; pimecrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO);

4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radioopaque materials and include, but are not limited to, materials comprising iodine or iodine-derivatives such as, for example, iohexyl and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomography (PET).

Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

Systems for delivering agent combinations can be more effective at combating restenosis than single drug systems and more efficacious for certain patient subsets such as, for example, patients with diabetes or diffuse, multi-vessel disease. Moreover, combination drugs may be necessary for pro-healing strategies.

In some embodiments, a system for delivery of a combination of agents such as, for example, a combination of clobetasol and everolimus. Clobetasol is a very potent anti-inflammatory drug from a class of drugs called "super potent glucocorticoids." Delivery of clobetasol can inhibit the inflammatory process that can result from, for example, vascular injury incurred through placement of a stent. Vascular injury can release inflammatory cytokines and growth factors that may result in the hyper-proliferation of vascular smooth muscle cells and lead to restenosis. The delivery of clobetasol to the site of injury can inhibit this process. The combination of clobetasol with everolimus can address restenosis on multiple pathways to provide results that may be more beneficial than the results that can be achieved through administration of either drug alone.

In some embodiments, a combination of agents can be applied, as taught herein, within predetermined IC profiles within a medical device, on a medical device, or positioned within a controlled volume at a predetermined region on the device or within a coating on the device. In some embodiments, the agent combination includes everolimus and clobetasol. In other embodiments, the agent combination includes tacrolimus and rapamycin. In other embodiments, the agent combination includes tacrolimus and everolimus. In other embodiments, the agent combination can include rapamycin and paclitaxel. In other embodiments, the agent combination can include an anti-inflammatory such as, for example, a corticosteroid and an antiproliferative such as, for example, everolimus. In some embodiments, the agent combinations can provide synergistic effects for preventing or inhibiting conditions such as, for example, restenosis that may occur through use of a stent.

Plasticizing Agents

The terms "plasticizer" and "plasticizing agent" can be used interchangeably in the present invention, and refer to any agent, including any agent described above, where the agent can be added to a polymeric composition to modify the mechanical properties of the composition or a product formed from the composition. Plasticizers can be added, for example, to reduce crystallinity, lower the glass-transition temperature ($T_g$), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as, for example, single-block polymers, multi-block copolymers, and other copolymers such as graft copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In some embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly (esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate and any analogs, derivatives, copolymers and combinations thereof.

In some embodiments, the plasticizers include, but are not limited to, sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In some embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In some embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In some embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In some embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and, any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the present invention, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the present invention. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

It should also be appreciated that the plasticizers can be combined with other active agents to obtain other desired functions such as, for example, an added therapeutic, prophylactic, and/or diagnostic function. In some embodiments, the plasticizers can be linked to other agents through ether, amide, ester, orthoester, anhydride, ketal, acetal, carbonate, and all-aromatic carbonate linkages to control the degradation of the plasticizer from the polymeric matrix.

In some embodiments, the agents can be chemically connected to a polymer by covalent bonds. In other embodiments, the agents can be chemically connected to a polymer by non-covalent bonds such as, for example, by ionic bonds, inter-molecular attractions, or a combination thereof. In some embodiments, the agents can be physically connected to a polymer. In some embodiments, the agents can be chemically and physically connected with a polymer.

Examples of ionic bonding can include, but are not limited to, ionic bonding of an anionic agent to a cationic site on a polymer or a cationic agent to an anionic site on a polymer. In some embodiments, an anionic agent can be bound to a quaternary amine on a polymer. In some embodiments, an agent with a quaternary amine can be bound to an anionic site on a polymer. Examples of inter-molecular attractions include, but are not limited to, hydrogen bonding such as, for example, the permanent dipole interactions between hydroxyl, amino, carboxyl, and sulfhydryl groups, and combinations thereof. Examples of physical connections can include, but are not limited to, interpenetrating networks and chain entanglement. The agents can also be blended or mixed with the compositions.

In some embodiments, the agents have a reactive group that can be used to link the agents to the polymer. Any reactive group known to one of skill the art can be used, and examples of reactive groups include, but are not limited to, hydroxyl, acyl, formyl, amino, amido, hydroxyl, sulfhydryl, and the like. In some embodiments, the agents can be released or can separate from the polymeric matrices through degradation.

In some embodiments, the molecular weight of an agent should be at or below about 40,000 Daltons, or any range therein, to ensure elimination of the agent from a mammal. In some embodiments, the molecular weight of the agent ranges from about 300 Daltons to about 40,000 Daltons, from about 8,000 Daltons to about 30,000 Daltons, from about 10,000 Daltons to about 20,000 Daltons, or any range therein. If the biobeneficial agent is rapidly broken down in the body upon release, then the molecular weight of the agent could be greater than about 40,000 Daltons without compromising patient safety. The molecular weights as taught herein are a number average molecular weight.

It should also be appreciated that the agents of the present invention can have properties that are biobeneficial, bioactive, diagnostic, plasticizing, or a combination thereof. For example, classification of an agent as a biobeneficial agent does not preclude the use of that agent as a bioactive agent, diagnostic agent and/or plasticizing agent. Likewise, classification of an agent as a bioactive agent does not preclude the use of that agent as a diagnostic agent, biobeneficial agent and/or plasticizing agent. Furthermore, classification of an agent as a plasticizing agent does not preclude the use of that agent as a biobeneficial agent, bioactive agent, and/or diagnostic agent. It should also be appreciated that any of the foregoing agents can be combined with the compositions such as, for example, in the form of a medical device or a coating for a medical device. By way of a non-limiting example, a stent coated with the compositions of the invention can contain paclitaxel, docetaxel, rapamycin, methyl rapamycin, ABT-578, everolimus, clobetasol, pimecrolimus, imatinib mesylate, midostaurin, or combinations thereof.

Concentrations of Agents

In some embodiments, the agents of the present invention can be added in combination to obtain the desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject.

It is to be appreciated that the design of a composition for the sustained release of agents can be dependent on a variety of factors such as, for example, the therapeutic, prophylactic, ameliorative or diagnostic needs of a patient. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In other embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and, any range therein, where the percentage is based on the total weight of the polymer and agent or combination of agents.

Preparing a Poly(Ester Amide) by Design

Designing and applying a polymeric composition comprising a poly(ester amide), wherein the poly(ester amide) has a design that was preselected to provide a predetermined release rate within polymeric matrices can provide a means for one of skill in the art to control the delivery of the agents. This control can aid in preventing adverse effects, and promoting desirable effects, that can be obtained from the delivery of agents within a subject. The embodiments for the coating compositions that are taught herein are not meant to be limiting. Other coating configurations are possible and are virtually limitless in variety in the practice of the invention.

In some embodiments, the poly(ester amides) can be limited to a single layer. In these embodiments, the single layer may have one or more poly(ester amides) for release of one or more agents that are dissolved in a polymer matrix and/or one or more agents that are in a dispersed phase within a polymer matrix.

In some embodiments, a combination of layers can have one or more poly(ester amides), wherein each layer within the combination of layers may or may not include an agent. In these embodiments, each layer within the combination of layers may include one or more poly(ester amides) for the delivery of one or more agents that are dissolved in a polymer matrix and/or one or more agents that are in a dispersed phase within a polymer matrix.

In some embodiments, the poly(ester amides) within the polymeric matrix can be designed such that the agents are delivered through a combination of layers, wherein at least one of which contains a controlled IC profile, and the combination of layers provides an overall controlled IC profile. In these embodiments, each layer within the combination of layers may have a concentration gradient based on one or more agents that are dissolved in a polymer matrix and/or one or more agents that are in a dispersed phase within a polymer matrix.

In some embodiments, the compositions of the present invention comprise a poly(ester amide) (PEA), which due to the labile nature of the ester groups, makes the structure biodegradable. The PEA comprises at least one amide group and at least one ester group and, as a result, can have a wide variety of molecular configurations. Such a polymer can exhibit, for example, sufficient mechanical strength for stent coating applications and an ability to be broken down, absorbed, resorbed and eliminated by a mammal.

The polymers used in the present invention may be biodegradable and may include, but are not limited to, condensation copolymers. It should be appreciated, however, that less than 100% of a biodegradable composition may comprise a PEA, such that polymers other than PEA can compose the balance of composition. In addition, these other polymers can also be blended or cross-linked with the PEA using, for example, an isocyanate or a diisocyanate. If these other polymers are also biodegradable, the amount incorporated should be limited by their effect on a required performance parameter of a product formed from the biodegradable polymer. Such performance parameters may include, for example, the mechanical strength of a coating or the rate of biodegradation and elimination of a coating from a mammal. If the other polymers are non-biodegradable, the polymer fragments produced during biodegradation should have molecular weights of a size that ensures elimination of the fragments from a mammal, as discussed herein.

In some embodiments, the composition includes a polymer and an agent. In some embodiments, the composition can be a reaction product of a polyol, a polycarboxylic acid, an amino acid and, optionally, an agent.

The polyols used in the present invention may be organic compounds having two or more hydroxyl groups. In some embodiments, the polyols include, but are not limited to, cyclohexanedimethanol, glycerol, trimethylolpropane, pentaerythritol and compounds represented by a formula (I):

wherein R can be a substituted, unsubstituted, hetero-, straight-chained, branched, cyclic, saturated or unsaturated aliphatic radical; or a substituted, unsubstituted, or hetero-aromatic radical; and i is an integer.

In some embodiments, the polyols are diols. Examples of diols that can be used include ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, dihydroxyacetone, serinol, and cyclohexanedimethanols such as, for example, 1,4-cis-cyclohexanedimethanol. In other embodiments, the diols can be aromatic diols such as, for example, 1,4-benzenedimethanol (also known as p-phenylene dicarbinol or as p-xylene-α,α'-diol). In other embodiments, polyols such as glycerol, trimethylolpropane, pentaerythritol and sorbitol are useful as long as the possibility of forming a crosslink is considered. Polyols can be selectively polymerized by protecting one or more groups to prevent crosslinking, intentionally forming a crosslink, or using chemistry that is selective for particular reactive groups. In other embodiments, functional diols such as serinol and diacetone alcohol can also be used.

In other embodiments, R can be a substituted or unsubstituted poly(alkylene glycol), which includes, but are not limited to, poly(ethylene glycol) (PEG); a functionalized PEG such as, for example, amino-terminated PEG; PPG; poly (tetramethylene glycol); poly(ethylene oxide-co-propylene oxide); poly(ethylene glycol-co-hydroxybutyrate); or copolymers and combinations thereof. It is to be appreciated that one skilled in the art should recognize that some of the groups, subgroups, and individual polyols may not be used in some embodiments of the present invention.

The PEGs in all embodiments of the present invention can have molecular weights ranging from about 100 Daltons to about 4000 Daltons, from about 200 Daltons to about 2000 Daltons, from about 300 Daltons to about 1000 Daltons, from about 400 Daltons to about 900 Daltons, from about 500 Daltons to about 800 Daltons, or any range therein. It is to be appreciated that one skilled in the art should recognize that some of the groups, subgroups, and individual polyols may not be used in some embodiments of the present invention.

With respect to the chemical notation used herein, each of the functional groups, R, can be independently selected from substituted, unsubstituted, hetero-, straight-chained, branched, cyclic, saturated or unsaturated aliphatic radicals; or substituted, unsubstituted, or hetero-aromatic radicals. For example, an R group can be selected from H; aliphatic hydrocarbon groups such as, for example, alkyl, alkenyl, and alkynyl groups; aromatic groups such as, for example, aryl, aralkyl, aralkenyl, and aralkynyl groups; and, various other groups as defined below.

In some embodiments of the present invention, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 6 to about 180 carbon atoms, from about 12 to about 150 carbon atoms, from about 18 to about 120 carbon atoms, from about 24 to about 90 carbon atoms, from about 30 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, iso-octyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms are replaced by a functional group or an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain where at least one of the carbon-carbon linkages is a carbon-carbon double bond. The term "alkynyl" refers to a straight-chained or branched hydrocarbon chain where at least one of the carbon-carbon linkages is a carbon-carbon triple bond. The term "aryl" refers to a hydrocarbon ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In other embodiments, a radical is straight-chained if it has less than 0.001 mole percent of such side chains. A radical is "branched" when it has more than 0.1 mole percent of side chains having 1 or more carbon atoms.

In some embodiments, a radical is branched when it has more than 0.01 mole percent of such side chains. In other embodiments, a radical is branched when it has more than 0.001 mole percent of such side chains. The terms "radical," "group," "functional group," and "substituent" can be used interchangeably in some contexts and can be used together to further describe a chemical structure. For example, the term "functional group" can refer to a chemical "group" or "radical," which is a chemical structure variable that is in-chain, pendant and/or terminal to the chemical structure. Such a functional group may be substituted.

Examples of substituents in substituted radicals include, but are not limited to, hydroxyls, carboxyls, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

The polycarboxylic acids used in the present invention may be organic acids having two or more carboxyl groups. In some embodiments, the polycarboxylic acids include dicarboxylic acids and tricarboxylic acids and may be aliphatic or aromatic structures. In one embodiment, the polycarboxylic acids are represented by a formula (II):

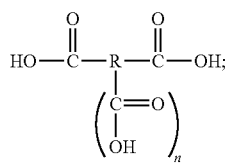

wherein R is optional and can be a substituted, unsubstituted, hetero-, straight-chained, branched, cyclic, saturated or unsaturated aliphatic radical; and a substituted or unsubstituted aromatic radical; and n is an integer. Examples of polycarboxylic acids include, but are not limited to, oxalic acid, malonic acid, succinic acid, glutaric acid, adipic acid, pimelic acid, suberic acid, sebacic acid, azelaic acid, terephthalic acid, citric acid, maleic acid, fumaric acid and combinations thereof. It is to be appreciated that one skilled in the art should recognize that some of the groups, subgroups, and individual polycarboxylic acids may not be used in some embodiments of the present invention.

In some embodiments, R is a methylene [—$(CH_2)_y$—] or phenylene group [—$C_6H_4$—], where y is an integer between 0 and 16. In other embodiments, R can include a substituted or unsubstituted poly(alkylene glycol), which includes, but is not limited to, PEG, PEG derivatives such as amino-terminated PEG and carboxyl-terminated PEG; PPG; poly(tetramethylene glycol); poly(ethylene oxide-co-propylene oxide); poly(ethylene glycol-co-hydroxybutyrate); or copolymers and combinations thereof. In other embodiments R can be aryl. In other embodiments, R can be substituted with an epoxy group.

The amino acids used in the present invention may be organic compounds comprising an amino group and a carboxyl group, and the amino group may be primary or secondary. Examples of amino acids include, but are not limited to, glycine, alanine, valine, leucine, isoleucine, methionine, phenylalanine, tyrosine, aspartic acid, glutamic acid, lysine, arginine, serine, threonine, cysteine, asparagine, proline, tryptophan, histidine and combinations thereof. In some embodiments, the amino acids are represented by a formula (III):

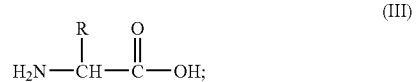

wherein R may be a hydrogen; a substituted, unsubstituted, hetero-, straight-chained, branched, cyclic, saturated or unsaturated aliphatic radical; or a substituted, unsubstituted, or hetero-aromatic radical. In some embodiments, R can be substituted, unsubstituted, or hetero-forms of methyl, isopropyl, sec-butyl, iso-butyl, benzyl, or a combination thereof.

In embodiments where R is substituted, examples of substitutents include, but are not limited to, hydroxyl, carboxyl, amino, imino groups and combinations thereof. In embodiments where R is heteroaliphatic, examples of heteroatoms include, but are not limited to, sulfur, phosphorous, oxygen, nitrogen and combinations thereof. In other embodiments, R can comprise substituted or unsubstituted poly(alkylene glycols), which include, but are not limited to, PEG, PEG derivatives such as mPEG, poly(ethylene oxide), PPG, poly(tetramethylene glycol), poly(ethylene oxide-co-propylene oxide), or copolymers and combinations thereof.

In some embodiments, the poly(alkylene glycol) is PEG. In other embodiments, the poly(alkylene glycol) may comprise a PEG derivative such as mPEG. In another embodiment, R can comprise a co-polymer of PEG or a copolymer of a PEG derivative such as mPEG.

In some embodiments, the amino acids may be limited to bifunctional amino acids. In other embodiments, the amino acids may be limited to trifunctional amino acids. In some embodiments, the amino acids may be limited to diamines. In other embodiments, the amino acids may be limited to triamines.

In some embodiments, the amino acids may be limited to monocarboxylics. In other embodiments, the amino acids may be limited to dicarboxylics. In some embodiments, the amino acids may be limited to aliphatics. In other embodiments, the amino acids may be limited to aromatics. In some embodiments, the amino acids may be limited to amides. In other embodiments, the amino acids may not include lysine. It is to be appreciated that one skilled in the art should recognize that some of the groups, subgroups, and individual amino acids taught herein may not be used in some embodiments of the present invention.

PEA-Agent Combinations

The agents of the present invention can be connected to a PEA as a pendant group or as an in-chain group. It should be appreciated that the agent can be a polymeric agent, which can be attached as a pendant group or as an in-chain group. It should also be appreciated from the teachings provided herein that selecting and combining any of the agents and/or R-groups taught herein to form the polymeric compositions of the present invention can alter the diffusion coefficient and/or the degradation rate of a given polymeric matrix.

I. The Agent as a Pendant Group

A polymer of the present invention can comprise a polymeric carrier having an A-moiety (A), a B-moiety (B), and an optional linkage ($L_1$) connecting A to B. The remainder of the polymer comprises an agent (X), and a linkage ($L_2$) connecting X to the polymer. This PEA-agent combination can be generally represented by a formula (IV):

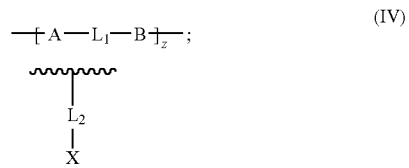

wherein the ratio of A:B may be less than, greater than, or equal to one, and z is an integer. In some embodiments, z can range from about 10 to about 1600, from about 20 to about 1200, from about 30 to about 900, from about 50 to about 600, or any range therein.

In formula (IV), both A and B can be independently selected and comprise any combination of monomers such that the polymer has at least one ester group and one amide group. In some embodiments, the ester and amide are adjacent. Optionally, A and B can be connected by $L_1$, which can be independently selected as a substituted, unsubstituted, hetero-, straight-chained, branched, cyclic, saturated or unsaturated aliphatic radical; or a substituted or unsubstituted aromatic radical.

In some embodiments, $L_1$ can comprise from about 0 to about 50 carbon atoms, from about 2 to about 40 carbon atoms, from about 3 to about 30 carbon atoms, from about 4 to about 20 carbon atoms, from about 5 to about 10 carbon atoms, and any range therein. In other embodiments, the $L_1$ can alternately comprise a non-carbon species such as, for example, a disulfide. In other embodiments, $L_1$ can comprise substituted or unsubstituted poly(alkylene glycols), which include, but are not limited to, PEG, PEG derivatives, poly(ethylene oxide), PPG, poly(tetramethylene glycol), poly(ethylene oxide-co-propylene oxide), or copolymers and combinations thereof. In one embodiment, the poly(alkylene glycol) is PEG. In some embodiments, the poly(alkylene glycol) may comprise a PEG derivative. In some embodiments, $L_1$ can comprise a copolymer of PEG or a copolymer of a PEG derivative.

In some embodiments, X can also be optional and can be connected to the polymer by $L_2$, which can be independently selected as any interunit linkage known to one of skill in the art such as, for example, an ester, an anhydride, an acetal, an amide, a urethane, a urea, a glycoside, a disulfide, a siloxane linkage, or a combination thereof. It should be appreciated that one skilled in the art should recognize that some of these linkages may not be used in some embodiments of the present invention.

The careful selection of the linkers, $L_1$ and $L_2$, allow for control of the rate of degradation of the polymeric matrix. The selection of $L_2$, for example, allows for control of the relative strength or stability of the bond between X and the polymeric carrier as compared to the strength or stability of the bonds within the polymeric carrier. Control over this relative strength or stability allows for release of bioactive agents that are substantially free of attached molecules from the polymeric carrier. The agent, X, can be biobeneficial, bioactive, diagnostic or a have a combination of these characteristics, and is discussed in detail above.

In some embodiments, each $L_1$ and $L_2$ can be independently selected to control the rate of polymer degradation and can include amides, ureas, urethanes, esters, semicarbazones, imines, oximes, anhydrides, ketals, acetals, orthoesters, disulfides, and all-aromatic carbonates. In some embodiments, $L_1$ and $L_2$ can be independently selected to comprise an ester, an anhydride, a ketal, an acetal, an orthoester, or an all-aromatic carbonates. In some embodiments, $L_1$ and $L_2$ can be independently selected to comprise an anhydride, a ketal, an acetal, an orthoester or an all-aromatic carbonate. In some embodiments, $L_1$ and $L_2$ can be independently selected to comprise a ketal, an acetal, an orthoester or an all-aromatic carbonate. In some embodiments, $L_1$ and $L_2$ can be independently selected to comprise an acetal, an orthoester or an all-aromatic carbonate. In some embodiments, $L_1$ and $L_2$ can be independently selected to comprise an orthoester or an all-aromatic carbonate.

Each $L_1$ and $L_2$ can be independently selected to provide for a controlled-release rate of agents in controlled steps. In some embodiments, each $L_1$ can be selected to degrade slower than any $L_2$ to avoid agent release due to degradation of the polymer. In some embodiments, each $L_2$ can be the same, and the release rate of the agents varies due to the electron-withdrawing or electron-donating character of the agents attached to each $L_2$. In some embodiments, each $L_2$ can be different, and the release rate of the agents corresponds to the differences in degradation between each $L_2$. In some embodiments, each $L_1$ can be selected to degrade at the same rate as each $L_2$, for example, to allow for release of agents from an underlying polymeric matrix. One of skill in the art can design the polymeric matrices with preselected linkers to provide a design that was preselected to provide a predetermined release rate of the combination of agents from the medical article, wherein the design provides a predetermined rate of degradation of the agents from the polymeric matrix, or a combination thereof.

In some embodiments, A can be represented by a formula (V):

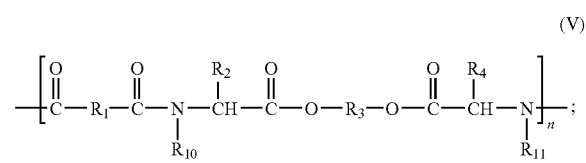

and in other embodiments, B can be represented by any of formulas (VI)-(VIII);

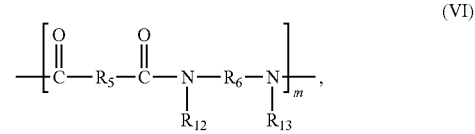

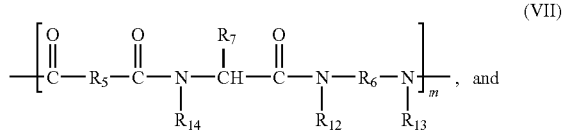

(VIII)

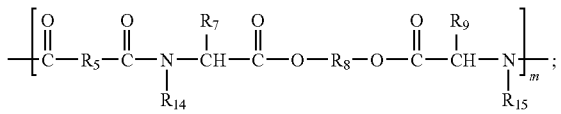

where $R_1$ and $R_5$ can be optional and can also be independently selected from a substituted, unsubstituted, hetero-, straight-chained, branched, cyclic, saturated or unsaturated aliphatic radical; or a substituted, unsubstituted, or hetero-aromatic radical; $R_3$ and $R_8$ can be independently selected from a substituted, unsubstituted, hetero-, straight-chained, branched, cyclic, saturated or unsaturated aliphatic radical; or a substituted, unsubstituted, or hetero-aromatic radical; $R_2$ and $R_4$ can be independently selected from a hydrogen; a substituted, unsubstituted, hetero-, straight-chained, branched, cyclic, saturated or unsaturated aliphatic radical; or a substituted, unsubstituted, or hetero-aromatic radical; $R_6$ can be selected from a substituted, unsubstituted, hetero-, straight-chained or branched aliphatic radical; $R_7$ and $R_9$ can be independently selected from a hydrogen; a substituted, unsubstituted, hetero-, straight-chained, branched, cyclic, saturated or unsaturated aliphatic radical; and a substituted or unsubstituted aromatic radical; $R_{10}$ through $R_{15}$ can be independently selected from a hydrogen; a substituted, unsubstituted, hetero-, straight-chained, branched, cyclic, saturated or unsaturated aliphatic radical; or a substituted, unsubstituted, or hetero-aromatic radical; m can range from about 4 to about 1400, from about 10 to about 800, from about 20 to about 400, or any range therein; n can range from about 3 to about 1400, from about 10 to about 800, from about 20 to about 400, or any range therein; and the sum of m and n and can range from about 30 to about 1600, from about 50 to about 1200, from about 75 to about 900, from about 100 to about 600, or any range therein. In some embodiments, groups $R_{10}$ through $R_{15}$ are limited to hydrogen. In other embodiments, $R_1$ is not equal to $R_5$.

In some embodiments, the R-groups present in A and B can be selected to provided a desired rate of degradation of the polymeric matrix. In some embodiments, the R-groups can comprise electron-withdrawing groups in the design of the poly(ester amides) of the present invention. In some embodiments, the R-groups can comprise electron donating groups in the design of the poly(ester amides) of the present invention.

The selection of electron-withdrawing and electron-donating groups in the design of a biodegradable polymer can affect the rate of degradation of the polymeric matrix. The term "electron-withdrawing group" refers to the ability of a substituent to attract valence electrons from neighboring atoms. An electron-withdrawing group can attract the valence electrons because it is more electronegative than neighboring atoms. The term "electron-donating group" refers to the ability of a substituent to contributes electrons. An electron-donating group can donate electrons because it is more electropositive than neighboring atoms.

Without intending to be bound by any theory or mechanism of action, one of skill in the art can refer to the Hammett sigma value as a measure of an R-group's electron-donating and withdrawing capability. See Streitweiser, A.; Heathcock, C. Organic Chemistry (Macmillan Publ. Co. 1985). The Hammett constant values are generally negative for electron-donating groups and positive for electron-withdrawing groups. In some embodiments, the electron-donating groups and electron-withdrawing groups are selected and added to the polymers of the present invention to control the degradation rate of the polymeric matrix.

In some embodiments, the electron-withdrawing groups can include, but are not limited to, nitro, acyl, formyl, sulfonyl, trifluoromethyl, halogeno, and cyano groups, among others. In some embodiments, the electron-donating groups can include, but are not limited to, amino, alkylamino, dialkylamino, aryl, alkoxy, aralkoxy, aryloxy, mercapto, alkylthio, hydroxyl groups, and the like. Any R-groups known to one of skill in the art can be used to serve as electron-withdrawing or electron-donating groups in the design of the poly(ester amides) of the present invention.

The polymers of the present invention can generally be prepared in the following manner: a polyester-type moiety is prepared by combining an amino acid with a diol. In some embodiments, the amino acid is a bi-functional amino acid. The polyester-type moiety can be combined with a multi-functional amino acid, a diacid or derivative of a diacid, and an agent. In embodiments where a peptide-type moiety is desired, two amino acids can be independently selected and combined such as, for example, where one amino acid is bi-functional and the other is multi-functional. An example of a multi-functional amino acid is a tri-functional amino acid.

Examples of tri-functional amino acids include, but are not limited to, lysine, tyrosine, arginine, or glutamic acid. Examples of diacids include, but are not limited to, the dicarboxylic acids listed above. Examples of derivatives of diacids include, but are not limited to, diacid chloride, a dianhydride, or a di-p-nitrophenyl ester. In the event that a dicarboxylic acid is used, the reaction may be carried out in the presence of 1-ethyl-3(3-dimethylaminopropyl) carbodiimide (EDC) or 1,3-dicyclohexylcarbodiimide (DCC) in a solvent such as dimethylformamide (DMF) or tetrahydrofuran (THF). If a diacid chloride or di-p-nitrophenyl ester is used, an excess of pyridine or triethylamine should be present. Examples of other solvents that may be used include, but are not limited to, dimethylacetamide (DMAC), dimethylsulfoxide (DMSO), acetone, and dioxane.

The reaction conditions should be anhydrous and favor esterification of the amino acid's carboxyl group. In some embodiments, the reaction solvents include toluene and benzene and should be distilled to remove water. The reaction can be catalyzed by a strong acid or base such as, for example, p-toluenesulfonic acid (TsOH). In some embodiments, the temperature of the reaction ranges from about 25° C. to about 150° C., from about 35° C. to about 100° C., from about 50° C. to about 80° C., or any range therein. In some embodiments, the reaction times range from about 1 hour to about 24 hours, from about 6 hours to about 18 hours, from about 10 hours to about 14 hours, or any range therein. Any agent described above can be used.

Trifunctional amino acids can be incorporated into the polymer by protecting the third functionality with a protecting group that is later removed. Examples of protecting groups are benzyl esters for the lysine carboxyl or t-butoxycarbonyl for amino groups such as, for example, the amino group in glutamic acid. In some embodiments, the amino acid that is selected to link with the agent is not lysine.

The benzyl ester protecting group may be removed from the lysine carboxyl by hydrogenolysis with hydrogen gas over a catalyst such as, for example, palladium or platinum on carbon. Examples of suitable solvents include, but are not limited to, ethanol, methanol, isopropanol, and THF. In some embodiments, the reaction may be conducted under about 1 atm of hydrogen for about 6 hours to about 24 hours, for about 8 hours to about 16 hours, for about 10 hours to about 14 hours, or any range therein. After removal of the protecting group, an agent comprising an amino, a hydroxyl, a thiol, or a combination thereof is connected to the carboxyl group. Coupling agents used to connect the agent include, but are not limited to, EDC and DCC. Thionyl chloride or phosphorous pentachloride may be used in a less selective process of preparing the acid chloride derivative.

An amine functional compound such as, for example, 4-amino-TEMPO, may be connected to a polymer containing free carboxyls such as, for example, the lysine-derived carboxyls, by first activating the carboxyls and coupling the amine in a solvent under agitation. The carboxyls may be activated with, for example, N-hydroxysuccinimide (NHS) and DCC in a solvent such as, for example, THF or chloroform, which produces N-hydroxysuccinimidyl ester.

Examples of the solvent that may be used to couple the amine to the carboxyls include, but are not limited to, THF and DMF. In some embodiments, the reaction occurs at a temperature ranging from about 5° C. to about 50° C., from about 15° C. to about 35° C., from about 20° C. to about 30° C., or any range therein. In some embodiments, the reaction time ranges from about 0.5 hours to about 24 hours, from about 1 hour to about 18 hours, from about 4 hours to about 16 hours, from about 6 hours to about 12 hours, or any range therein.

In one embodiment, a family of PEAs can be prepared by reacting a diol, a diacid, two independently selected amino acids, and an agent. The resulting product is PEA represented by a formula (IX):

In formula (X), the groups $R_1$, $R_3$ and $R_5$ are independently selected, straight-chained or branched, saturated, aliphatic radicals having from 2-20 carbon atoms. The groups $R_2$ and $R_4$ are independently selected, straight-chained or branched, saturated, aliphatic radicals having from 1-6 carbon atoms; straight-chained or branched, aliphatic radicals having from 2-6 carbon atoms and at least one unsaturated carbon-carbon bond; straight-chained or branched, aliphatic radicals having from 2-6 carbon atoms and at least one carbon-carbon triple bond; phenyl radicals; an ortho-fused bicyclic carbocyclic radical having 6-10 carbon atoms and at least one aromatic ring; or hydrogen. The group X is a straight-chained or branched, saturated, aliphatic radical having from 1-6 carbon atoms; a phenyl radical; an ortho-fused bicyclic carbocyclic radical having 6-10 carbon atoms and at least one aromatic ring; or hydrogen. The subscripts m and n are integers not equal to 0.

In some embodiments of the present invention, diacids comprising epoxy groups may not be used to produce the PEAs. In other embodiments, diacids comprising epoxy groups may not be used to produce the PEAs where the amino acid chosen to link with X is lysine, and X is 4-amino-TEMPO or rapamycin. In other embodiments, $R_1$ and $R_5$ may not be substituted with epoxy groups where $R_1$ and $R_5$ are straight-chained-butylene or straight-chained-hexylene radicals. In other embodiments, $R_1$ and $R_5$ may not be substituted with epoxy groups where $R_1$ and $R_5$ are straight-chained-butylene or straight-chained-hexylene radicals, and X is TEMPO or rapamycin.

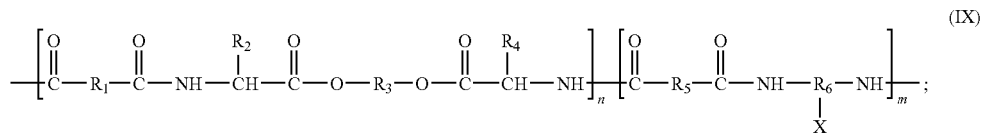

where the groups $R_1$ and $R_5$ can be optional and can also be independently selected substituted, unsubstituted, hetero-, straight-chained, branched, cyclic, saturated or unsaturated aliphatic radicals; or substituted or unsubstituted aromatic radicals. The group $R_3$ can be a substituted, unsubstituted, hetero-, straight-chained, branched, cyclic, saturated or unsaturated aliphatic radical; or a substituted, unsubstituted, or hetero-aromatic radical. The groups $R_2$ and $R_4$ can be independently selected hydrogens; substituted, unsubstituted, hetero-, straight-chained, branched, cyclic, saturated or unsaturated aliphatic radicals; or substituted or unsubstituted aromatic radicals. The group $R_6$ can be a substituted, unsubstituted, hetero-, straight-chained or branched aliphatic radical. The group X can be an agent; and n and m are integers not equal to 0.

Note, however, that in some embodiments, the polymers of the present invention do not comprise the following combination of the A-moiety, B-moiety, $L_2$, and X as represented by a formula (X):

In other embodiments, $R_1$ and $R_5$ may not be substituted with epoxy groups where $R_1$ and $R_5$ are straight-chained-butylene or straight-chained-hexylene radicals, when X is 4-amino-TEMPO or rapamycin, and $L_2$ is the following ester linkage prior to connecting X to $L_2$:

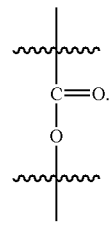

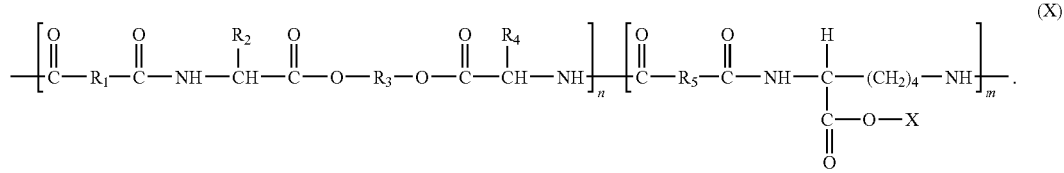

In other embodiments, $R_1$ and $R_5$ may not be substituted with epoxy groups where $R_1$ and $R_5$ are straight-chained-butylene or straight-chained-hexylene radicals, and (i) X is TEMPO and $L_2$ is

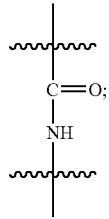

or, (ii) X is rapamycin and $L_2$ is

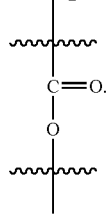 [SMILES: *OC(*)=O]

In other embodiments, a PEA may not be produced from a polycarboxylic acid that is 2,3-epoxysuccinic acid, 3,4-epoxyadipic acid or a diepoxyadipic acid, where the amino acid chosen to link with X is lysine, and X is 4-amino-TEMPO or rapamycin. In other embodiments, $R_1$ is not the same as $R_5$.

In formula (X), $L_2$ is an ester, which may be undesirable in some embodiments. As illustrated and described below, the careful selection of $L_2$ can help alleviate regulatory issues that may arise from the creation of derivatives of X during biodegradation of the polymers.

Examples of $L_2$ include, but are not limited to, amides, esters, anhydrides, ketals, acetals, orthoesters and all-aromatic carbonates. In some embodiments, $L_2$ can be an ester, an anhydride, a ketal, an acetal, an orthoester, or an all-aromatic carbonates. In some embodiments, $L_2$ can be an anhydride, a ketal, an acetal, an orthoester or an all-aromatic carbonate. In some embodiments, $L_2$ can be a ketal, an acetal, an orthoester or an all-aromatic carbonate. In some embodiments, $L_2$ can be an acetal, an orthoester or an all-aromatic carbonate. In some embodiments, $L_2$ can be an orthoester or an all-aromatic carbonate. In some embodiments, $L_2$ can be an all-aromatic carbonate, which includes linkages comprising moieties represented by formula (XI):

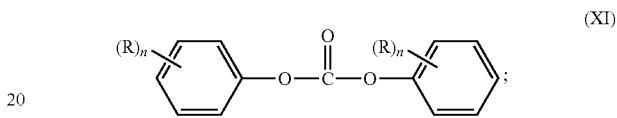

wherein R is optional and can be independently selected from, for example, a substituted, unsubstituted, hetero-, straight-chained, branched, cyclic, saturated and unsaturated aliphatic radicals; substituted and unsubstituted aromatic radicals; and combinations thereof. The subscript n is an integer not equal to 0.

In some embodiments, the PEA is represented by a formula (XII):

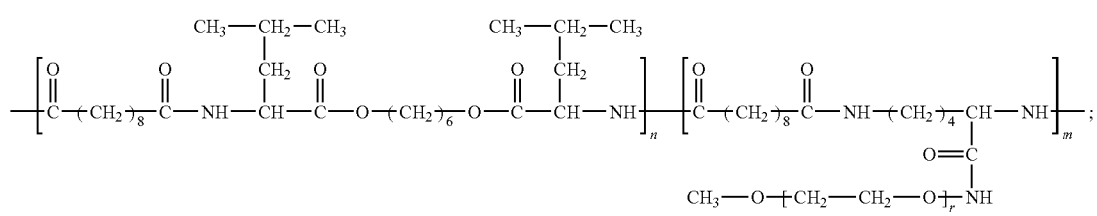

wherein n, m, and r are integers not equal to 0. In formula (XII), the diol is hexane-1,6-diol, the diacid is sebacic acid, one amino acid is leucine, the other amino acid is lysine, and the agent is mPEG. The mPEG is connected to the B-moiety through an amide linkage, which is a stable linkage relative to the stability of the remainder of the polymer.

Formula (XIII) represents a polymer with an amide linkage. Note, however, that in some embodiments, a PEA represented by formula (XIII) is not within the scope of the present invention:

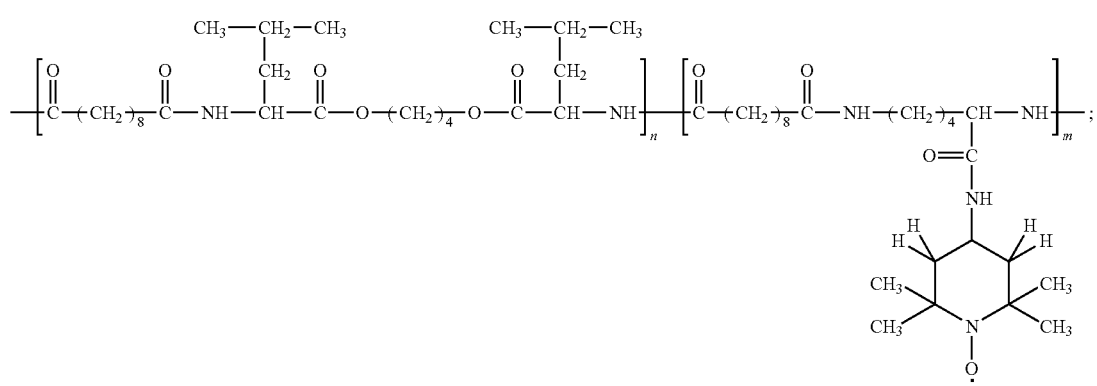

wherein n and m are integers not equal to 0. In formula (XIII), the diol is butane-1,6-diol, the diacid is sebacic acid, one amino acid is leucine, the other amino acid is lysine, and the agent is TEMPO. The TEMPO is connected to the B-moiety through an amide linkage, which may remain intact during biodegradation of the polymer resulting in attachment of additional molecules to the TEMPO that were derived from degradation of the polymer at the ester linkages. As a result, such a released agent would be a derivative of TEMPO rather than TEMPO and could cause regulatory concerns.

In some embodiments, the PEA is represented by a formula (XIV):

wherein n and m are integers not equal to 0. In formula (XV), the diol is butane-1,6-diol, the diacid is sebacic acid, one amino acid is leucine, the other amino acid is lysine, and the agent is TEMPO. The TEMPO is connected to the B-moiety through an anhydride linkage, which is more labile than an ester linkage and, thus, may allow for release of the agent without attachment of additional molecules derived from biodegradation of the polymer at ester linkages.

In another embodiment, a family of PEAs comprising a dipeptide fragment can be prepared by reacting a diol, a diacid, two different amino acids, and an agent. The resulting product is a PEA represented by a formula (XVI):

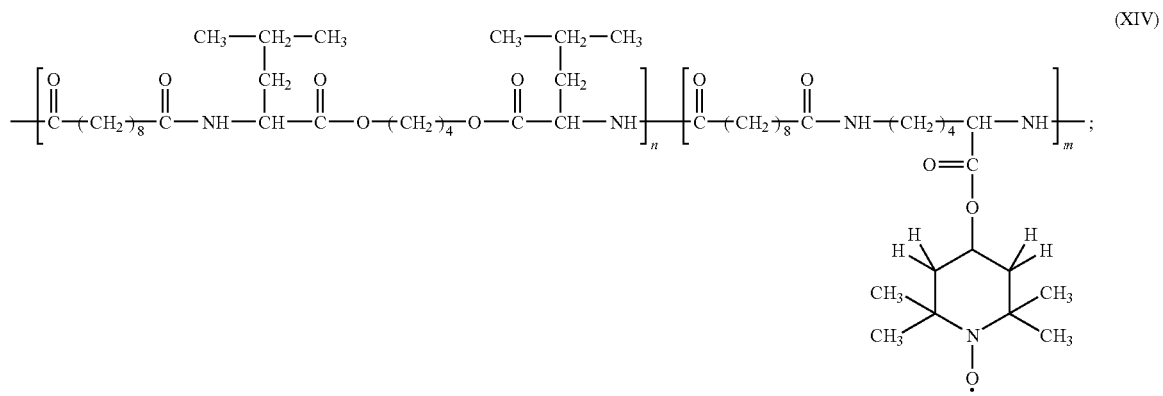

wherein n and m are integers not equal to 0. In formula (XIV), the diol is butane-1,6-diol, the diacid is sebacic acid, one amino acid is leucine, the other amino acid is lysine, and the agent is TEMPO. The TEMPO is connected to the B-moiety through an ester linkage, which is more labile than an amide linkage and allows for release of the agent from the polymer. The cleavage of the $L_2$ ester competes with the cleavage of the PEA esters and may result in attachment of additional molecules to the TEMPO that were derived from degradation of the polymer at ester linkages.

In some embodiments, the PEA is represented by a formula (XV):

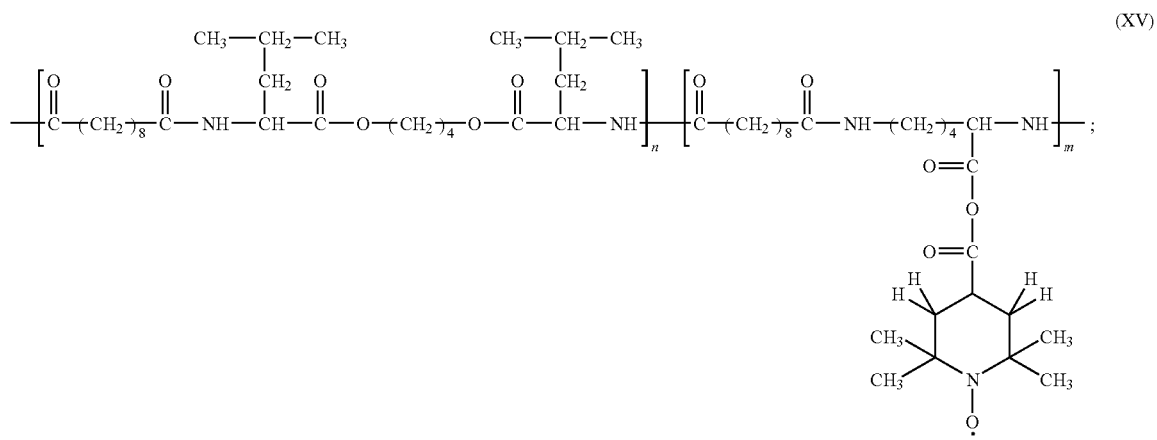

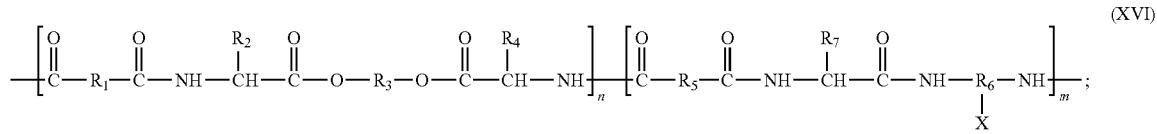

wherein where $R_1$ and $R_5$ can be optional and can also be independently selected from a substituted, unsubstituted, hetero-, straight-chained, branched, cyclic, saturated or unsaturated aliphatic radical; or a substituted, unsubstituted, or hetero-aromatic radical; $R_3$ can be independently selected from a substituted, unsubstituted, hetero-, straight-chained, branched, cyclic, saturated or unsaturated aliphatic radical; or a substituted, unsubstituted, or hetero-aromatic radical; $R_2$, $R_4$ and $R_7$ can be independently selected from a hydrogen; a substituted, unsubstituted, hetero-, straight-chained, branched, cyclic, saturated or unsaturated aliphatic radical; or a substituted, unsubstituted, or hetero-aromatic radical; $R_6$ can be selected from a substituted, unsubstituted, hetero-, straight-chained or branched aliphatic radical; X can be an agent; m can range from about 4 to about 1400; n can range from about 3 to about 1400; and the sum of m and n and can range from about 30 to about 1600.

In some embodiments, the PEA is represented by a formula (XVII):

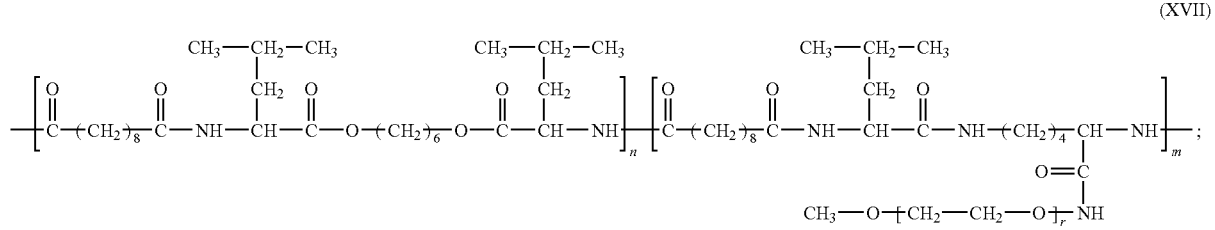

wherein n, m, and r are integers not equal to 0. In formula (XVII), the diol is hexane-1,6-diol, the diacid is sebacic acid, one amino acid is leucine, the other amino acid is lysine, X is mPEG and $L_2$ is an amide, which is stable relative to the stability of the remainder of the polymer.

In some embodiments, the PEA is represented by a formula (XVIII):

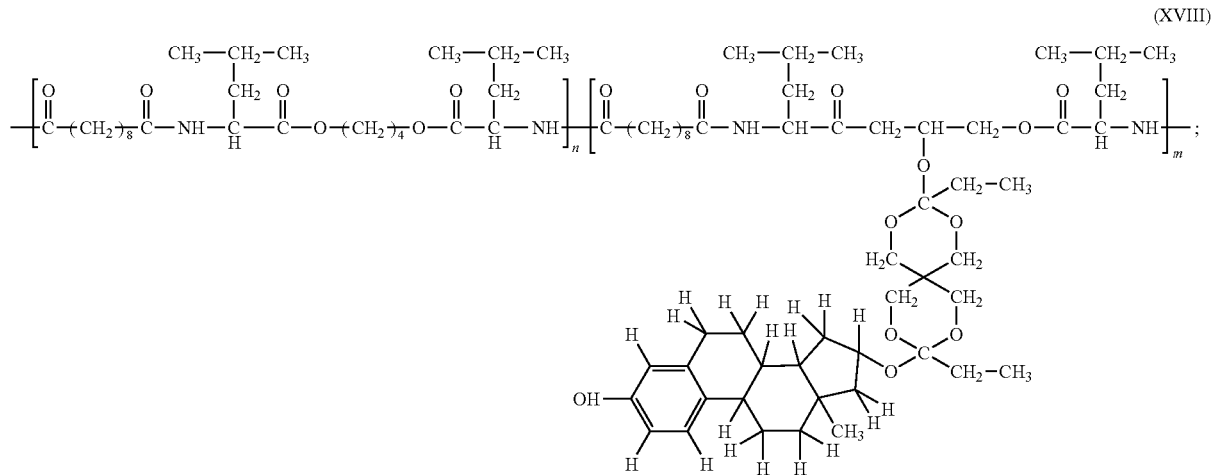

wherein n and m are integers not equal to 0. In formula (XVIII), the diol is butane-1,4-diol, the diacid is sebacic acid, one amino acid is leucine, the other amino acid is lysine, X is estradiol and $L_2$ is an orthoester known as 3,9-diethylidene-2,4,8,10-tetraoxaspiro-[5,5]-undecane (DETOSU), which is more labile than an ester.

To make the polymer, an oligo- or polyester-type diamino moiety can be made as described above, combining leucine and butane-1,4-diol. One equivalent of glycerol can be combined with two equivalents of leucine to obtain an amino-terminated polymeric subunit. Next, the polyester-type diamino moiety can be combined with sebacic acid and the amino-terminated polymeric subunit to obtain a hydroxy-functional PEA. Estradiol then can be combined with 3,9-diethylidene-2,4,8,10-tetraoxaspiro-[5,5]-undecane (DETOSU) to form an estradiol-DETOSU moiety. The hydroxy-functional PEA can be reacted with the estradiol-DETOSU moiety to form the PEA-agent combination.

A polymeric agent such as, for example, heparin can be connected to a PEA as a graft-copolymer. A PEA with pendant amino groups on the polymer backbone may be produced by a method that comprises polymerizing bis-(L-leucine)-1,6-hexylene diester with di-p-nitrophenyl sebacate and ε-carbobenzoxy-L-lysine in a suitable solvent such as, for example, DMF or THF.

The temperature of the reaction ranges from about 25° C. to about 150° C., from about 50° C. to about 125° C., from about 80° C. to about 100° C., or any range therein. The reaction occurs for a time ranging from about 1 hour to about 24 hours, from about 6 hours to about 18 hours, from about 10 hours to about 14 hours, or any range therein. The carbobenzoxy protecting group can be removed with hydrogenolysis over a palladium on carbon catalyst using the method described above. An aldehyde-terminated heparin can be connected by reductive amination using sodium cyanoborohydride (NaCNBH$_3$) and a DMF/water solvent.

II. Agent as a Polymeric Block

A polymeric agent can be connected to a PEA either pendant or as a block-copolymer. Examples of agents that can be combined with the PEAs as polymeric blocks include, but are not limited to, glycosaminoglycans such as, for example heparin, hyaluronic acid; and poly(ethylene glycol)(PEG).

1. PEAs Combined with Heparin or Hyaluronic Acid

In some embodiments, a PEA can be combined with a glycosaminoglycan such as, for example, heparin or hyaluronic acid as a graft or block copolymer. For example, a block-copolymer of PEA and heparin can be prepared by combining an amino-terminated PEA with an aldehyde-terminated heparin. An example of an aldehyde-terminated heparin is represented by a formula (XIX):

quently reduced with NaCNBH$_3$ to produce the following PEA-heparin copolymer structure represented by formula (XX):

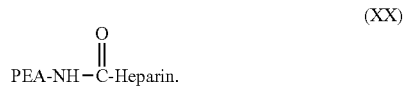

(XX)

One method of preparing the amino-terminated PEA comprises deviating from a one-to-one stoichiometry between the sum of the amino-terminated subunits and the diacids or diacid derivatives. To achieve the highest molecular weight, the stoichiometry of the diacids or diacid derivatives is kept at one-to-one with the sum of the amino-terminated subunits, because an excess of either component results in an amino-terminated PEA with a lower molecular weight.

Another method of preparing the amino-terminated PEA comprises keeping a one-to-one stoichiometry between the amino-terminated subunits and the diacids or diacid derivatives and the polymerization is allowed to proceed for a predetermined length of time. The polymerization is terminated by the introduction of an excess of a reactive diamine such as, for example, 1,4-butanediamine. All carboxyl endgroups are terminated and any unreacted diacids or diacid derivatives are consumed. Any low molecular weight material can be separated from the polymer by precipitating the polymer in a suitable solvent known to one of skill in the art.

In some embodiments, the methods of the present invention can be designed to produce an AB copolymer, an ABA copolymer or an ABABAB . . . multi-block copolymer by activating either one or both ends of the agent polymer and the PEA polymer. The PEA-heparin copolymer shown above is an AB-block copolymer. The AB-type copolymers result when the two polymers only have a single active end. An ABA-block copolymer can also be prepared. Copolymers of the ABA-type result where one polymer has one active end and the other polymer has two active ends. Copolymers of the ABABAB . . . -type result where both polymers have two active ends.

A block-copolymer of PEA and heparin can be prepared by combining a carboxyl-terminated PEA with an aldehyde-terminated heparin. The heparin is first activated with, for example, EDC or DCC and then combined with a large excess of adipic dihydrazide to prepare an amino-functionalized heparin. Alternatively, an aldehyde-terminated heparin can be treated with ammonia or n-butylamine in the presence of a reducing agent such as, for example, sodium borohydride (NaBH$_4$), potassium borohydride (KBH$_4$), or NaCNBH$_3$.

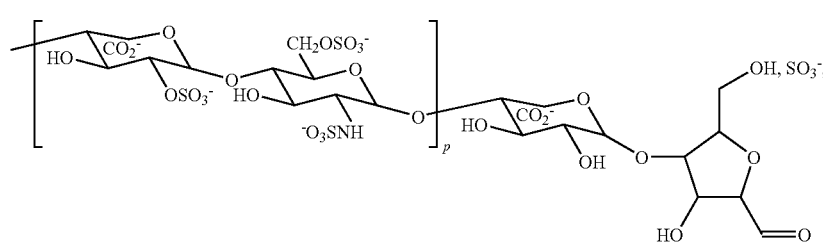

(XIX)

wherein p is an integer not equal to 0.

The aldehyde-terminated heparin can be combined with an amino-terminated PEA in a DMF/water solvent and subse- The carboxyl-terminated PEA is activated with, for example, EDC or DCC, and combined with the amino-functional heparin.

It should be appreciated that, in some embodiments of the present invention, the agent may be any biobeneficial agent that can enhance the biocompatibility or non-fouling properties of a PEA polymer. For example, hyaluronic acid can be a polymeric agent used to form a PEA-hyaluronic acid copolymer. Hyaluronic acid has free carboxyl groups, so an aldehyde-terminated hyaluronic acid can be made, for example, by oxidizing hyaluronic acid with nitrous acid or periodate. The aldehyde-terminated hyaluronic acid can then be combined with a PEA as described above.

A PEA that is both carboxyl-terminated and amino-terminated can be analyzed using standard analytical techniques to determine a ratio of carboxyl groups to amino groups. Knowing this ratio will allow one skilled in the art to decide whether to connect the polymer agent to the amino ends of the PEA or to the carboxyl ends of the PEA. A skilled artisan can protect the amino groups on the PEA with, for example, acetic anhydride to reduce undesirable side conjugation when combining a carboxyl-terminated PEA with an aldehyde-terminated heparin.

2. PEAs Combined with Poly(Ethylene Glycol)

A block copolymer of PEA and PEG can be prepared using a variety of techniques. In one embodiment, an amino-terminated PEA can be combined with a carboxyl-terminated PEG (Nektar Corp.) in the presence of, for example, EDC or DCC to form the following structure represented by a formula (XXI):

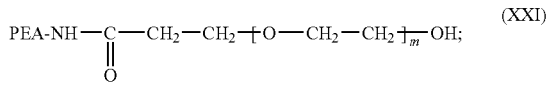

wherein m is an integer not equal to 0.

In another embodiment, either a succinimidyl derivative of mPEG (Nektar Corp.) or an isocyanate-terminated mPEG (Nektar Corp.) can be reacted with an amino-terminated PEA under conditions known to those of skill in the art. In another embodiment, the carboxyl group of a carboxyl-terminated PEA can be activated with, for example, EDC or DCC and combined with an amino-terminated mPEG (Nektar Corp.)

In another embodiment, an amino-terminated mPEG can be combined with a high molecular weight PEA in the presence of an acid or base catalyst through amination of ester groups in a high molecular weight PEA. In another embodiment, an amino-terminated PEA can be combined with a methacrylate-terminated mPEG (Nektar Corp.) in the presence of an initiator capable of undergoing thermal or photolytic free radical decomposition.

Examples of suitable initiators include benzyl-N,N-diethyldithiocarbamate or p-xylene-N,N-diethyldithiocarbamate. In another embodiment, an amino-terminated PEA can be combined with ethylene oxide in a living polymerization reaction, which is an unterminated anionic polymerization kept alive and controlled by maintaining a pure system. A living polymerization reaction can be killed through addition of a terminating agent such as, for example, water.

Figure 11A:
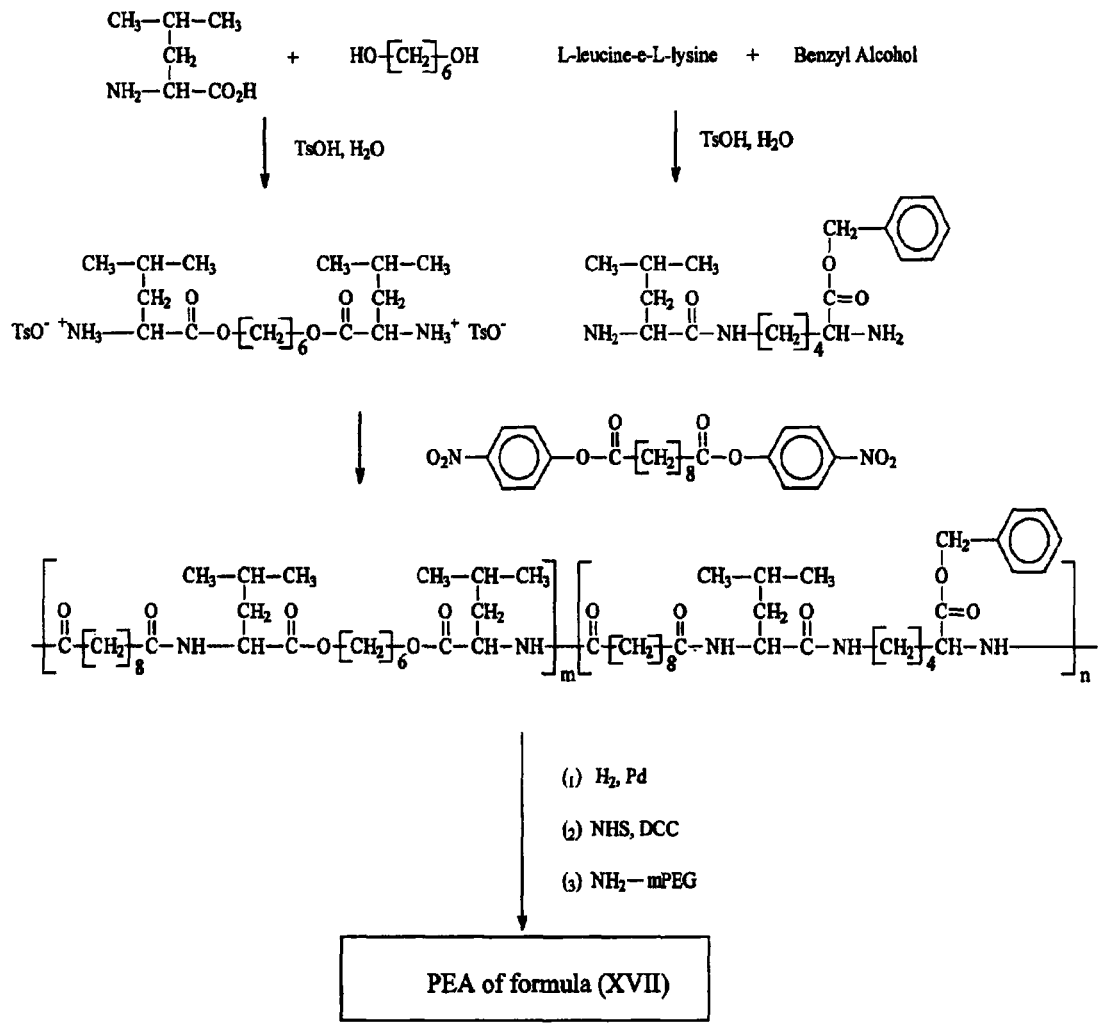
FIGS. 11a and 11b illustrate proposed reaction mechanisms for the preparation of poly(ester amides), according to some embodiments of the present invention.
Figure 11B:
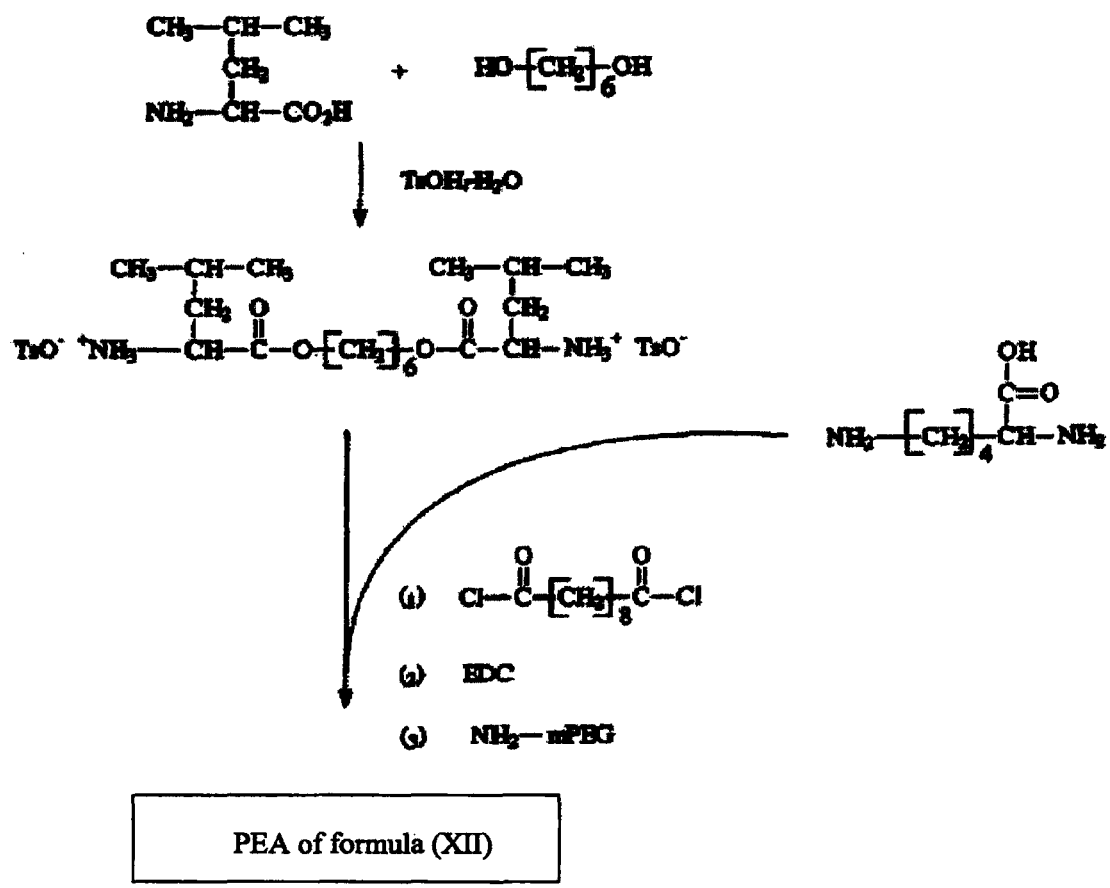

Without intending to be bound by any theory or mechanism of action, FIGS. 11a and 11b illustrate proposed reaction mechanisms for the preparation of poly(ester amides) according to some embodiments of the present invention. The following examples are provided to further illustrate embodiments of the present invention.

EXAMPLE 1

The PEA of formula (XVII) can be prepared according to the following procedure:

Method of Preparing of L-Leucine-ε-L-Lysine Benzyl Ester-2TosOH

L-leucine-ε-L-lysine-HCl (New England Peptide, Inc.) (73.86 gm, 0.25 mole), p-toluenesulfonic acid (152.15 gm, 0.80 mole), benzyl alcohol (100.9 ml, 0.97 mole), and 200 ml of benzene is added to a 1 liter reaction flask equipped with a mechanical stirrer, Dean Stark trap, thermometer and argon inlet. The mixture is heated to 80° C. for 8 hours, and condensate is collected in the Dean Stark trap. The mixture is transferred to a 2 liter flask, and 1 liter of ethyl acetate is added to the mixture with stirring. The mixture is stored overnight at 4° C., and L-Leucine-ε-L-Lysine Benzyl Ester-2TosOH and is isolated by filtration.

Method of Preparing co-poly-{[N,N'-sebacoyl-bis-(L-leucine)-1,6-hexylene diester]-[N,N'-sebacoyl-L-leucine-L-lysine mPEG amide]}

Dry triethylamine (61.6 ml, 0.44 mole) is added to a mixture of di-p-toluenesulfonic acid salt of bis-(L-leucine)-1,6-hexylene diester (120.4 gm, 0.18 mole), di-p-toluenesulfonic acid salt of L-leucine-ε-L-lysine benzyl ester (13.863 gm, 0.02 mole), and di-p-nitrophenyl sebacinate (88.88 gm, 0.2 mole) in dry DMAC (110 ml). The mixture is stirred and heated at 80° C. for 12 hours. The mixture is then cooled to room temperature, diluted with ethanol (300 ml), and poured into 1 liter of water.

The polymer is separated, washed with water, and vacuum dried. A free carboxyl group is generated by hydrogenolysis over a palladium catalyst. Ethanol (1200 ml) and the polymer (100 mg) is added to a 2 liter flask with a palladium on carbon catalyst (5 gm) (Aldrich). Hydrogen is bubbled and stirred through the mixture for 24 hours, and the palladium on carbon catalyst is separated by centrifugation to leave an isolated solution.

The isolated solution is added to hexane/ethyl acetate (10 liters of a 50/50 mixture) with stirring to precipitate co-poly-{[N,N'-sebacoyl-bis-(L-leucine)-1,6-hexylene diester]-[N,N'-sebacoyl-L-leucine-L-lysine]}. The polymer is filtered, dissolved (50 gm) in THF (1500 ml) in a 2 liter flask with stirring and an argon purge, and then combined with N-hydroxysuccinimide (1.32 gm, 0.0115 mole) and dicyclohexylcarbodiimide (2.37 gm, 0.0115 mole). The combination is stirred for 24 hours at ambient temperature and filtered to remove 1,3-dicyclohexylurea.

The filtered solution is combined with an amino-terminated mPEG (MW 5000, 46 gm, 0.0092 moles) (Nektar Corp.) in a 2 liter flask and stirred for 6 hours under argon. The co-poly-{[N,N'-sebacoyl-bis-(L-leucine)-1,6-hexylene diester]-[N,N'-sebacoyl-L-leucine-L-lysine mPEG amide]} is precipitated by slow addition of the solution into hexane/ethyl acetate (50/50) with stirring. While not intending to be bound by any theory or mechanism of action, a proposed reaction mechanism for the preparation of the poly(ester amide) (PEA) of formula (XVII) according to one embodiment of the present invention is illustrated in FIG. 11a.

Due to its PEG content, this PEA polymer will have an improved non-fouling property compared to a PEA without PEG. However, this hydrophilic PEG will also increase the water swelling of the polymer. For the delivery of low to medium molecular weight drugs this will make the polymer amenable for the delivery of very hydrophobic drugs such as paclitaxel, or to be used as a biobeneficial topcoat.

EXAMPLE 2

The copolymer represented by formula (XII) can be prepared in a manner analogous to the method used to prepare the copolymer represented by formula (XVII) by replacing the L-leucine-ε-L-lysine-HCl with L-lysine HCl. While not intending to be bound by any theory or mechanism of action, a proposed reaction mechanism for the preparation of the PEA of formula (XII) according to one embodiment of the present invention is illustrated in FIG. 11b.

EXAMPLE 3

The PEA of formula (XV) can be prepared according to the following procedure:

Method of Preparing co-poly-{[N,N'-sebacoyl-bis-(L-leucine)-1,4-butylene diester]-[N,N'-sebacoyl-L-lysine-4-carboxy-TEMPO anhydride]}

Dry triethylamine (61.6 ml, 0.44 mole) is added to a mixture of a di-p-toluenesulfonic acid salt of bis-(L-leucine)-1,4-butylene diester (118.82 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter).

The polymer is separated, washed with water, and dried under vacuum. A free carboxyl group can be generated by hydrogenolysis over a palladium catalyst. Ethanol (1200 ml) is combined with the polymer (100 gm) and a palladium on carbon catalyst in a 2 liter flask (Aldrich). Hydrogen is bubbled and stirred through the solution for 24 hours. The palladium on carbon is separated by centrifugation to leave an isolated solution.

The isolated solution is slowly added to hexane/ethyl acetate (10 liters, 50/50) with stirring to precipitate co-poly-{[N,N'-sebacoyl-bis-(L-leucine)-1,6-hexylene diester]-[N,N'-sebacoyl-L-lysine]}. The polymer (50 gm) is filtered, dissolved and stirred in dry 1,1,2-trichloroethane (1600 ml) in a 2 liter flask, and acetic anhydride (2.24 gm, 0.022 mole) and 4-carboxyl-TEMPO (4.01 gm, 0.02 mole) is added to the 2 liter flask.

The mixture is distilled under vacuum to remove DMF at 80° C. and a sufficient amount of heat is applied to achieve a distillation rate of about 5 ml/min. The solution is stirred for two hours, cooled to room temperature, and the co-poly-{[N,N'-sebacoyl-bis-(L-leucine)-1,4-butylene diester]-[N,N'-sebacoyl-L-lysine-4-carboxy-TEMPO anhydride]} is precipitated by slow addition of the solution to hexane/ethyl acetate (4 liters, 50/50) with stirring.

EXAMPLE 4

The PEA of formula (XVIII) can be prepared according to the following procedure:

Method of Preparing Conjugate of Estradiol and 3,9-diethylidene-2,4,8,10-tetraoxaspiro-[5,5]-undecane (DETOSU)

Dry THF (40 ml) is combined with DETOSU (5 gm, 0.0236 mole) and six drops of 1% p-toluenesulfonic acid in THF in a 100 ml flask. A solution of estradiol (6.42 gm. 0.0236 mole) in THF (20 ml) is slowly added with stirring for over an hour. The estradiol-DETOSU conjugate is isolated by rotary evaporation.

Method of Preparing bis-(L-leucine)-1,3-propylene diester-2-one

L-leucine (32.80 gm, 0.25 mole), p-toluenesulfonic acid (104.6 gm, 0.55 mole), 1,3-dihydroxy acetone dimer (22.53 gm, 0.125 mole), and 200 ml of benzene are added to a 1 liter flask. The solution is heated at 80° C. for 8 hours, and condensate is collected in a Dean Stark trap. The solids are separated from the solvents by rotoevaporation, rinsed in Buchner funnel with water (2, 1 liter portions) and dried in a vacuum oven.

Method of Preparing co-poly-{[N,N'-sebacoyl-bis-(L-leucine)-1,4-butylene diester]-[N,N'-sebacoyl-bis-L-leucine-1,3-propylene diester-2-one]}

Dry triethylamine (61.6 ml, 0.44 mole) is added to a mixture of a di-p-toluenesulfonic acid salt of bis-(L-leucine)-1, 4-butylene diester (118.82 gm, 0.18 mole), a di-p-toluenesulfonic acid salt of bis-(L-leucine)-1,3-propylene diester-2-one (13.20 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter). The polymer is separated, washed with water, and dried under a vacuum.

The polymer (80.35 gm), dry THF (250 ml), sodium cyanoborohydride (10.49 gm, 0.167 mole), and p-toluenesulfonic acid (6 drops of a 1% solution) in THF is added to a 500 ml flask. The mixture is stirred for two hours at ambient temperature, poured into chloroform (500 ml), and extracted with 3 portions of aqueous sodium bicarbonate (250 ml, 1M portions). Chloroform is removed by rotoevaporation and the remaining solvent is removed by drying overnight in a vacuum oven at ambient temperature. The polymer (60 gm), dry THF (250 ml), and the estradiol-DETOSU conjugate (6.64 gm, 0.0137 mole) is added to a 500 ml flask and stirred at room temperature for two hours. The polymer is precipitated by slow addition of the solution into hexane/ethyl acetate (2 liters, 50/50) with stirring.

EXAMPLE 5

Method of Preparing an Amino-terminated PEA or a Carboxyl-terminated PEA

The monomers used in a preparation of PEA provide a roughly 50/50 distribution between amino and activated carboxy-terminated chains at any point during the polymerization. Amino-terminated PEAs can be prepared using a biocompatible, low molecular weight chain-stopper, 1,4-diaminobutane (putrescine) that is added in a large excess to terminate all chains with amino groups at the end of the polymerization, or when the polymerization has reached the desired molecular weight.

Carboxyl-terminated PEAs can be prepared by several methods. In one method, a dicarboxylic acid compound such as, for example, di-p-nitrophenyl sebacinate, can be combined with the PEA in excess. This embodiment is simple, but it has a potential drawback of lowering the final molecular weight of the polymer. Another method is to further derivatize a PEA containing a 50/50 distribution of amino-terminated and activated-carboxyl-terminated chains by reacting the PEA with a reagent such as, for example, succinic anhydride, to convert amino groups to carboxyl groups.

Method of Preparing an Amino-terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 4 hours, at which point 1,4-diaminobutane (15 gm, 0.17 mole) is added and the mixture is stirred at 80° C. for an additional hour. The solution is cooled to room temperature, diluted with ethanol (300 ml), and poured into a phosphate buffer (2 liters, 0.1 M, pH 7).

The polymer is collected by filtration, suspended in chloroform (1 liter), and extracted with 3 portions of phosphate buffer (0.1 M, pH 7, 1 liter portions). The chloroform is removed by rotary evaporation, and the amino-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature.

Method of Preparing an Carboxy-terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 4 hours, at which point succinic anhydride (17 gm, 0.17 mole) is added and the mixture is stirred at 80° C. for an additional hour.

The solution is cooled to room temperature, diluted with ethanol (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotoevaporation, and the carboxy-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature.

This preparation can result in a polymer wherein all of the endgroups are carboxyl, and some of the endgroups are still activated with a p-nitrophenol group. This group may be suitable for subsequent coupling steps such as with, for example, an amino-terminated moiety. If it is desired to convert all endgroups to free carboxylic endgroups, the following steps would be inserted into the synthesis: after the addition of the succinic anhydride and stirring for one hour, L-leucine (11.2 gm, 0.085 mole) and triethylamine (8.59 gm, 0.085 mole) would be added and stirred for an additional hour.

EXAMPLE 6

Method of Preparing a PEA-heparin Conjugate by Combining Heparin with an Amino-terminated PEA A PEA-heparin conjugate can be prepared by connecting an amino-terminated PEA with an aldehyde-terminated heparin formed by oxidative cleavage of heparin. An amino-terminated PEA (50 g) is added to a reactor containing DMAC/water (1 liter, 40:1) under nitrogen. An aldehyde-terminated heparin (7.5 g) and cyanoborohydride (0.2 g; 3.2 mmol) is added to the solution and heated to 60° C. for 12 hours under nitrogen, cooled to room temperature, and added dropwise to methanol. The PEA-heparin conjugate is filtered, washed with 3 portions of water (250 mL portions), and dried under vacuum.

Alternate Method of Preparing a PEA-heparin Conjugate by EDC Coupling of a D-glucuronic Acid or L-iduronic Acid Functionality of the Heparin in a DMAC/Water Medium Heparin (20 g) is combined with a DMAC/water solution (450 g) and N-(3'-dimethylaminopropyl)-N'-ethylcarbodiimide (0.2 g, 1.0 mmol). The solution is stirred at room temperature for 2 hours under nitrogen, and the PEA-amine (50 g) is added to the DMAC/water solution (40/1; 500 g) and mixed at pH 4.75 for 4 hours. The solution is neutralized with sodium hydroxide (0.1 M) to pH 7.5 and stirred overnight under nitrogen. The PEA-heparin conjugate is precipitated by addition of the solution into THF, filtered and washed with water.

EXAMPLE 7

Method of Preparing a PEA-PEG Conjugate with an Amino-terminated PEA

An amino-terminated PEA can be PEGylated by aldehyde coupling/imine reduction, carbodiimide coupling of a carboxyl terminated PEG, and maleimide coupling of a PEG-maleimide to an amine terminated PEA.

An amino-terminated PEA can be conjugated to PEG by aldehyde coupling/imine reduction. A PEA (50 g) is dissolved in anhydrous DMAC (230 g) in the coupling of PEG to amino-terminated PEA. A PEG-butyraldehyde (MW 1000-50,000, 7.5 g) is combined with sodium cyanoborohydride (1.0 g) and stirred overnight at room temperature under nitrogen. The polymer is precipitated by addition of the solution with stirring in methanol, redissolved in DMAC, reprecipitated in water, and dried under vacuum.

An amino-terminated PEA can be conjugated to PEG by carbodiimide coupling of a carboxyl terminated PEG using DCC/NHS coupling. An amino-terminated PEA (50 g) is added to anhydrous THF (116 g; 1-35% w/w). Anhydrous THF (116 g) and carboxyl-terminated PEG (10 kD, 7.0 g, 0.7 mmol), dicyclohexylcarbodiimide (0.15 g; 7.1 mmol) (DCC) is added to a reactor containing N-hydroxysuccinimide (0.10 g/8 mmol) (NHS) to form a mixture. The mixture is stirred under nitrogen for 2 hours at room temperature, and the amino-terminated PEA solution is added to the mixture in a dropwise manner, stirred overnight at room temperature, and added dropwise to methanol to form a PEA-PEG precipitate. The precipitate is filtered and dried under vacuum.

EXAMPLE 8

A medical article with two layers was fabricated to comprise everolimus by preparing a first composition and a second composition, wherein the first composition was an agent layer comprising a matrix of PEA and agent, and the second composition was a PEA topcoat layer. The first composition was prepared by mixing about 2% (w/w) co-poly-{[N,N'-sebacoyl-bis-(L-leucine)-1,6-hexylene diester]-[N,N'-sebacoyl-L-lysine benzyl ester]} ("example PEA") and about 0.5% (w/w) everolimus in absolute ethanol, sprayed onto a surface of a bare 12 mm VISION™ stent (Guidant Corp.) ("example stent") and dried to form a coating.

An example coating technique comprised spray-coating with a 0.014 fan nozzle, a feed pressure of about 0.2 atm and an atomization pressure of about 1.3 atm; applying about 20 μg of wet coating per pass; drying the coating at about 50° C. for about 10 seconds between passes and baking the coating at about 50° C. for about 1 hour after the final pass to form a dry agent layer. The agent layer was comprised of about 428 μg of PEA and about 107 μg of everolimus. The second composition was prepared by mixing about 2% (w/w) of the example PEA in absolute ethanol and applied using the example coating technique. The topcoat layer contained about 300 μg of the example PEA. The total weight of the coating was about 835 μg.

EXAMPLE 9

A medical article with three layers was fabricated to comprise everolimus by preparing a first composition, a second composition and a third composition. The first composition was a primer layer of PEA. The second composition was a pure agent layer, and the third composition was a topcoat layer of PEA.

The first composition was prepared by mixing about 2% (w/w) of the example PEA in absolute ethanol and applied onto the surface of the example stent using the example coating technique to form a dry primer layer. The dry primer layer contained about 100 μg of the example PEA. The second composition was prepared by mixing about 2% (w/w) everolimus in absolute ethanol and applied to the primer layer using the example coating technique to form a pure agent layer comprising about 107 μg of everolimus. The third composition was prepared by mixing about 2% (w/w) of the example PEA in absolute ethanol and applied using the example coating technique to form a topcoat layer comprising about 300 μg of the example PEA. The total weight of the coating was about 507 μg.

EXAMPLE 10

The coatings prepared and formed in Examples 8 and 9 were tested for total recovery of the bioactive agent, which is a measure of the percentage of bioactive agent extracted from the stent. The effects of sterilization were determined. A total of 32 stents were coated as described in Examples 8 and 9: 16 stents were coated as described in Example 8, wherein 8 stents were sterilized with electronic beam sterilization, and 8 stents were not sterilized; 16 stents were coated as described in Example 9, wherein 8 stents were sterilized using electronic beam sterilization, and 8 stents were not sterilized.

The coated stents were placed in a volumetric flask with acetonitrile comprising about 0.02% (w/w) butylated hydroxytoluene antioxidant ("extraction solvent") and sonicated for about 30 minutes to yield an extract of bioactive agent. The extract was analyzed with high pressure liquid chromatography (Waters 2690 HPLC system equipped with an analytical pump, a YMC Pro C18 separation column with an ultra-pure, silica-based adsorbent with 3 μm particles, an automatic sampler, and a 996 PAD (photodiode array detector) maintained at about 40° C.) ("the example HPLC method"). The mobile phase was fed into the column at a flow rate of about 1 ml/min and comprised about 71% (w/w) acetonitrile in 20 mM ammonium acetate solution.

The sterilized stents of Example 8 released about 91% of the everolimus, whereas the non-sterilized stents of Example 8 released about 100% of the everolimus. The sterilized stents of Example 9 released about 89% of the everolimus, whereas the non-sterilized stents of Example 9 released about 96% of the everolimus.

EXAMPLE 11

The coatings prepared and formed in Examples 8 and 9 were tested for in vitro release of everolimus. The in vitro conditions were simulated in a buffer solution containing TRITON® X 100 and a porcine serum.

The simulations involved placing the coated stents on a VanKel Bio-Dis release rate tester (Varian, Inc.) and dipping the stents at a rate of 40 dips per minute into about 7 ml of 10 mM phosphate buffer saline solution (pH=7.4) containing about 1% (w/w) TRITON® X-100 (Sigma-Aldrich Corp.) at a temperature of about 37° C. The test was conducted in predetermined time increments of about 1, 2, 6, 9, 24, and 29 hours, and the amount of everolimus was measured using the example HPLC method. A fresh buffer solution was used for each measurement.

Figure 12:
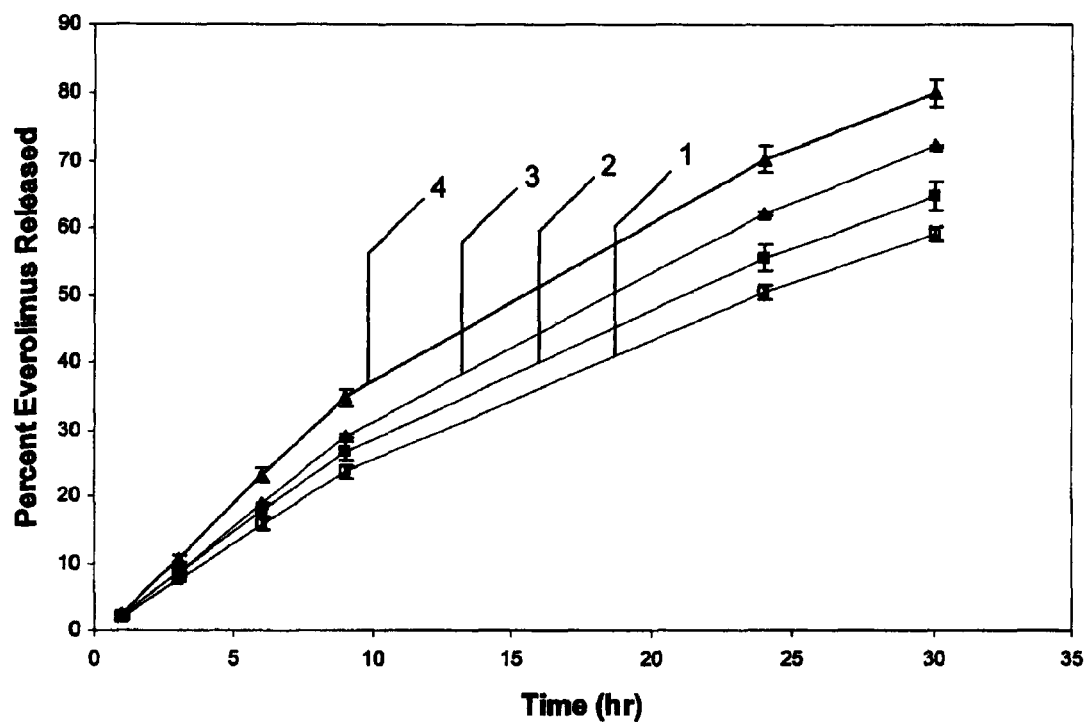
FIG. 12 illustrates the percent everolimus released in a buffer solution containing TRITON® X-100 from stent coatings that were designed according to embodiments of the present invention.

FIG. 12 illustrates the percent everolimus released in a buffer solution containing TRITON® X-100 from stent coatings that were designed according to embodiments of the present invention. Curve 1 illustrates the everolimus released from the non-sterile stent coatings of Example 8. Curve 2 illustrates the everolimus released from the sterile stent coatings of Example 8. Curve 3 illustrates the everolimus released from the non-sterile stent coatings of Example 9. Curve 4 illustrates the everolimus released from the sterile stent coatings of Example 9. The release rate profiles were uniform, and the coatings of Example 8 released everolimus at a slower rate than the coatings of Example 9. Sterilization increased the release rate by about 10 to 25% in the coatings of Example 9 and by about 10 to 15% in the coatings of Example 8.

The porcine serum simulations involved the same method and replaced the buffer solution containing TRITON® X-100 with about 10 ml of porcine serum containing about 0.1% (w/w) sodium azide. The used porcine serum was replaced with the fresh porcine serum every 8 hours, and the temperature of the solution was maintained at about 37° C. The amount of everolimus remaining on the stents after 24 hours was measured using the example HPLC method. The amount of everolimus released was calculated by subtracting the amount of everolimus remaining on the stent from the amount of everolimus initially deposited on the stent. Table 1 contains a summary of the release rate results.

| Example | Sterilized (S) Non-sterilized (NS) | Average In Vitro Release of Everolimus (over 24 hours, at 37° C., % ± std. dev. (w/w)) | |
|---|---|---|---|
| | | TRITON ® X-100 Buffer Solution | Porcine Serum |
| 8 | S | 55.63 ± 2.06 | 33.35 ± 1.99 |
| 8 | NS | 50.41 ± 1.05 | 31.68 ± 1.22 |
| 9 | S | 70.30 ± 1.98 | 37.95 ± 5.46 |
| 9 | NS | 62.34 ± 0.27 | 34.96 ± 1.81 |

Table 1 illustrates that the amount of everolimus released over 24 hours from the coatings of Example 8 was less than that released from the coatings of Example 9 in both the buffer solution containing TRITON® X-100 and in the porcine serum. The amount of everolimus released from the sterilized coatings was higher than that released from the corresponding non-sterilized coatings in both cases.

EXAMPLE 11

A lumped-parameter mass transport model was developed to predict the rate of release of agents from a coating. As described above, it was assumed that the dissolution and diffusion of an agent within a polymeric matrix can be lumped into an effective diffusivity for a given polymeric matrix design to describe the mass transport of the agent within the coating. It was also assumed that the transport of the agent in the coating may occur through Fickian diffusion, as derived and described above. Using these assumptions, the transport of the agent through a polymeric matrix can be predicted by, for example, the following system of equations:

$$\frac{\partial \overline{C}}{\partial \overline{t}} = \frac{\partial^2 \overline{C}}{\partial \overline{x}^2}$$

IC: $\overline{C}(0, \overline{x}) = f(\overline{x})$ for $0 \leq \overline{x} \leq 1$ BC1: $\left.\frac{\partial \overline{C}}{\partial \overline{x}}\right|_{\overline{t},0} = 0$ BC2: $\left.\frac{\partial \overline{C}}{\partial \overline{x}}\right|_{\overline{t},1} = -\frac{K_m L}{D}(K\overline{C}|_{\overline{t},1} - \overline{C}|_{\overline{t},bulk})$;

where, in this example,
t is time in sec;
$\overline{t}$ is dimensionless time ($\overline{t}=t/(L^2/D)$);
L is a thickness of the coating in cms;
D is a diffusivity in $cm^2/sec$;
$\overline{x}$ is a dimensionless length (actual length/L);
$\overline{C}$ is a dimensionless concentration;
$\overline{C}|_{\overline{t},1}$ is a dimensionless concentration at the surface of the coating at any time;
$\overline{C}|_{\overline{t},bulk}$ is a dimensionless concentration outside the stent coating at any time;
$K_m$ is a mass transfer coefficient in (cm/sec); and,
K is a dimensionless partition coefficient at equilibrium.

Generally speaking, the mass of the agent in the polymeric matrix at any time t is given by $$M(\overline{t}) = \int_0^1 C(\overline{x}, \overline{t}) A \, d\overline{x} = A \int_0^1 C(\overline{x}, \overline{t}) \, d\overline{x};$$

where M is the amount of agent (in µg) in the polymeric matrix at any time $\overline{t}$; and,
A is the stent surface area (in $cm^2$).

For a matrix configuration containing an agent reservoir and a top coat, the amount of agent in the matrix at any time t is given by the following analytical model:

$$\frac{M}{M_0} = \sum_{n=0}^{\infty} (-1)^n \frac{4}{(2n+1)\pi x^*} \sin\left(\frac{(2n+1)\pi x^*}{2}\right)\left(1 - \exp\left(-\frac{(2n+1)^2 \pi^2 Dt}{4L^2}\right)\right);$$

where $x^* = \frac{\text{Agent reservoir thickness}}{\text{Total coating thickness }(L)}$;

Total coating thickness =
(agent reservoir thickness) + (top-coat thickness); and, $M_0$ is the initial amount of agent in the matrix.

Figure 13:
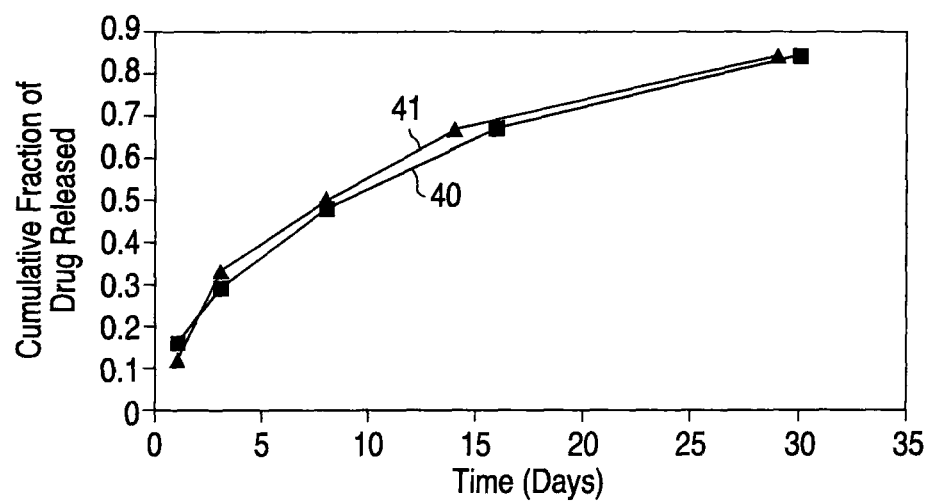
FIG. 13 demonstrates the accuracy of fit for an analytical model used to predict release rates of agents from polymeric matrices according to some embodiments of the present invention.

FIG. 13 demonstrates the accuracy of fit for an analytical model used to predict release rates of agents from polymeric matrices according to some embodiments of the present invention. The cumulative amount of agent released according to model predictions was fit to published experimental data by iterating values of $L^2/D$ until a very good fit was obtained between the model prediction 40 and the in vivo experimental data 41; an example of a goodness-of-fit test known to one of skill in the art for such analyses is the Chi-Square Goodness-of-Fit test. The diffusivity was then calculated from this value of $L^2/D$, since the coating thickness was known. The diffusivity was then used to compute the cumulative amount of agent released in-vivo for a clinically tested system. The in-vivo experimental data 41 fit well to the model predictions 40 using statistical methods known to one of skill in the art.

EXAMPLE 12

Figure 14:
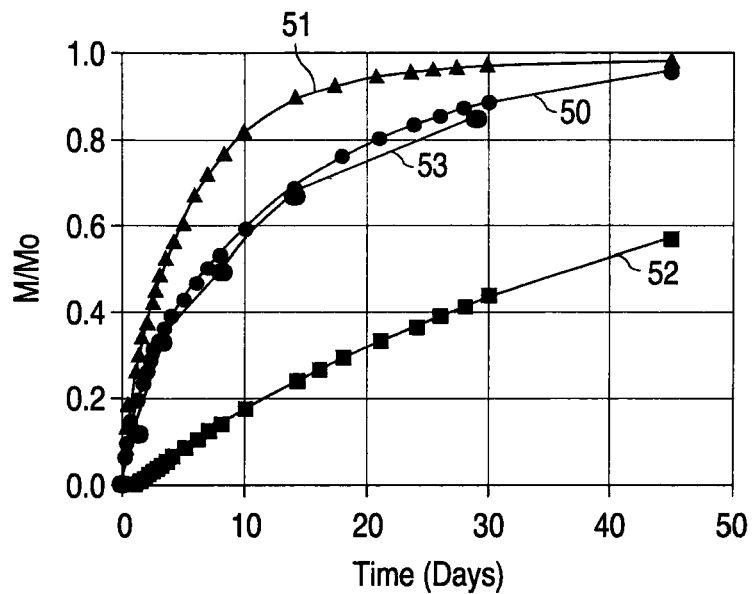
FIG. 14 shows the fraction of agent released as a function of time for three different coating configurations according to some embodiments of the present invention.
Figure 15:
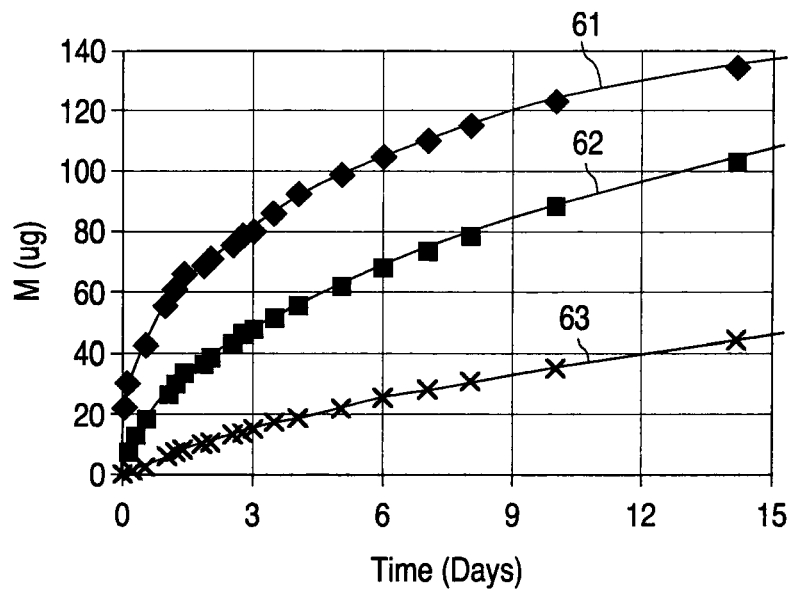
FIG. 15 shows the effect of agent-to-polymer ratios on agent release from a polymeric matrix according to some embodiments of the present invention.

The agent diffusivity in the polymeric matrix provided valuable information for evaluating and predicting the effects of coating design parameters on agent release. FIG. 14 shows the fraction of agent released as a function of time for three different coating configurations according to some embodiments of the present invention. The different coating configurations were (1) a polymeric matrix reservoir (coating containing an agent) with no topcoat 51; (2) the same reservoir with a topcoat 52; and (3) the coating that provided the published experimental data 53 used to fit the model 50. The fastest release rate was observed for the polymeric matrix reservoir with no top coat 51. The addition of the topcoat lowers the release rate by acting as a rate limiting membrane.

The amount of agent released from a polymeric matrix is designated in FIG. 14 by "M", and can be measured in vitro in a release medium. In the present example, the release medium was a buffered solution containing TRITON as a surfactant. The value of M as measured in the release medium can be verified by extracting the residual agent, "Ms" out of the spent or partially spent polymeric matrix, where M+Ms=Mo, and Mo is the initial amount of agent in the polymeric matrix.

Note that some losses in agent occur due to handling, degradation, etc., such that usually M+Ms<Mo. These losses should be taken into account in all calculations through standardization techniques, such as those known to one of skill in the art. One method of obtaining Mo is to extract all of the agent out of a polymeric matrix before any exposure of the matrix to a release medium and assign this value of Mo as the standardized value for that particular batch of polymeric matrices. The value of M for an in vivo system can be determined by measuring Mo and Ms, where M is the difference between those measured values.

The method was successfully applied to a stent coating ("reservoir") containing poly(vinylidene fluoride-co-hexafluoropropylene) and everolimus at a dose of 100 µg/$cm^2$ to measure the release rates of the everolimus in vivo. The theoretical release rate results provided an excellent fit to the experimental release rate results over a 30 day release period. The fitting parameters from the 100 µg/$cm^2$ dose were used to evaluate the same stent coating having an additional heparin coating applied on top of the reservoir, as well as to subsequently predict several other doses. For example, the everolimus was loaded into the reservoir layer at 10 µg/$cm^2$, 20 µg/$cm^2$, and 45 µg/$cm^2$, and again an excellent fit between the theoretical release rate and the experimental release rate results were shown over a 30 day release period.

EXAMPLE 13

Release rates for various IC profiles can be determined from the model calculation, which provides one of skill in the art with a means to design IC profiles within polymeric matrices of choice. The IC profiles described above represent the relationship between concentration and position within a polymeric matrix. In effect, each IC profile is a continuum of changing agent-to-polymer ratios, so an evaluation of the effect of agent-to-polymer ratios can be used to support the premise that control over the shape of an IC profile of an agent within a polymeric matrix can provide control over the release rates of the agent from the polymeric matrix.

FIG. 15 shows the effect of agent-to-polymer ratios on agent release from a polymeric matrix according to some embodiments of the present invention. A model system with a higher agent-to-polymer ratio 61 has a higher release rate than a model system with a lower agent-to-polymer ratio 62. A model system with lower agent-to-polymer ratio having a topcoat 63 further lowers the release rate.

This concept was applied to an in vivo test system using a polymeric matrix comprising poly(vinylidene fluoride-co-hexafluoropropylene) and everolimus as a homogeneous mixture coated on a stent to a thickness of about 5-6 μm. Theoretical and in vivo test results for a loading of about 100 μg/cm$^2$ and for a loading of 45 μg/cm$^2$ were compared. Not only did the in vivo results show an excellent correlation to the theoretical results in each case, but the difference in release rates were significant between the different loadings, where the 100 μg/cm$^2$ loading had a higher release rate than the 45 μg/cm$^2$ loading.

The discovery that control over agent-to-polymer ratios can provide control over agent release rates provides a basis for the development of coatings with one or more predetermined IC profiles. Factors affecting the IC profiles within a coating are discussed above and are further discussed below in the context of the ensuing examples.

Selection of Materials

The coating design process involves a careful selection of materials, which include, but are not limited to, one or more polymers and one or more agents. The combination of the one or more polymers and one or more agents often involves use of a solvent.

The design of an IC profile relies, at least partially, on the behavior among the materials chosen and the resulting morphology of the polymeric matrix formed from those materials. The solubility parameters of the one or more polymers that are chosen, for example, can provide an indication of the solubility of the polymers in a solvent of choice and the miscibility between the polymers. Likewise, the solubility of the one or more agents in a particular solvent or solvent/polymer system can also be a consideration, as well as the miscibility between the one or more agents and the one or more polymers. Such considerations can help one of skill in the art to design a system while having control over the phase morphology of the system.

In one example, a system may be chosen to include polymers in dispersed phases at a percolation threshold to provide the desired agents with channels for release from the system. In this case, polymers with solubility parameters that differ enough to form separate phases would be chosen and would be combined in an appropriate ratio to reach the percolation threshold.

In another example, a system may be chosen to include an agent that is much more miscible in a particular polymer within a combination of polymers, such that the agent is primarily present in that polymer in the system. In another example, a system may be chosen such that a polymer in a combination of polymers has a much higher solubility in a particular solvent, such that the solvent can carry the agent into the polymer as the solvent is removed from the system. In another example, a system may be chosen such that the agent can be dissolved and dispersed relatively evenly throughout a polymeric matrix containing a combination of polymers regardless of whether there is a dispersed phase within the combination of polymers. In another example, other process considerations such as time, temperature, and pressure, and their effects on the behavior among the select materials are integral to the selection of the materials to use in a system.

In another example, a combination of the concepts taught in this example can be used to create a coating design with a combination of morphology characteristics.

EXAMPLE 14

A polymeric matrix of everolimus dispersed in poly(D,L-lactide) can serve as an example of how selection and placement of materials can affect release rate. A thin topcoat of poly(D,L-lactide) on the polymeric matrix containing everolimus will effectively slow down the release rate of the everolimus from the polymeric matrix significantly as a result of the hydrophobic nature of the poly(D,L-lactide).

A hydrophobic agent such as, for example, paclitaxel can be encapsulated in a hydrophobic polymer or copolymer such as, for example, a poly(styrene-co-isobutylene-co-styrene) triblock copolymer. At a given loading of agent, the release rate of agent from such a combination can be significantly lower than that of an agent from a more hydrophilic polymer such as, for example, poly(ethylene-co-vinyl alcohol).

Selection of Process Conditions

As discussed above, the IC profile can be depend on a variety of process conditions, which include, for example, the way a composition is applied, dried, and possibly annealed. Forming a medical device or coating with a desired IC profile can include creating the IC profile as the compositions containing agent are applied. In one example, an IC profile of a coating can be developed one pass at a time. The agent concentration can be increased or decreased on each pass to create any IC profile that may be desired, wherein the IC profile can be a relatively continuous distribution of agent. Such a distribution may provide a release profile with smooth, or substantially smooth, transitions in agent release rates.

The desired IC profile can be any one or any combination of profiles. It should be appreciated that other process conditions such as, for example, the time, temperature, and pressure of subsequent steps such as, for example, drying can alter the IC profile. A freeze drying or critical-point drying process may be chosen, for example, to remove solvent without altering the IC profile. In another example, a series of layers can be applied to develop an IC profile, wherein each layer can be applied through multiple passes and have a constant IC profile that differs from adjacent layers. The resulting medical device or coating would contain a series of layers that provide an incremental distribution of agent. Such a distribution may provide a release profile that has distinct changes, such as steps, in agent release rates. These steps can be large, small, or a combination thereof, by design.

Forming a medical device or coating with a desired IC profile can include creating the IC profile after the compositions containing agent have been applied. In one example, an agent that migrates with a solvent can be profiled by controlling the rate of solvent migration. The rate of solvent migration can be controlled by altering the pressure and/or temperature in the environment of a solvent removal process such as, for example, drying. Such control of the pressure and/or temperature can allow for indirect control of the pattern that is taken by an agent concentration relative to position in a polymeric matrix. The IC profiles can then be designed to take on virtually any profile desired such as, for example, a predetermined wave profile that can provide a pulsed administration of a desired agent.

EXAMPLE 15

The development of IC profiles can implement boundary condition control through, for example, use of solvent vapor, humidity, temperature, and/or pressure to establish a diffusion medium for an agent in a polymeric matrix. The establishment of a diffusion medium allows for the mobility of agent during processing of the polymeric matrix.

A stent can be coated with a hydrophobic agent layer that is subsequently coated with a hydrophilic polymeric matrix. Movement of the underlying hydrophobic agent layer through the hydrophilic polymeric matrix would not normally be thermodynamically favorable. However, the agent can be drawn through the hydrophilic polymeric matrix through the use of a boundary condition containing solvent vapor that can permeate the hydrophilic polymeric matrix and serve as a diffusion medium for the hydrophobic agent. The movement of the agent can also be influenced by administration of pressure and/or heat, and this administration can be constant, cyclic, or any variation discovered by one of skill in the art to create an IC profile that will provide a desired release rate of the agent in vivo.

The distribution of the agent can also have a chromatographic effect that can be altered through the selection of polymers, copolymers, metals, ceramics, additional agents combined with the foregoing, and the like. Likewise, it should be appreciated that the inverse of this example can be used to move any agent through any polymeric matrix such as, for example, the use of a high relative humidity to move a hydrophilic agent through a hydrophobic polymeric matrix.

EXAMPLE 16

A stent can be coated in a series of layers using a very low agent-to-polymer ratio for each layer. A very low agent-to-polymer ration can range, for example, from about 1/10 to about 1/50.

A theoretical modeling of the general profile illustrated in FIG. 6(b) was compared to a theoretical modeling of the inverse of that IC profile, where the assumption was that the same composition and process conditions would be employed and the diffusion coefficient would be the same or substantially the same. No topcoat was applied to either profile in this theoretical modeling study. FIG. 6(b) illustrates a positive slope, which indicates that the region of highest agent concentration is at the surface of the coating, and the region of lowest concentration would be at the surface of the medical device.

The inverse of that profile would be a negative slope, which would indicate that the region of highest concentration would be at the surface of the medical device, and the region of lowest concentration would be at the surface of the coating. The theoretical results showed a dramatic difference in release rates, where the positive slope illustrated in FIG. 6(b) had a much higher release rate than the negative slope.

The IC profiles can be obtained by varying the agent concentration in each pass, or by varying the agent concentration in each layer, which can be a series of passes. A 12 mm stent can be coated using a first pass with an agent-to-polymer ratio of about 1/10 for application of the first 200 µg, about 1/30 for application of the next 200 µg, and finally about 1/50 for application of an additional 200 µg. The effective diffusivity should remain constant in this example because of the low overall agent-to-polymer ratio. The progressive reduction in the ratio should result in an IC profile that has an initial release rate that is slow but sustainable when compared to a corresponding flat IC profile for the exact same dose.

EXAMPLE 17

PEA-TEMPO Reservoir with a Combination of Clobetasol and Everolimus

Poly(ester amide) constructs were created using blends of clobetasol and everolimus in a reservoir having a PEA-TEMPO polymer construct. Agent release was further controlled by adding a PEA-TEMPO topcoat. In this study, the effect of topcoat thickness on drug release was evaluated. The ratio of agent-to-polymer was held constant at 1:6, and the everolimus ("EVR") and clobetasol ("CLO") doses were chosen based on animal studies. Table 2 summarizes the study arms that will be used as a point of reference for the subsequent discussion of results shown in Table 3:

TABLE 2

| | | RESERVOIR | | | | | | | |
|---|---|---|---|---|---|---|---|---|---|
| Arm | Agent:Polymer | EVR Total (ug) | CLO Total (ug) | EVR Dose (ug/cm2) | CLO Dose (ug/cm2) | Total Dose (ug/cm2) | Reservoir Total (ug) | Topcoat (ug) | Total Solid (ug) |
| 1 | 1:6 | 14 | 5.6 | 25 | 10 | 35 | 137 | 200 | 337 |
| 2 | 1:6 | 14 | 5.6 | 25 | 10 | 35 | 137 | 400 | 537 |
| 2 | 1:6 | 14 | 5.6 | 25 | 10 | 35 | 137 | 600 | 737 |

Table 3 summarizes the 1-day release rate in porcine serum for each of the study arms listed in Table 2.

TABLE 3

| Arm | Sample # | Everolimus ug released | Everolimus % Release | Average release | Clobetasol ug released | Clobetasol % Release | Average % release |
|---|---|---|---|---|---|---|---|
| 1 | 29 | 4.7 | 31.2 | | 2.2 | 87.8 | |
| | 30 | 4.8 | 30.6 | | 2.3 | 86.6 | |
| | 32 | 5.3 | 35.6 | 32.5 | 2.3 | 90.6 | 88.3 |
| 2 | 7 | 1.8 | 11.8 | | 1.5 | 60.1 | |
| | 8 | 1.7 | 11.5 | | 1.5 | 59.2 | |
| | 9 | 1.9 | 12.5 | 11.9 | 1.5 | 58.5 | 59.3 |
| 3 | 1 | 1.2 | 8.1 | | 1.1 | 42.5 | |
| | 2 | 0.9 | 6.1 | | 1.0 | 41.5 | |
| | 3 | 1.5 | 9.5 | 7.9 | 1.2 | 43.6 | 42.5 |

The clobetasol release rate was faster than what was intended, but this study demonstrates that PEA-based polymers can effectively control the release rates of combination drugs, and this has been specifically shown for the combination of clobetasol and everolimus.

EXAMPLE 18

Multiple PEA-TEMPO Reservoirs with a Single Agent in Each Reservoir

Reservoirs having PEA-TEMPO constructs that contained only one agent per reservoir layer, either everolimus or clobetasol, were stacked to illustrate control of agent release. A clobetasol reservoir was placed underneath an everolimus reservoir to slow the release of clobetasol. Agent release was further controlled by adding a PEA-TEMPO construct as a topcoat layer.

The effect of the clobetasol:PEA-TEMPO ratio and topcoat thickness on drug release was observed. The everolimus:PEA-TEMPO ratio was held constant at 1:6 as shown in Table 4, and the doses of everolimus and clobetasol were chosen based on previous animal studies.

TABLE 5

| Arm | Sample | Everolimus ug released | Everolimus % Release | Average % release | Clobetasol ug released | Clobetasol % Release | Average % release |
|---|---|---|---|---|---|---|---|
| 1 | 14 | 1.9 | 14.5 | | 2.0 | 32.5 | |
| | 15 | 2.1 | 16.5 | | 2.1 | 35.0 | |
| | 16 | 1.7 | 13.4 | 14.8 | 2.1 | 36.3 | 34.6 |
| 2 | 9 | 1.9 | 14.8 | | 2.1 | 32.2 | |
| | 10 | 0.7 | 5.6 | | 1.9 | 30.8 | |
| | 11 | 3.4 | 24.8 | 10.2 | 2.0 | 32.0 | 31.7 |
| 3 | 2 | 2.9 | 21.7 | | 1.5 | 25.5 | |
| | 3 | 0.9 | 7.0 | | 1.4 | 23.1 | |
| | 4 | 1.7 | 13.6 | 14.1 | 1.2 | 21.9 | 23.5 |
| 4 | 13 | 1.5 | 11.8 | | 2.2 | 33.6 | |
| | 15 | 0.4 | 3.5 | | 1.9 | 31.3 | |
| | 16 | 0.2 | 1.3 | 5.5 | 2.0 | 31.5 | 32.1 |
| 5 | 3 | 0.9 | 7.5 | | 1.7 | 31.2 | |
| | 4 | 1.1 | 8.4 | | 1.7 | 27.3 | |
| | 5 | 5.4 | 42.5 | 8.0 | 1.5 | 25.9 | 28.1 |

Examples 17 and 18 demonstrate a "proof of concept" that PEA-based polymers can be used to control the release of clobetasol and everolimus in combination. In these examples, the agent release rates were limited to those obtained using a

TABLE 4

| | Drug-Primer | | | | Reservoir | | | | | |
|---|---|---|---|---|---|---|---|---|---|---|
| Arm | Total Agent:Polymer | CLO Total (ug) | CLO Dose (ug/cm2) | Reservoir Total (ug) | Total Agent:Polymer | EVR Total (ug) | EVR Dose (ug/cm2) | Reservoir Total (ug) | Topcoat Polymer | Topcoat (ug) | Total Solid (ug) |
| 1 | 1:6 | 6.0 | 10 | 42 | 1:6 | 14 | 25 | 98 | PEA | 500 | 640 |
| 2 | 1:6 | 6.0 | 10 | 42 | 1:6 | 14 | 25 | 98 | PEA | 600 | 740 |
| 3 | 1:6 | 6.0 | 10 | 42 | 1:6 | 14 | 25 | 98 | PEA | 700 | 840 |
| 4 | 1:4 | 6.0 | 10 | 30 | 1:6 | 14 | 25 | 98 | PEA | 600 | 728 |
| 5 | 1:8 | 6.0 | 10 | 54 | 1:6 | 14 | 25 | 98 | PEA | 600 | 752 |

Table 5 summarizes the 1-day release rate in porcine serum for each of the study arms in Table 4. The clobetasol release rate from these constructs was significantly reduced from the clobetasol release rates seen with the constructs of Table 3. Moreover, this study demonstrated that the topcoat thickness plays a bigger role in controlling the clobetasol release rate than the clobetasol:PEA-TEMPO ratio within the reservoir does. The everolimus release rates for each of the arms was within target rates based on previous studies.

PEA-TEMPO construct. Other polymers within the PEA family may be more suitable choices and include, but are not limited to the following:

(1) a PEA construct with a higher Tg than the PEA-TEMPO construct to alter the permeability and control release rate—examples can include, for example, PEAs based on L-isomers of amino acids such as, for example, the L-isomers of valine and phenylalanine; and, (2) a PEA construct chemically bonded to clobetasol, such that the clobetasol can be released only after the chemical bond has been broken. The liability of, for example, a chemical linker can be chosen to provide a desired release rate, as described in detail above.

While particular embodiments of the present invention have been shown and described, those skilled in the art will note that variations and modifications can be made to the present invention without departing from the spirit and scope of the teachings. A multitude of embodiments that include a variety of chemical compositions, polymers, agents and methods have been taught herein. One of skill in the art is to appreciate that such teachings are provided by way of example only and are not intended to limit the scope of the invention.

We claim:

1. A medical article comprising:
an agent or a combination of agents, and
a polymeric matrix comprising a polymer agent and a poly(ester amide);
wherein one of the polymer agent and the poly(ester amide) has a high $T_g$ and the other has a low $T_g$ or a very low $T_g$,
wherein the polymer agent comprises a poly(alkylene glycol) and a moiety selected from the group consisting of phosphorylcholine, poly(N-vinyl pyrrolidone), poly(acrylamide methyl propane sulfonic acid), poly(styrene sulfonate), polysaccharides, poly(ester amides), peptides, free radical scavengers, nitric oxide donors, and combinations thereof,
wherein when the poly(ester amide) has a high $T_g$, it is made by reacting a carboxyl group in the backbone of a poly(ester amide) having a low $T_g$ with a stiffening group which is

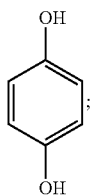

when the polymer agent has a high $T_g$, it is made by reacting a poly(alkylene glycol) bearing hydroxyl or amino end group with a stiffening group which is

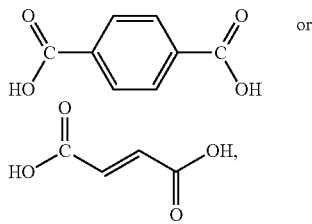 or or by reacting a poly(alkylene glycol) bearing aldehyde end group with a stiffening group which is

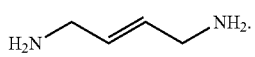

2. The medical article of claim 1, which is a medical device, a coating for a medical device, or a combination thereof.
3. The medical article of claim 1 comprising a stent.
4. The medical article of claim 1, wherein the agent comprises a component selected from a group consisting of bioactive agents, biobeneficial agents, diagnostic agents, plasticizing agents, and combinations thereof.
5. The medical article of claim 1, wherein the moiety is selected from a group consisting of phosphorylcholine, poly(N-vinyl pyrrolidone), poly(acrylamide methyl propane sulfonic acid), poly(styrene sulfonate), and combinations thereof.
6. The medical article of claim 1, wherein the poly(alkylene glycol) comprises a component selected from a group consisting of poly(ethylene glycol), poly(propylene glycol), and combinations thereof.
7. The medical article of claim 1, wherein the polysaccharide comprises a component selected from a group consisting of carboxymethylcellulose, sulfonated dextran, sulfated dextran, dermatan sulfate, chondroitin sulfate, hyaluronic acid, heparin, hirudin, and any salts and combinations thereof.
8. The medical article of claim 1, wherein the peptide comprises a component selected from a group consisting of elastin, silk-elastin, collagen, atrial natriuretic peptide (ANP), Arg-Gly-Asp (RGD), and any salts and combinations thereof.
9. The medical article of claim 1, wherein the free radical scavenger comprises a component selected from a group consisting of 2,2',6,6'-tetramethyl-1-piperinyloxy, free radical; 4-amino-2,2',6,6'-tetramethyl-1-piperinyloxy, free radical; 4-hydroxy-2,2',6,6'-tetramethyl-piperidene-1-oxy, free radical; 2,2',3,4,5,5'-hexamethyl-3-imidazolinium-1-yloxy methyl sulfate, free radical; 16-doxyl-stearic acid, free radical; superoxide dismutase mimic; and any salts and combinations thereof.
10. The medical article of claim 1, wherein the nitric oxide donor comprises a component selected from the group consisting of S-nitrosothiols, nitrites, N-oxo-N-nitrosamines, substrates of nitric oxide synthase, diazenium diolates, and any salts and combinations thereof.
11. The medical article of claim 1, wherein the agent comprises a component selected from a group consisting of rapamycin, methyl rapamycin, everolimus, pimecrolimus, 42-Epi-(tetrazoylyl)rapamycin (ABT-578), tacrolimus, and any salts and combinations thereof.
12. The medical article of claim 1, wherein the agent comprises a component selected from a group consisting of imatinib mesylate, paclitaxel, docetaxel, midostaurin, and any salts and combinations thereof.
13. The medical article of claim 1, wherein the agent comprises a component selected from a group consisting of estradiol, clobetasol, idoxifen, tazarotene, and any salts and combinations thereof.
14. The medical article of claim 1 comprising a combination of agents selected from a group consisting of everolimus and clobetasol; tacrolimus and rapamycin; tacrolimus and everolimus; rapamycin and paclitaxel; and combinations thereof.
15. The medical article of claim 1 further comprising a second polymeric matrix.
16. A method of producing a medical article comprising:
selecting an agent or a combination of agents,
forming a polymeric matrix comprising a polymer agent and a poly(ester amide),
wherein one of the polymer agent and the poly(ester amide) has a high $T_g$ and the other has a low $T_g$ or a very low $T_g$,
forming the medical article, wherein the polymer agent comprises a poly(alkylene glycol) and a moiety selected from the group consisting of phosphorylcholine, poly(N-vinyl pyrrolidone), poly(acrylamide methyl propane sulfonic acid), poly(styrene sulfonate), polysaccharides, poly(ester amides), peptides, free radical scavengers, nitric oxide donors, and combinations thereof, wherein when the poly(ester amide) has a high $T_g$, it is made by reacting a carboxyl group in the backbone of a poly(ester amide) having a low $T_g$ with a stiffening group which is

[structure: hydroquinone (1,4-dihydroxybenzene)]

when the polymer agent has a high Tg, it is made by reacting a poly(alkylene glycol) bearing hydroxyl or amino end group with a stiffening group which is

[structures: terephthalic acid or fumaric acid]

or by reacting a poly(alkylene glycol) bearing aldehyde end group with a stiffening group which is

[structure: H₂N-CH₂-CH=CH-CH₂-NH₂]

17. The method of claim 16, wherein the medical article is a medical device, a coating for a medical device, or a combination thereof.

18. The method of claim 16, wherein the medical article comprises a stent.

19. The method of claim 16, wherein the polymer agent comprises a component selected from a group consisting of bioactive agents, biobeneficial agents, diagnostic agents, plasticizing agents, and combinations thereof.

20. The method of claim 16, wherein the moiety is selected from a group consisting of phosphorylcholine, poly(N-vinyl pyrrolidone), poly(acrylamide methyl propane sulfonic acid), poly(styrene sulfonate), polysaccharides, and combinations thereof.

21. The method of claim 16, wherein the poly(alkylene glycol) comprises a component selected from a group consisting of poly(ethylene glycol), poly(propylene glycol), and combinations thereof.

22. The method of claim 16, wherein the polysaccharide comprises a component selected from a group consisting of carboxymethylcellulose, sulfonated dextran, sulfated dextran, dermatan sulfate, chondroitin sulfate, hyaluronic acid, heparin, hirudin, any salts thereof, and combinations thereof.

23. The method of claim 16, wherein the peptide comprises a component selected from a group consisting of elastin, silk-elastin, collagen, atrial natriuretic peptide (ANP), Arg-Gly-Asp (RGD), and any salts and combinations thereof.

24. The method of claim 16, wherein the free radical scavenger comprises a component selected from a group consisting of 2,2',6,6'-tetramethyl-1-piperinyloxy, free radical; 4-amino-2,2',6,6'-tetramethyl-1-piperinyloxy, free radical; 4-hydroxy-2,2',6,6'-tetramethyl-piperidene-1-oxy, free radical; 2,2',3,4,5,5'-hexamethyl-3-imidazolinium-1-yloxy methyl sulfate, free radical; 16-doxyl-stearic acid, free radical; superoxide dismutase mimic; and any salts and combinations thereof.

25. The method of claim 16, wherein the nitric oxide donor comprises a component selected from the group consisting of S-nitrosothiols, nitrites, N-oxo-N-nitrosamines, substrates of nitric oxide synthase, diazenium diolates, and any salts and combinations thereof.

26. The method of claim 16, wherein the agent comprises a component selected from a group consisting of rapamycin, methyl rapamycin, everolimus, pimecrolimus, 42-Epi-(tetrazoylyl)rapamycin (ABT-578), tacrolimus, and any salts and combinations thereof.

27. The method of claim 16, wherein the agent comprises a component selected from a group consisting of imatinib mesylate, paclitaxel, docetaxel, midostaurin, and any salts and combinations thereof.

28. The method of claim 16, wherein the agent comprises a component selected from a group consisting of estradiol, clobetasol, idoxifen, tazarotene, and any salts and combinations thereof.

29. The method of claim 16, wherein the combination of agents comprises a combination selected from a group consisting of everolimus and clobetasol; tacrolimus and rapamycin; tacrolimus and everolimus; rapamycin and paclitaxel; and combinations thereof.

30. The method of claim 16, wherein a linker or combination of linkers are used to attach the agent or combination of agents to the polymeric matrix.

31. The method of claim 16 further comprising a second polymeric matrix.

32. A method of delivering a combination of agents to a mammalian tissue, wherein the method comprises contacting the medical article of claim 1 with the mammalian tissue under in vivo conditions.

33. The method of claim 32, wherein the tissue comprises a vascular tissue.

34. A method of preventing or treating a disease comprising implanting the medical article of claim 1 in a subject.

35. The method of claim 34, wherein the disease is a vascular disease.

36. The method of claim 35, wherein the vascular disease is restenosis, vulnerable plaque, or a combination thereof.

* * * * *